United States Patent
Kovatchev et al.

(10) Patent No.: US 8,538,703 B2
(45) Date of Patent: Sep. 17, 2013

(54) METHOD, SYSTEM, AND COMPUTER PROGRAM PRODUCT FOR THE PROCESSING OF SELF-MONITORING BLOOD GLUCOSE(SMBG)DATA TO ENHANCE DIABETIC SELF-MANAGEMENT

(75) Inventors: Boris P. Kovatchev, Charlottesville, VA (US); Daniel J. Cox, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 2286 days.

(21) Appl. No.: 10/524,094

(22) PCT Filed: Aug. 8, 2003

(86) PCT No.: PCT/US03/25053
§ 371 (c)(1),
(2), (4) Date: Feb. 9, 2005

(87) PCT Pub. No.: WO2004/015539
PCT Pub. Date: Feb. 19, 2004

(65) Prior Publication Data
US 2005/0214892 A1    Sep. 29, 2005

Related U.S. Application Data

(60) Provisional application No. 60/402,976, filed on Aug. 13, 2002, provisional application No. 60/478,377, filed on Jun. 13, 2003.

(51) Int. Cl.
*G06F 19/00* (2011.01)
*A61B 5/00* (2006.01)
*A61B 5/05* (2006.01)

(52) U.S. Cl.
USPC .............................. 702/19; 600/365; 600/347

(58) Field of Classification Search
None
See application file for complete search history.

(56) References Cited

U.S. PATENT DOCUMENTS

| | | |
|---|---|---|
| 4,731,726 A | 3/1988 | Allen, III |
| 4,975,581 A | 12/1990 | Robinson et al. |
| 5,019,974 A | 5/1991 | Beckers |
| 5,036,861 A | 8/1991 | Sembrowich et al. |
| 5,076,273 A | 12/1991 | Schoendorfer et al. |
| 5,086,229 A | 2/1992 | Rosenthal et al. |
| 5,108,564 A | 4/1992 | Szuminski et al. |
| 5,128,015 A | 7/1992 | Szuminski et al. |
| 5,139,023 A | 8/1992 | Stanley et al. |
| 5,140,985 A | 8/1992 | Schroeder et al. |
| 5,206,144 A | 4/1993 | Zeuthen et al. |
| 5,251,126 A | 10/1993 | Kahn et al. |
| 5,267,152 A | 11/1993 | Yang et al. |
| 5,279,543 A | 1/1994 | Glikfeld et al. |
| 5,431,793 A | 7/1995 | Wang et al. |
| 5,453,379 A | 9/1995 | Yamazaki et al. |
| 5,558,638 A | 9/1996 | Evers et al. |
| 5,724,580 A | 3/1998 | Levin et al. |
| 5,741,211 A | 4/1998 | Renirie et al. |
| 5,748,851 A | 5/1998 | Iokibe et al. |
| 5,801,057 A | 9/1998 | Smart et al. |
| 5,822,715 A | 10/1998 | Worthington et al. |
| 5,840,020 A | 11/1998 | Heinonen et al. |
| 5,882,935 A | 3/1999 | Hirai et al. |
| 5,971,922 A | 10/1999 | Arita et al. |
| 5,989,409 A | 11/1999 | Kurnik et al. |
| 5,997,476 A | 12/1999 | Brown |
| 6,027,692 A | 2/2000 | Galen et al. |
| 6,054,039 A | 4/2000 | Shieh |
| 6,081,786 A | 6/2000 | Barry et al. |
| 6,144,869 A | 11/2000 | Berner et al. |
| 6,175,752 B1 | 1/2001 | Say et al. |
| 6,188,988 B1 | 2/2001 | Barry et al. |
| 6,233,471 B1 | 5/2001 | Berner et al. |
| 6,272,480 B1 | 8/2001 | Tresp et al. |
| 6,421,633 B1 * | 7/2002 | Heinonen et al. ............... 703/11 |
| 7,025,425 B2 * | 4/2006 | Kovatchev et al. ............ 600/365 |

FOREIGN PATENT DOCUMENTS

| | | |
|---|---|---|
| DE | 20305978 U1 | 7/2003 |
| EP | 0834825 | 4/1998 |
| GB | 2159625 A | 12/1985 |

(Continued)

OTHER PUBLICATIONS

Cox, et al.: "Frequency of Severe Hypoglycemia in Insulin-Dependent Diabetes Mellitus Can be Predicted from Self-Monitoring Blood Glucose . . . " J of Clinical End. and Met., vol. 79, No. 6, pp. 1659-1662. (1994).

Kovatchev, et al.: "Assessment of Risk for Severe Hypoglycemia Among Adults with IDDM", Diabetes Care, vol. 21, No. 11, Nov. 1998.

Kovatchev, et al.: "Symmetrization of the Blood Glucose Measurement Scale and its Applications", Diabetes Care, vol. 20, No. 11, Nov. 1997.

Kovatchev, et al.: "Risk Analysis of Blood Glucose Data: A Quantitative Approach to Optimizing the Control of Insulin Dependent Diabetes", J. of Theoretical Medicine, pp. 1-10, Jan. 2000.

(Continued)

*Primary Examiner* — Lori A Clow
(74) *Attorney, Agent, or Firm* — Novak Druce Connolly Bove + Quigg LLP; Vincent M. DeLuca; Robert J. Decker

(57) ABSTRACT

A method, system, and computer program product related to the maintenance of optimal control of diabetes, and is directed to predicting the long-term exposure to hyperglycemia, and the long-term and short-term risks of severe or moderate hypoglycemia in diabetics, based on blood blucose readings collected by a self-monitoring blood glucose device. The method, system, and computer program product pertain directly to the enhancement of existing home blood glucose monitoring devices, by introducing an intelligent data interpretation component capable of predicting both HbA1c and periods of increased risk of hypoglycemia, and to the enhancement of emerging continuous monitoring devices by the same features. With these predictions the diabetic can take steps to prevent the adverse consequences associated with hyperglycemia and hypoglycemia.

93 Claims, 19 Drawing Sheets

(56) References Cited

FOREIGN PATENT DOCUMENTS

| WO | WO 9600110 | 1/1996 |
|---|---|---|
| WO | WO 9929230 | 6/1999 |
| WO | WO 0018289 | 4/2000 |
| WO | WO 0018293 | 4/2000 |
| WO | WO 0019888 | 4/2000 |
| WO | 01/72208 A2 | 10/2001 |

OTHER PUBLICATIONS

Kovatchev, et al.: "Assoc. of Self-Monitoring Blood Glucose Profiles with Glycosylated Hemoglobin in Patients . . . ", Methods in Enzymology, vol. 321, pp. 410-417, (2000).

Lehmann, E.D., et al.: "Computer assisted diabetes care: a 6-year retrospective", Computer Methods and Programs in Biomedicine, 50, 209-230 (1996).

Deutsch, T., et al.: "Time series analysis and control of blood glucose levels in diabetic patients", Computer Methods and Programs in Biomedicine, 41, 167-182 (1994).

Lehmann, E.D., et al.: "AIDA: an interactive diabetes advisor", Computer Methods and Programs in Biomedicine, 41, 183-203, (1994).

Lehmann, E.D., et al.: "Retrospective validation of physiological model of glucose-insulin interaction in type 1 diabetes mellitus", Med. Eng. Phys., vol. 16, 193-202, May 1994.

Lehmann, E.D., et al.: "Extended Conference Report: Computers in Diabetes '96", Med. Inform, vol. 22, No. 1, 105-118, (1997).

Lehmann, E.D., et al.: "Application of computers in diabetes care—a review. I. Computers for data collection and interpretation", vol. 20, No. 4, 281-302, (1995).

Deutsch, T. et al.: "UTOPIA: a consultation system for visit-by-visit diabetes management", Med Inform, vol. 21, No. 4, 345-358 (1996).

Lehmann, E.D., et al.: "Compartmental models for glycaemic prediction and decision-support in clinical diabetes care: promise and reality" Computer Methods and Programs in Biomedicine, vol. 56, 193-204, (1998).

Lehmann, E.D., et al.: "A physiological model of glucose—insulin interaction in type 1 diabetes mellitus", J. of Biomedical Engineering vol. 14, No. 3, 235-242 (1992).

Trajanoski, Zlatko, et al.: "Simulation studies on neural predictive control of glucose using the subcutaneous route", Comp Methods and Programs in Biomed., vol. 56, Iss 2, 133-139, May 1998.

Trajanoski, Zlatko, et al.: "Fuzzy filter for state estimation of a glucoregulatory system", Comp. Methods and Programs in Biomedicine, vol. 50, 265-273, (1996).

Regittnig, W. et al.: "Glucose-mediated glucose disappearance during the intravenous . . . ", 18th Annual International Conference of the IEEE Eng. in Medicine and Biology Society, Amsterdam, 0-7803-3811-1/97, 1996.

Fischer, Uwe, et al.: "Experimental validation of a glucose-insulin control model to simulate patterns in glucose turnover", Comp. Methods and Programs in Biomedicine, vol. 32, 249-258 (1990).

Salzsieder, E., et al.: "A Model-based System for the Individual Prediction of Metabolic Responses to Improve Therapy in Type 1 Diabetes", Central Inst. of Diabetes, Horm. Metab. Res, 24 (Suppl) 10-19 (1990).

Salzsieder, Eckhard, et al.: "Computer-aided systems in the management of type I diabetes: the application of a model-based strategy", Computer Methods and Programs in Biomedicine, vol. 32, 215-224, (1990).

Bleckert, Gabriele, et al.: "Mixed graphical models for simultaneous model identification and control applied to the glucose-insulin metabolism", Computer Method and Programs in Biomed vol. 56, 141-155 (1998).

Martin, Iva K, et al.: "Application of the SAAM modeling program to minimal model analysis of intravenous glucose tolerance test data", Computer Methods and Programs in Biomedicine, vol. 33 193-203(1990).

Ward, G. M., et al.: "Physiologic Modeling of the Intravenous Glucose Tolerance Test in Type 2 Diabetes: A new Approach to the Insulin Compartment", Metabolism, vol. 50, No. 5, 512-519, May 2001.

Ward, G. M., et al.: "A Modified Minimal Model Analysis of Insulin Sensitivity and Glucose-Mediated Glucose Disposal in Insulin-Dependent Diabetes", Metabolism, vol. 40, No. 1, 4-9, Jan. 1991.

Thomaseth, Karl, et al.: "Parameter Information Content During Model Identification Experiments", 3rd IFAC Symposium on Modelling and Control in Biomedical Systems, Warwick UK, 107-112 (1997).

Pacini, Giovanni, et al.: "Estimation of B-cell Secretion and insulin hepatic extraction by the minimal modelling technique", Computer Methods and Programs in Biomedicine, vol. 32, 241-248 (1990).

Bellazzi, R., et al.: "Bayesian Analysis of Blood Glucose Time Series from Diabetes Home Monitoring", IEEE Transactions on Biomedical Engineering, vol. 47, No. 7, 971-, Jul. 2000.

Bellazzi, R, et al.: "The Subcutaneous Route to Insulin-Dependent Diabetes Therapy", IEEE Engineering in Med. and Bio., vol. 20, No. 1, 54-64, Jan 2001.

Riva, A., et al.: "High Level Control Strategies for Diabetes Therapy", Proceedings of the Fifth Conference on Artificial Intelligence in Medicine Europe, No. 934 in Lecture Notes in Artificial Intelligence, p. 185-196, (1995).

Arleth, T. et al.: "A model of the edogenous glucose balance incorporating the characteristics of glucose transporters", Computer Methods and Programs in Biomedicine, vol. 62, 219-234, (2000).

Sturis, Jeppe, et al.: "Computer model for mechanisms underlying ultradian oscillations of insulin and glucose", Am. J. of Physiol., Modeling Methodology Forum, E801-E809, (1991).

Quon, Michael, et al.: "Non-Insulin-Mediated Glucose Disappearance in Subjects with IDDM Discordance Between . . . ", Diabetes, vol. 43, 890-, Jul. 1994.

Muzic, R. et al.: "COMKAT: Compartment Model Kinetic Analysis Tool", The Journal of Nuclear Medicine, vol. 42, No. 4, Apr. 2001.

Freeland, Angela, et al.: "Inference of Blood Glucose Concentrations form Subcutaneous Glucose . . . ", Annals of Biomedical Engineering, vol. 27, 525-537, (1999).

Berger, Marcus, et al.: "Computer Simulation of Plasma Insulin and Glucose Dynamics After Subcutaneous Insulin Injection", Diabetes Care, vol. 12, No. 10, Nov. 1989.

Finegood, D., et al.: "Reduced glucose effectiveness associated with reduced insulin release: an artifact of the minimal-model method", Am. J. of Physiol. Endocrin. Metab. 271, E485-E495, (1996).

Naylor, J. S., et al.: "Comparison of parametrized models for computer-based estimation of diabetic patient glucose response", Med. Inform., vol. 22, No. 1, 21-34, (1997).

Andreassen, S.: "Model-Based Biosignal Interpretation", Meth Inform Med, vol. 33, 103-110, (1994).

Worthington, D.: "The use of models in the self-management of insulin-dependent diabletes mellitus", Computer Methods and Programs in Biomedicine, vol. 32, 233-239, (1990).

Carson, E.R.: "Information technology and computer-based decision support in diabetic management", Computer Methods and Programs in Biomedicine, vol. 32, 179-188, (1990).

Gomez, E.J, et al.: "Telemedicine for diabetes care: the DIABTel approach towars diabetes telecare", Med. Inform., vol. 21, No. 4, 283-295, (1996).

Trajanoski, Zlatko, et al.: "Neural Predictive Controller for Insulin Delivery Using the Subcutaneous Route", IEEE Transactions on Biomedical Engineering, vol. 45, No. 9, Sep. 1998.

Berger, M.P.: "Combining Statistical, Rule-Based, and Physiologic Model-Based Methods to Assist in the Management . . . ", Computer and Biomedical Research, vol. 23, 346-357, (1990).

Fisher, Michael: "A Semiclosed-Loop Algorithm for the Control of Blood Glucose Levels in Diabetics", IEEE Transactions on Biomedical Engineering, vol. 38, No. 1, Jan. 1991.

Hernando, M.E. et al.: "DIABNET, a qualitative model-based advisory system for therapy planning in gestational diabetes", Med. Inform. vol. 21, No. 4, 359-374, (1996).

Kienitz, Karl H., et al.: "A Robust Controller for Insulin Pumps Based on H-Infinity Theory", IEEE Transactions on Biomedical Engineering, vol. 40, No. 11, Nov. 1993.

Parker, Robert, et al.: "Control-relevant modeling in drug delivery", Advanced Drug Delivery Reviews, vol. 48, 211-228, (2001).

Carson, E.R., et al.:"Computers in Diabetes—an Introduction", Computer Meth Prg. Biomed., vol. 62, 153-155, (2000).

Hauser, Thomas, et al.: "Assessment of Experts' Approach to Insulin Therapy . . . ", Diabetes Care, vol. 15, No. 2, pp. 221-, Feb. 1992.
Garcia, Alejandro,: "The Bergman's Insulin-Glucose Regulation Model: DNN-state Observer", Proceedings of the 22nd Annual EMBS International Conf., Jul. 23-28, Chicago, IL. (2000).
Sandham, W.A., et al.: "Neural Network and Neuro-Fuzzy Systems for Improving Diabetes Therapy", Proceedings of the 20th Annual International Conference of the IEEE Engineering in Medicine and Biology Society, vol. 20, No. 3, part 3/6, p. 1438-1441(1998).
Parker, R.S. et al: "Time and Frequency Domain Analysis of Blood Glucose Regulation Algorithms", Proceedings—19th International Conference—IEEE/EMBS, Chicago, IL, Oct. 30-Nov. 2, 1997.
Parker, Robert S., et al: "The Intravenous Route to Blood Glucose Control", IEEE Engineering in Medicine and Biology, pp. 65-, Jan. 2001.
Parker, Robert S., et al.: "A Model-Based Algorithm for Blood Glucose Control in Type 1 Diabetic Patients", IEEE Transactions on Biomedical Engineering, vol. 46, No. 2, pp. 148-, Feb. 1998.
Puckett, Wanda, et al.: "A model for multiple subcutaneous insulin injections developed from individual diabetic patient data", Am. J. Physiol Endocrinol Metab, 269 Modeling in Physiology, E1115-E1124, (1995).
Kan, Shugen, et al.: "Novel Control System for Blood Glucose Using a Model Predictive Method", ASAIO Journal, pp. 657-, (2000).
Candas, B.et al.: "An Adaptive Plasma Glucose Controller Based on a Nonlinear Insulin/Glucose Model", IEEE Transactions on Biomedical Engineering, vol. 41, No. 2, pp. 116-, Feb. 1994.
Robinson, David, et al.: "Knowledge of Diabetes mellitus and glycaemic control", Med. Principles Pract. vol. 6, 186-197 (1997).
Toth, Michael, et al.: "Determinants of insulin-stimulated glucose disposal in middle-aged, premenopausal women", Am J Physiol Endocriol Metab., vol. 281, E113-E121, (2001).
Bando, Yukihiro, et al.: "The Relationship of Fasting Plasma Glucose Values and Other Variables to 2-h . . . ", Diabetes Care, vol. 24, No. 7, pp. 1156-, Jul. 2001.
Liszka-Hackzell, Jan John,: "Prediction of Blood Glucose Levels in Diabetic Patients Using a Hybrid AI Technique", Computers and Biomedical Research, vol. 32, 132-144 (1999).
Waldhausl, Werner, et al.: "Blood Glucose Response to Stress Hormone Exposure in Healthy Man . . . ", IEEE Transactions on Biomedical Engineering, vol. 39, No. 8, Aug. 1992.
Hastings, Gregory, et al.: "A Self-Organising Fuzzy Estimator for Hypoglycaemia Monitoring in Diabetic Patients", Proceedings of the 20th Annual International Conference of the IEEE Engineering in Medicine and Biology Society, vol. 20, No. 3, pp. 1371-, (1998).
Tresp, Volker, et al.: "Neural-Network Models for the Blood Glucose Metabolism of a Diabetic", IEEE Transactions on Neural Networks, vol. 10, No. 5, pp. 1204-1213, Sep. 1999.
Yates, Tony, et al.: "Prediction of a glucose appearance function from foods using deconvolution", IMA Journal of Mathematics Applied in Medicine and Biology, vol. 17, 169-184, (2000).
Hejlesen, Ole, et al.: DiasNet: an internet tool for communication and education in diabetes, Medical infobahn for Europe, Proceedings of MIE2000 and GMDX2000, pp. 563-567, Studies in health technology and informatics, 77, (2000).
Cavan, D.A., et al.: "Use of the DIAS model to predict unrecognised hypoglyceamia in patients with insulin-dependent diabetes", Computer Methods and Programs in Biomedicine, vol. 50, 241-246, (1996).
Hejlesen, Ole, et al.: "Analysing the hypoglyceamic counter-regulation: a clinically relevant phenomenon?", Computer Methods and Programs in Biomedicine, vol. 50, 231-240, (1996).
Hejlesen, Ole, et al.: "Dynamic Propagation in Causal Problistic networks with Instantiated Variable", Artificial Intelligence in Medicine: Proceedings of the 5th Conference on Artificial Intelligence in Medicine, 151-162, (1995).
Cavan, DA, et al.: "Preliminary experience of the DIAS computer model in providing insulin dose advice to patients with insulin dependent diabetes", Computer Methods and programs in Biomedicine, vol. 56, p. 157-164, (1998).
Andreassen, Steen, et al.:"A probabilistic approach to glucose prediction and insulin dose adjustment; description of metabolic model and pilot evaluation study", Computer Methods and Programs in Biomedicine, vol. 41, 153-165, (1994).
Tudor, Romulus, et al.: "DIAS-NIDDM—a model-based decision support system for insulin dose adjustment in insulin-treated subjects with NIDDM", Computer Methods and Programs in Biomedicine, vol. 56, 175-192, (1998).
Gold, A.E., et al.: "A Structural Equation Model for Predictors of Severe Hypoglycaemia in Patients with Insulin-dependent Diabetes Mellitus", Diabetic medicine, vol. 14, 309-315, (1997).
Bremer, Troy, et al.: "Is Blood Glucose Predictable from Previous Values? A solicitation for data", Diabetes, vol. 48, pp. 445-451, Mar. 1999.
Boyle, Patrick, et al.: "Plasma Glucose Concentrations at the onset of Hypoglyemic symptoms in Patients with Poorly Controlled Diabetes and in Nondiabetics", Plasma Glucose Concentrations and Hypoglycemia, vol. 318, No. 33, 1487-1492, (1988).
Carson, Ewart: "A systems model of Blood Glucose control", Int. J. Bio-Medical computing, vol. 7, pp. 21-34, (1976).
Worthington, D.R.L.: "Minimal Model of Food Absorption in the gut", Med. Inform., vol. 22, No. 1, 35-45 (1997).
Worthington, D.R.L.: "Controlling blood Glucose: insights from an engineering control systems perspective", Med. Inform. vol. 22, No. 1, 5-19 (1997).
DCCT Research Group: "The effect of intensive treatment of diabetes on the development and progression of Long-term complications of insulin-dependent diabetes Mellitus", New England Journal of Medicine, vol. 329, 977-986 (1993).
Reichard, P, et al.: "Mortality and Treatment Side Effects During Long-term Intensified Conventional Insulin Treatment in the Stockholm Diabetes Intervention Study", Diabetes, vol. 43, 313-317 (1994).
UK Prospective Diabetes Study Group: Effect of Intensive Blood Glucose Control with Metformin on Complications in Patients with Type 2 Diabetes (UKPDS34), Lancet, vol. 352, 854-865, (1998).
DCCT Research Group: "Epidemiology of Severe Hypoglycemia in the diabetes control and complications trial", Amer. J. of Med., Vo. 90, 450-459, (1991).
DCCT Research Group: "Hypoglycemia in the Diabetes control and complications Trial", Diabetes, vol. 46, 271-286, (1997).
Cryer, PE: "Hypoglycemia is the limiting factor in the management of Diabetes", Diabetes Metab Res Rev, vol. 15, 42-46, (1999).
Svendson, Aaby, et al.: "Glycosylated Hemoglobin and Steady-State Mean Blood Glucose Concentration in Type 1 (Insulin-Dependent)Diabetes", Diabetologia, vol. 23, 403-405, (1982).
Santiago, J.V.: "Lessons from the Diabetes Control and Complications Trial", Diabetes, vol. 42, 1549-1554, (1993).
Bolli, G.B.: "How to Ameliorate the Problem of Hypoglycemia in Intensive as well as Nonintensive Treatment of Type 1 Diabetes", Diabetes Care, vol. 22, Supplement 2, B43-B52, (1999).
Bremer, T, et al.: "Is blood glucose predictable from previous values? A solicitation for data", Diabetes, vol. 48, 445-451, (1999).
Kovatchev, B.P., et al.: "Estimating the speed of Blood Glucose Transitions and its relationship with Severe Hypoglycemia", Diabetes, 48: Supplement 1, A363, (1999).

* cited by examiner

FIG. 4 Probability of >= 2 Moderate or Severe Hypoglycemias within 3 Months

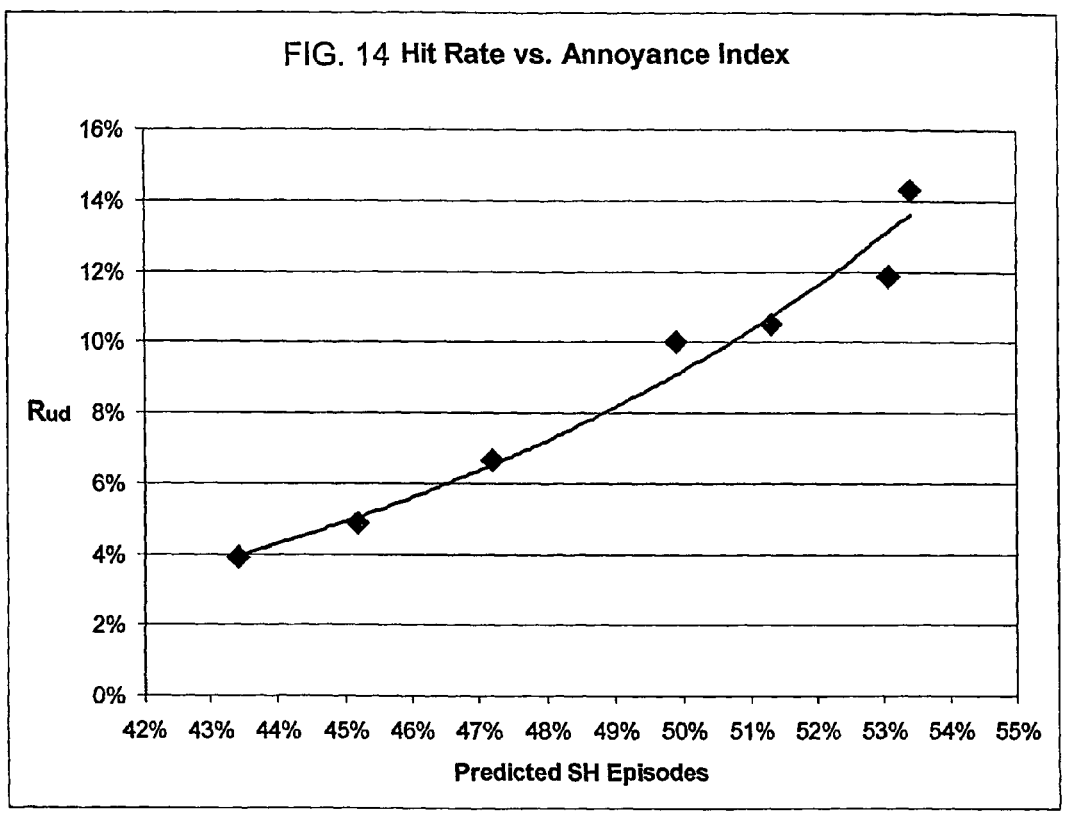

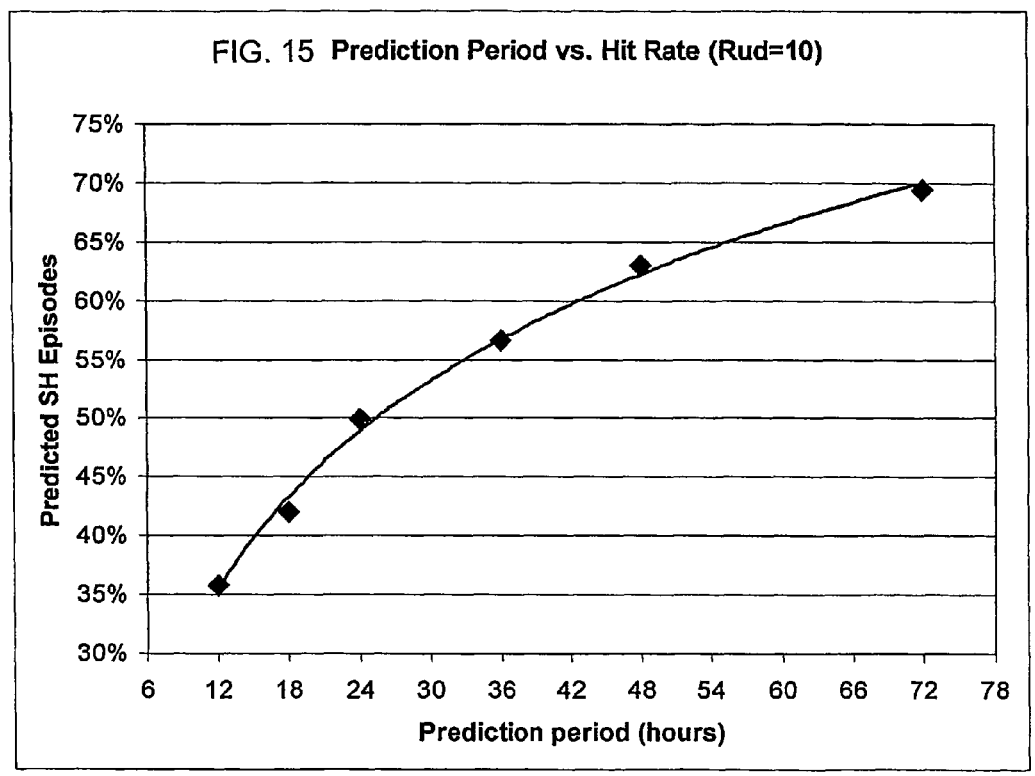

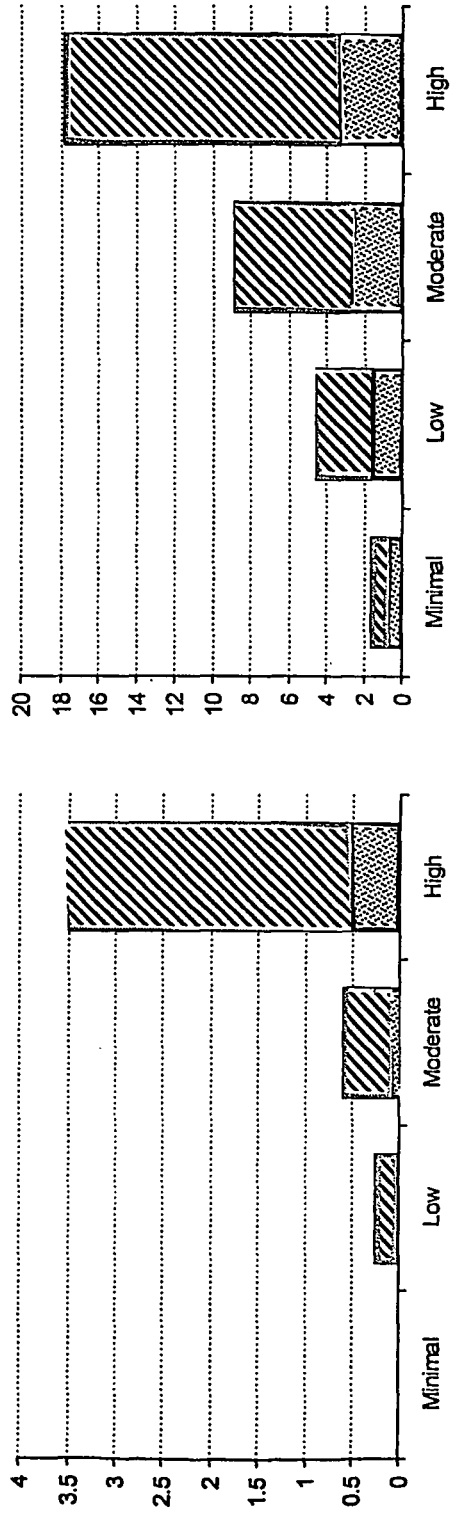

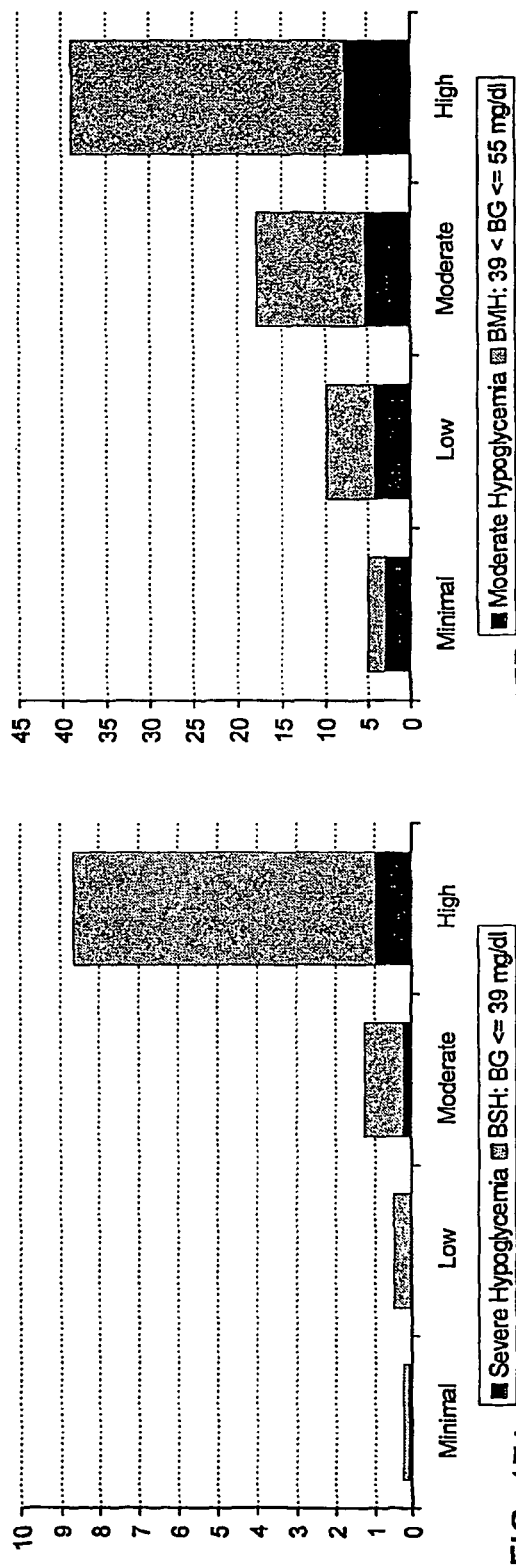

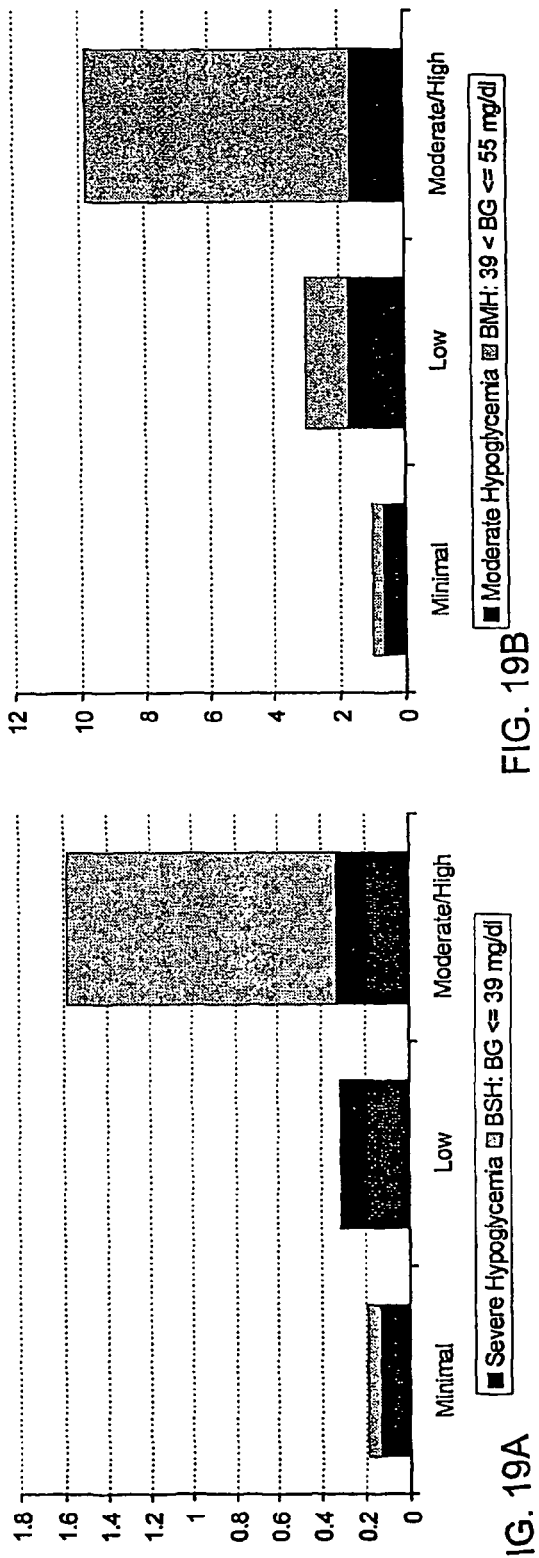

METHOD, SYSTEM, AND COMPUTER PROGRAM PRODUCT FOR THE PROCESSING OF SELF-MONITORING BLOOD GLUCOSE(SMBG)DATA TO ENHANCE DIABETIC SELF-MANAGEMENT

RELATED APPLICATIONS

The present application is a national stage filing of International Application No. PCT/US2003/025053, filed Aug. 8, 2003, which claims the benefit of priority under 35 U.S.C. Section 119(e) from U.S. Provisional Application Ser. No. 60/402,976, filed Aug. 13, 2002, entitled "Method, System, and Computer Program Product for Processing of Self-monitoring Blood Glucose (SMBG) Data to Enhance Diabetic Self-management," and No. 60/478,377, filed Jun. 13, 2003, entitled "Method, System, and Computer Program Product for Processing of Self-monitoring Blood Glucose (SMBG) Data to Enhance Diabetic Self-management," the entire disclosures of all three disclosures are hereby incorporated by reference herein.

The present application is related to International Application No. PCT/US01/09884, filed Mar. 29, 2001 (Publication Nos. WO 01/72208 A2, WO 01/72208 A3), entitled "Method, System, and Computer Program Product for the Evaluation of Glycemic Control in Diabetes from Self-monitoring Data," and U.S. patent application Ser. No.:10/240,228 filed Sep. 26, 2002, entitled "Method, System, and Computer Program Product for the Evaluation of Glycemic Control in Diabetes from Self-monitoring Data," the entire disclosures of which are hereby incorporated by reference herein.

FIELD OF THE INVENTION

The present system relates generally to Glycemic Control of individuals with diabetes, and more particularly to a computer-based system and method for evaluation of predicting glycosylated hemoglobin ($HbA_{1c}$ and $HbA_1$) and risk of incurring hypoglycemia.

BACKGROUND OF THE INVENTION

Extensive studies, including the Diabetes Control and Complications Trial (DCCT) (See DCCT Research Group: The Effect Of Intensive Treatment Of Diabetes On The Development And Progression Of Long-Term Complications Of Insulin-Dependent Diabetes Mellitus. *New England Journal of Medicine,* 329: 978-986, 1993), the Stockholm Diabetes Intervention Study (See Reichard P, Phil M: Mortality and Treatment Side Effects During Long-term Intensified Conventional Insulin Treatment in the Stockholm Diabetes Intervention Study. *Diabetes,* 43: 313-317, 1994), and the United Kingdom Prospective Diabetes Study (See UK Prospective Diabetes Study Group: Effect of Intensive Blood Glucose Control With Metformin On Complications In Patients With Type 2 Diabetes (UKPDS 34). *Lancet,* 352: 837-853, 1998), have repeatedly demonstrated that the most effective way to prevent the long term complications of diabetes is by strictly maintaining blood glucose (BG) levels within a normal range using intensive insulin therapy.

However, the same studies have also documented some adverse effects of intensive insulin therapy, the most acute of which is the increased risk of frequent severe hypoglycemia (SH), a condition defined as an episode of neuroglycopenia which precludes self-treatment and requires external help for recovery (See DCCT Research Group: Epidemiology of Severe Hypoglycemia In The Diabetes Control and Complications Trial. *American Journal of Medicine,* 90: 450-459, 1991, and DCCT Research Group: Hypoglycemia in the Diabetes Control and Complications Trial. *Diabetes,* 46: 271-286, 1997). Since SH can result in accidents, coma, and even death, patients and health care providers are discouraged from pursuing intensive therapy. Consequently, hypoglycemia has been identified as a major barrier to improved glycemic control (Cryer PE: Hypoglycemia is the Limiting Factor in the Management Of Diabetes. *Diabetes Metab Res Rev,* 15: 42-46, 1999).

Thus, patients with diabetes face a life-long optimization problem of maintaining strict glycemic control without increasing their risk of hypoglycemia. A major challenge related to this problem is the creation of simple and reliable methods that are capable of evaluating both patients' glycemic control and their risk of hypoglycemia, and that can be applied in their everyday environments.

It has been well known for more than twenty years that glycosylated hemoglobin is a marker for the glycemic control of individuals with Diabetes Mellitus (Type I or Type II). Numerous researchers have investigated this relationship and have found that glycosylated hemoglobin generally reflects the average BG levels of a patient over the previous two months. Since in the majority of patients with diabetes the BG levels fluctuate considerably over time, it was suggested that the real connection between integrated glucose control and $HbA_{1c}$ would be observed only in patients known to be in stable glucose control over a long period of time.

Early studies of such patients produced an almost deterministic relationship between the average BG level in the preceding 5 weeks and $HbA_{1c}$, and this curvilinear association yielded a correlation coefficient of 0.98 (See Aaby Svendsen P, Lauritzen T, Soegard U, Nerup J (1982). Glycosylated Hemoglobin and Steady-State Mean Blood Glucose Concentration in Type 1 (Insulin-Dependent) Diabetes, *Diabetologia,* 23, 403-405). In 1993 the DCCT concluded that $HbA_{1c}$ was the "logical nominee" for a gold-standard glycosylated hemoglobin assay, and the DCCT established a linear relationship between the preceding mean BG and $HbA_{1c}$ (See Santiago J V (1993). Lessons from the Diabetes Control and Complications Trial, *Diabetes,* 42, 1549-1554).

Guidelines were developed indicating that an $HbA_{1c}$ of 7% corresponds to a mean BG of 8.3 mM (150 mg/dl), an $HbA_{1c}$ of 9% corresponds to a mean BG of 11.7 mM (210 mg/dl), and a 1% increase in $HbA_{1c}$ corresponds to an increase in mean BG of 1.7 mM (30 mg/dl, 2). The DCCT also suggested that because measuring the mean BG directly is not practical, one could assess a patient's glycemic control with a single, simple test, namely $HbA_{1c}$. However, studies clearly demonstrate that $HbA_{1c}$ is not sensitive to hypoglycemia.

Indeed, there is no reliable predictor of a patient's immediate risk of SH from any data. The DCCT concluded that only about 8% of future SH could be predicted from known variables such as the history of SH, low $HbA_{1c}$, and hypoglycemia unawareness. One recent review details the current clinical status of this problem, and provides options for preventing SH, that are available to patients and their health care providers (See Bolli, GB: How To Ameliorate The Problem of Hypoglycemia In Intensive As Well As Nonintensive Treatment Of Type I Diabetes. *Diabetes Care,* 22, Supplement 2: B43-B52, 1999).

Contemporary home BG monitors provide the means for frequent BG measurements through Self-Monitoring of BG (SMBG). However, the problem with SMBG is that there is a missing link between the data collected by the BG monitors, and $HbA_{1c}$ and hypoglycemia. In other words, there are currently no reliable methods for evaluating $HbA_{1c}$ and recognizing imminent hypoglycemia based on SMBG readings (See Bremer T and Gough DA: Is blood glucose predictable from previous values? A solicitation for data. *Diabetes* 48:445-451, 1999).

Thus, an object of this invention is to provide this missing link by proposing three distinct, but compatible, algorithms for evaluating $HbA_{1c}$ and the risk of hypoglycemia from SMBG data, to be used to predict the short-term and long-term risks of hypoglycemia, and the long-term risk of hyperglycemia.

The inventors have previously reported that one reason for a missing link between the routinely available SMBG data and the evaluation of $HbA_{1c}$ and the risk of hypoglycemia, is that the sophisticated methods of data collection and clinical assessment used in diabetes research, are infrequently supported by diabetes-specific and mathematically sophisticated statistical procedures.

Responding to the need for statistical analyses that take into account the specific distribution of BG data, the inventors developed a symmetrizing transformation of the blood glucose measurement scale (See Kovatchev B P, Cox D J, Gonder-Frederick L A and W L Clarke (1997). Symmetization of the Blood Glucose Measurement Scale and Its Applications, *Diabetes Care*, 20, 1655-1658) that works as the follows. The BG levels are measured in mg/dl in the United States, and in mmol/L (or mM) in most other countries. The two scales are directly related by 18 mg/dl=1 mM. The entire BG range is given in most references as 1.1 to 33.3 mM, and this is considered to cover practically all observed values. According to the recommendations of the DCCT (See DCCT Research Group (1993) The Effect Of Intensive Treatment of Diabetes On the Development and Progression of Long-Term Complications of Insulin-Dependent Diabetes Mellitus. *New England Journal of Medicine*, 329, pp 978-986) the target BG range—also known as the euglycemic range—for a person with diabetes is 3.9 to 10 mM, hypoglycemia occurs when the BG falls below 3.9 mM, and hyperglycemia is when the BG rises above 10 mM. Unfortunately, this scale is numerically asymmetric—the hyperglycemic range (10 to 33.3 mM) is wider than the hypoglycemic range (1.1 to 3.9 mM), and the euglycemic range (3.9 to 10 mM) is not centered within the scale. The inventors correct this asymmetry by introducing a transformation, f(BG), which is a continuous function defined on the BG range [1.1, 33.3], having the two-parameter analytical form:

$$f(BG, \alpha, \beta) = [ln(BG))^\alpha - \beta], \alpha, \beta > 0$$

and which satisfies the assumptions:

$$A1: f(33.3, \alpha, \beta) = -f(1.1, \alpha, \beta) \text{ and}$$

$$A2: f(10.0, \alpha, \beta) = -f(3.9, \alpha, \beta).$$

Next, f(.) is multiplied by a third scaling parameter to fix the minimum and maximum values of the transformed BG range at $-\sqrt{10}$ and $\sqrt{10}$ respectively. These values are convenient since a random variable with a standard normal distribution has 99.8% of its values within the interval $[-\sqrt{10}, \sqrt{10}]$. If BG is measured in mmol/l, when solved numerically with respect to the assumptions A1 and A2, the parameters of the function f(BG, $\alpha$, $\beta$) are $\alpha=1.026$, $\beta=1.861$, and the scaling parameter is $\gamma=1.794$. If BG is measured in mg/dl instead, the parameters are computed to be $\alpha=1.084$, $\beta=5.381$, and $\gamma=1.509$.

Thus, when BG is measured in mmol/l, the symmetrizing transformation is $f(BG)=1.794[(ln(BG))^{1.026}-1.861]$. and when BG is measured in mg/dl the symmetrizing transformation is $f(BG)=1.509[(ln(BG))^{1.084}-5.381]$.

On the basis of the symmetrizing transformation f(.) the inventors introduced the Low BG Index—a new measure for assessing the risk of hypoglycemia from SMBG readings (See Cox D J, Kovatchev B P, Julian D M, Gonder-Frederick L A, Polonsky W H, Schlundt D G, Clarke W L: Frequency of Severe Hypoglycemia In IDDM Can Be Predicted From Self-Monitoring Blood Glucose Data. *Journal of Clinical Endocrinology and Metabolism*, 79: 1659-1662, 1994, and Kovatchev B P, Cox D J, Gonder-Frederick L A Young-Hyman D, Schlundt D, Clarke W L. Assessment of Risk for Severe Hypoglycemia Among Adults With IDDM: Validation of the Low Blood Glucose Index, *Diabetes Care* 21:1870-1875, 1998). Given a series of SMBG data the Low BG Index is computed as the average of $10.f(BG)^2$ taken for values of f(BG)<0 and 0 otherwise. Also suggested was a High BG Index, computed in a symmetrical to the Low BG Index manner, however this index did not find its practical application.

Using the Low BG Index in a regression model the inventors were able to account for 40% of the variance of SH episodes in the subsequent 6 months based on the SH history and SMBG data, and later to enhance this prediction to 46% (See Kovatchev B P, Straume M, Farhi L S, Cox D J: Estimating the Speed of Blood Glucose Transitions and its Relationship With Severe Hypoglycemia. Diabetes, 48: Supplement 1, A363, 1999).

In addition, the inventors developed some data regarding $HbA_{1c}$ and SMBG (See Kovatchev B P, Cox D J, Straume M, Farhy L S. Association of Self-monitoring Blood Glucose Profiles with Glycosylated Hemoglobin. *In: Methods in Enzymology*, vol. 321: *Numerical Computer Methods, Part C*, Michael Johnson and Ludvig Brand, Eds., Academic Press, NY; 2000).

These developments became a part of the theoretical background of this invention. In order to bring this theory into practice, several key theoretical components, among other things, as described in the following sections, were added. In particular, three methods were developed for employing the evaluation of $HbA_{1c}$, long-term and short-term risk for hypoglycemia. The development of these methods was, but not limited thereto, based on detailed analysis of data for 867 individuals with diabetes that included more than 300,000 SMBG readings, records of severe hypoglycemia and determinations of $HbA_{1c}$.

The inventors have therefore sought to improve upon the aforementioned limitations associated with the conventional methods, and thereby provide simple and reliable methods that are capable of evaluating both patients' glycemic control and their risk of hypoglycemia, and that can be applied in their everyday environments.

SUMMARY OF THE INVENTION

The invention includes a data analysis method and computer-based system for the simultaneous evaluation, from routinely collected SMBG data, of the two most important components of glycemic control in diabetes: $HbA_{1c}$ and the risk of hypoglycemia. For the purposes of this document, self-monitoring of BG (SMBG) is defined as any method for determination of blood glucose at diabetic patients' natural environment and includes the methods used by contemporary SMBG devices customarily storing 200-250 BG readings, as well as methods used by emerging continuous monitoring technologies. Given this broad definition of SMBG, this invention pertains directly to the enhancement of existing home blood glucose monitoring devices (but not limited thereto) by introducing an intelligent data interpretation component capable of predicting both $HbA_{1c}$ and periods of increased risk of hypoglycemia, as well as to enhancement of future continuous monitoring devices by the same features.

One aspect of the invention includes a method, system, and computer program product for evaluating $HbA_{1c}$ from a predetermined period of collected SMBG data, for example about 4-6 weeks. In one embodiment, the invention provides a computerized method and system for evaluating the $HbA_{1c}$ of a patient based on BG data collected over a predetermined duration. The method (or system or computer useable medium) includes evaluating the $HbA_{1c}$ of a patient based on BG data collected over a first predetermined duration. The method comprising: preparing the data for estimating $HbA_{1c}$ using a predetermined sequence of mathematical formulas defined as: pre-processing of the data; estimating HbA1c using at least one of four predetermined formulas; and validation of the estimate via sample selection criteria.

Another aspect of the invention includes a method, system, and computer program product for estimating the long-term probability for severe hypoglycemia (SH). This method uses SMBG readings from a predetermined period, for example about 4-6 weeks, and predicts the risk of SH within the following approximate 6 months. In one embodiment, the invention provides a computerized method and system for evaluating the long term probability for severe hypoglycemia (SH) of a patient based on BG data collected over a predetermined duration. The method (or system or computer useable medium) includes evaluating the long term probability for severe hypoglycemia (SH) or moderate hypoglycemia (MH) of a patient based on BG data collected over a predetermined duration. The method comprising: computing LBGI based on the collected BG data; and estimating the number of future SH episodes using a predetermined mathematical formula based on the computed LBGI.

Still yet another aspect of the invention includes a method, system, and computer program product for identifying 24-hour periods (or other select periods) of increased risk of hypoglycemia. This is accomplished through the computation of the short-term risk of hypoglycemia using SMBG readings collected over the previous 24 hours. In one embodiment, the invention provides a computerized method and system for evaluating the short term risk for severe hypoglycemia (SH) of a patient based on BG data collected over a predetermined duration. The method (or system or computer useable medium) includes evaluating the short term probability for severe hypoglycemia (SH) of a patient based on BG data collected over a predetermined duration. The method comprising: computing scale values based on the collected BG data; and computing the low BG risk value (RLO) for each BG data.

An aspect of an embodiment of the present invention includes a method (or alternatively a computer program) for evaluating the $HbA_{1c}$ of a patient based on BG data collected over a first predetermined duration. The method includes preparing the data for estimating $HbA_{1c}$ using a predetermined sequence of mathematical formulas. The mathematical formulas defined as: pre-processing of the data; validation of a sample of the BG data via sample selection criteria; and estimating $HbA_{1c}$ if the sample is valid.

An aspect of an embodiment of the present invention includes a system for evaluating the $HbA_{1c}$ of a patient based on BG data collected over a first predetermined duration. The system included a database component operative to maintain a database identifying said BG data and a processor, wherein the processor is programmed to prepare the data for estimating $HbA_{1c}$ using a predetermined sequence of mathematical formulas. The mathematical formulas defined as: pre-process the data, validate a sample of the BG data via sample selection criteria, and estimate $HbA_{1c}$ if the sample is valid.

An aspect of an embodiment of the present invention includes a system for evaluating the $HbA_{1c}$ of a patient based on BG data collected over a first predetermined duration. The system comprising: a BG acquisition mechanism, which is configured to acquire BG data from the patient; a database component operative to maintain a database identifying said BG data; and a processor. The processor is programmed to prepare the data for estimating $HbA_{1c}$, using a predetermined sequence of mathematical formulas. The mathematical formulas defined as: pre-process the data; validate a sample of the BG data via sample selection criteria; and estimate $HbA_{1c}$ if the sample is valid.

An aspect of an embodiment of the present invention includes a method (or alternatively a computer program) for evaluating the $HbA_{1c}$ of a patient without the need for prior $HbA_{1c}$ information based on BG data collected over a first predetermined duration. The method includes preparing the data for estimating $HbA_{1c}$ using a predetermined sequence of mathematical formulas. The mathematical formulas defined as: pre-processing of the data; validation of a sample of the BG data via sample selection criteria; and estimating $HbA_{1c}$ if the sample is valid.

An aspect of an embodiment of the present invention includes a system for evaluating the $HbA_{1c}$ of a patient without the need for prior $HbA_{1c}$ information based on BG data collected over a first predetermined duration. The system includes a database component operative to maintain a database identifying the BG data and a processor. The processor being programmed to prepare the data for estimating $HbA_{1c}$ using a predetermined sequence of mathematical formulas. The mathematical formulas defined as: pre-process the data, validate a sample of the BG data via sample selection criteria, and estimate $HbA_{1c}$ if the sample is valid.

An aspect of an embodiment of the present invention includes a system for evaluating the $HbA_{1c}$ of a patient without the need for prior $HbA_{1c}$ information based on BG data collected over a first predetermined duration. The system comprising: a BG acquisition mechanism, which is configured to acquire BG data from the patient; a database component operative to maintain a database identifying said BG data; and a processor. The processor programmed to prepare the data for estimating $HbA_{1c}$ using a predetermined sequence of mathematical formulas. The mathematical formulas defined as: pre-process the data; validate a sample of the BG data via sample selection criteria; and estimate $HbA_{1c}$ if the sample is valid.

These aspects of the invention, as well as other aspects discussed throughout this document, can be integrated together to provide continuous information about the glycemic control of an individual with diabetes, and enhanced monitoring of the risk of hypoglycemia.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which:

FIG. 14 graphically presents the smoothed dependence between the hit rate and the ratio $R_{ud}$ expressed in percentage in Example No. 1.

FIG. 15 graphically presents the dependence between the prediction period and the corresponding hit rate in Example No. 1.

FIGS. 16(A)-(B) graphically present a one-month risk for significant hypoglycemia in T1DM predicted by the LBGI for ANOVA of number of severe hypoglycemic episodes by risk group ($F=7.2$, $p<0.001$) and ANOVA of number of moderate hypoglycemic episodes by risk group ($F=13.9$, $p<0.001$) in Example No. 2.

FIGS. 17(A)-(B) graphically present a 3-month risk for significant hypoglycemia in T1DM predicted by the LBGI for ANOVA of number of severe hypoglycemic episodes by risk group ($F=9.2$, $p<0.001$) and ANOVA of number of moderate hypoglycemic episodes by risk group ($F=14.7$, $p<0.001$) in Example No. 2.

FIGS. 19(A)-(B) graphically present a 3-month risk for significant hypoglycemia in T2DM predicted by the LBGI for ANOVA of number of severe hypoglycemic episodes by risk group ($F=5.3$, $p<0.01$) and ANOVA of number of moderate hypoglycemic episodes by risk group ($F=20.1$, $p<0.001$) in Example No. 2.

DETAILED DESCRIPTION OF THE INVENTION

Figure 1:
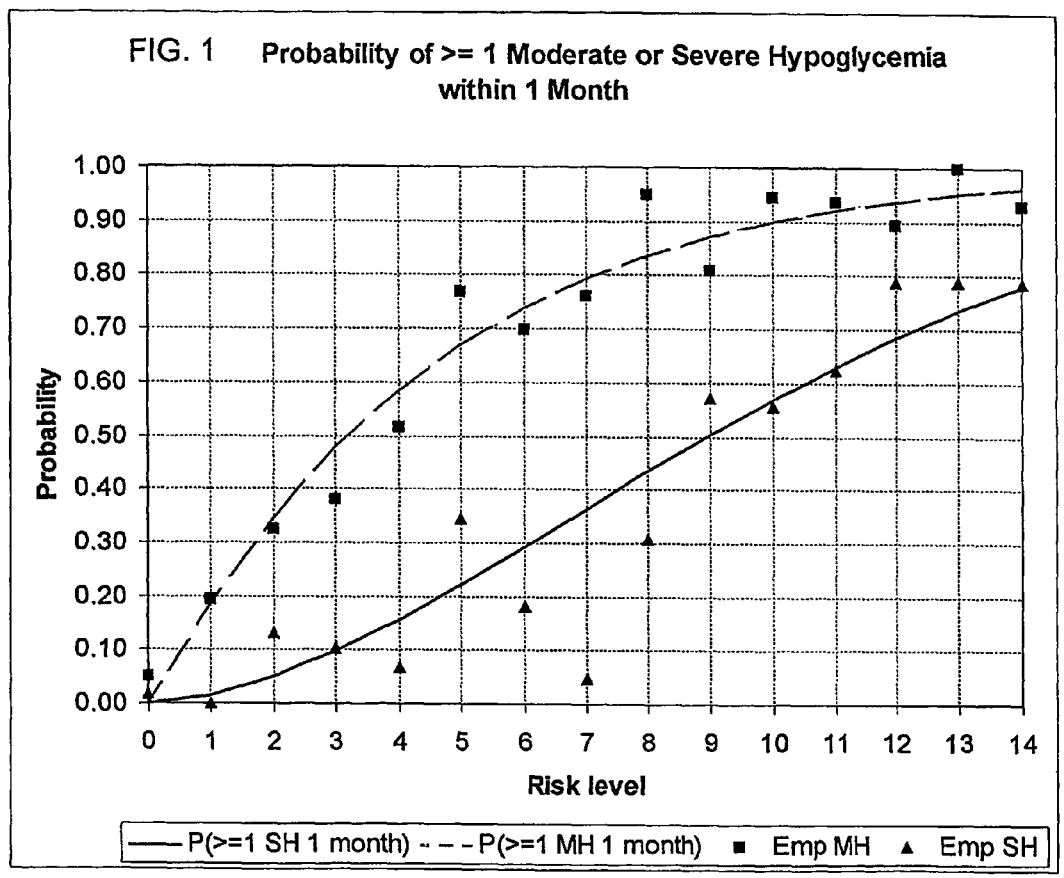
FIG. 1 graphically presents the empirical and theoretical probabilities for moderate (dashed line) and severe (black line) hypoglycemia within one month after the SMBG assessment for each of the 15 categories of risk level defined by the Low BG Index of Example No. 1.

The invention makes possible, but not limited thereto, the creation of precise methods for the evaluation of diabetics' glycemic control, and include, firmware and software code to be used in computing the key components of the method. The inventive methods for evaluating $HbA_{1c}$, the long-term probability of SH, and the short-term risk of hypoglycemia, are also validated based on the extensive data collected, as will be discussed later in this document. Finally, the aspects of these methods can be combined in structured display or matrix.

I. Evaluating $HbA_{1c}$

One aspect of the invention includes a method, system, and computer program product for evaluating $HbA_{1c}$ from a predetermined period of collected SMBG data, for example 4-6 weeks. In one embodiment, the invention provides a computerized (or other type) method and system for evaluating the $HbA_{1c}$ of a patient based on BG data collected over a predetermined duration. The method includes evaluating the $HbA_{1c}$ of a patient based on BG data collected over a first predetermined duration, the method comprising: preparing the data for estimating $HbA_{1c}$ using a predetermined sequence of mathematical formulas. The mathematical formulas defined as: pre-processing of the data; estimating $HbA_{1c}$ using at least one of four predetermined formulas; and validation of the estimate via sample selection criteria. The first predetermined duration can be about 60 days, or alternatively the first predetermined duration ranges from about 45 days to about 75 days, or from about 45 days to about 90 days, or as desired; The preprocessing of the data for each patient comprise: conversion of plasma to whole blood BG mg/dl; conversion of BG measured in mg/dl to units of mmol/l; and computing Low Blood Glucose Index (RLO1) and High Blood Glucose Index (RHI1). The preprocessing of the data for each patient uses a predetermined mathematical formulas defined as: conversion of plasma to whole blood BG mg/dl via BG=PLASBG (mg/dl)/1.12; conversion of BG measured in mg/dl to units of mmol/l) via BGMM=BG/18; and computing Low Blood Glucose Index (RLO1) and High Blood Glucose Index (RHI1). The preprocessing of the data further uses a predetermined mathematical formula defined as: Scale=[ln (BG)]$^{1.0845}$−5.381, wherein BG is measured in units of mg/dl; Risk1=22.765(Scale)$^2$, wherein RiskLO=Risk1 if (BG is less than about 112.5) and therefore risk of LBGI exists, otherwise RiskLO=0; RiskHI=Risk1 if(BG is greater than about 112.5) and therefore risk of HBGI exists, otherwise RiskHI=0; BGMM1=average of BGMM per patient; RLO1=average of RiskLO per patient; RHI1=average of RiskHI per patient; L06=average of RiskLO computed only for readings during the night, otherwise missing if there are no readings at night; N06, N12, N24 are percentage of SMBG readings in time intervals; NC1=total number of SMBG readings in the first predetermined duration; and NDAYS=number of days with SMBG readings in the first predetermined duration. The N06, N12, N24 are percentage of SMBG readings in time intervals of about 0-6:59 hour time period; about 7-12:59 hour time period, and about 18-23:59 hour time period, respectively, or other desired percentages and number of intervals.

The method further comprises assigning a group depending on the patient's computed High BG Index using a predetermined mathematical formula. This formula may be defined as: if (RHI1 is ≦about 5.25 or if RHI1 is ≧about 16) then the assigned group=0; if (RHI1 is >about 5.25 and if RHI1 is <about 7.0) then the assigned group=1; if (RHI1 is ≧about 7.0 and if RHI1 is <about 8.5) then the assign group=2; and if (RHI1 is ≧about 8.5 and if RHI1 is <about 16) then the assigned group=3.

Next, the method may further include providing estimates using a predetermined mathematical formula defined as: E0=0.55555*BGMM1+2.95; E1=0.50567*BGMM1+0.074*L06+2.69; E2=0.55555*BGMM1−0.074*L06+2.96; E3=0.44000*BGMM1+0.035*L06+3.65; and if (Group=1) then EST2=E1, or if (Group=2) then EST2=E2, or if (Group=3) then EST2=E3, otherwise EST2=E0.

The method comprise providing further correction of the estimates using a predetermined mathematical formula defined as: if (missing(L06)) EST2=E0, if (RLO1 is ≦about 0.5 and RHI1 is ≦about 2.0) then EST2=E0−0.25; if (RLO1 is ≦about 2.5 and RHI1 is >about 26) then EST2=E0−1.5*RLO1; and if ((RLO1/RHI1) is ≦about 0.25 and L06 is >about 1.3) then EST2=EST2−0.08.

The estimation of the $HbA_{1c}$ of a patient based on BG data collected over the first predetermined duration can be accomplished by estimating $HbA_{1c}$ using at least one of four predetermined mathematical formulas defined as:
  a) HbA1c=the EST2 defined above or as corrected above;
  b) $HbA_{1c}$=0.809098*BGMM1+0.064540*RLO1−0.151673*RHI1+1.873325, wherein BGMM1 is the average BG (mmol/l), RLO1 is the Low BG Index, RHI1 is the High BG Index;
  c) HbA1c=0.682742*HBA0+0.054377*RHI1+1.553277, wherein HBA0 is a previous reference HbA1c reading taken about a second predetermined period prior to the estimate, wherein RHI1=is the High BG Index; or
  d) HbA1c=0.41046*BGMM+4.0775 wherein BGMM1 is the average BG (mmol/l). The second predetermined duration can be about three months; about 2.5 months to about 3.5 months; or about 2.5 months to six months, or as desired.

The validation of the estimate using sample selection criteria of HbA1c estimate is achieved only if the first predetermined duration sample meets at least one of the following four criteria:
  a) a test frequency criterion wherein if the first predetermined duration sample contains an average of at least about 1.5 to about 2.5 tests per day; b) an alternative test frequency criterion only if the predetermined duration sample contains at least a third predetermined sample period with readings with an average frequency of about 1.8 readings/day (or other desired average frequency);
  c) a randomness of data criterion-1 wherein the HbA1c estimate is validated or displayed only if the ratio (RLO1/RHI1>=about 0.005), wherein: RLO1 is the Low BG Index, RHI1 is the High BG Index; or
  d) a randomness of data criterion wherein HbA1c estimate is validated or displayed only if the ratio (NO6>=about 3%), and wherein N06 is the percentage of readings during the night. The third predetermined duration can be at least 35 days, range from about 35 days to about 40 days, or from about 35 days to about as long as the first predetermined duration, or as desired.

II. Long-Term Probability for Severe Hypoglycemia (SH).

Another aspect of the invention includes a method, system, and computer program product for estimating the long-term probability for severe hypoglycemia (SH). This method uses SMBG readings from a predetermined period, for example about 4-6 weeks, and predicts the risk of SH within the following approximate 6 months. In one embodiment, the invention provides a computerized method (or other type) and system for evaluating the long term probability for severe hypoglycemia (SH) of a patient based on BG data collected over a predetermined duration. The method for evaluating the long term probability for severe hypoglycemia (SH) or moderate hypoglycemia (WI) of a patient based on BG data collected over a predetermined duration comprises: computing LBGI based on the collected BG data; and estimating the number of future SH episodes using a predetermined mathematical formula based on the computed LBGI. The computed LBGI is mathematically defined from a series of BG readings $x_1, x_2, \ldots x_n$ taken at time points $t_1, t_2, \ldots, t_n$ as:

$$LBGI = \frac{1}{n}\sum_{i=1}^{n} lbgi(x_i; 2),$$

where: $lbgi(BG; a) = 10 \cdot f(BG)^a$ if $f(BG) > 0$ and 0 otherwise, and a=about 2, representing a weighting parameter (or other weighting parameter as desire).

A predetermined risk categories(RCAT) is defined, whereby each of the risk categories(RCAT) represent a range of values for LBGI; and the LBGI is assigned to at least one of said risk categories(RCAT). The risk categories(RCAT) are defined as follows:
  category 1, wherein said LBGI is less than about 0.25;
  category 2, wherein said LBGI is between about 0.25 and about 0.50;
  category 3, wherein said LBGI is between about 0.50 and about 0.75;
  category 4, wherein said LBGI is between about 0.75 and about 1.0;
  category 5, wherein said LBGI is between about 1.0 and about 1.25;
  category 6; wherein said LBGI is between about 1.25 and about 1.50;
  category 7, wherein said LBGI is between about 1.5 and about 1.75;
  category 8, wherein said LBGI is between about 1.75 and about 2.0;
  category 9, wherein said LBGI is between about 2.0 and about 2.5;
  category 10, wherein said LBGI is between about 2.5 and about 3.0
  category 11, wherein said LBGI is between about 3.0 and about 3.5;
  category 12, wherein said LBGI is between about 3.5 and about 4.25;
  category 13, wherein said LBGI is between about 4.25 and about 5.0;
  category 14, wherein said LBGI is between about 5.0 and about 6.5; and
  category 15, wherein said LBGI is above about 6.5.

Next, the probability of incurring a select number of SH episodes is defined respectively for each of said assigned risk categories(RCAT). Defining a probability of incurring a select number of SH episodes within a next first predetermined duration respectively for each of said assigned risk categories(RCAT), using the formula: $F(x)=1-\exp(-a \cdot x^b)$ for any x>0 and 0 otherwise, wherein: a=about −4.19 and b=about 1.75 (a and/or b may be other desired values). The first predetermined duration can be about one month; range from about 0.5 months to about 1.5 months, or ranges from about 0.5 months to about 3 months, or as desired.

Also, the probability of incurring a select number of SH episodes within a next second predetermined duration respectively for each of said assigned risk categories(RCAT) is defined, using the formula: $F(x)=1-\exp(-a.x^b)$ for any x>0 and 0 otherwise, wherein: a=about −3.28 and b=about 1.50 (a and/or b may be other desired values). The second predetermined duration can be about three months, range from about 2 months to about 4 months, or about 3 months to about 6 months, or as desired.

Further, a probability of incurring a select number of SH episodes within the next third predetermined duration is defined respectively for each of the assigned risk categories (RCAT), using the formula: $F(x)=1-\exp(-a.x^b)$ for any x>0 and 0 otherwise, wherein: a=about −3.06 and b=about 1.45 (a and/or b may be other desired values). The third predetermined duration can be about 6 months, range from about 5 months to about 7 months, or range from about 3 months to about 9 months, or as desired.

Alternatively, a probability of incurring a select number of MH episodes within the next first predetermined period (ranges of about 1 month, about 0.5-1.5 months, about 0.5-3 months, or as desired) is defined respectively for each of said assigned risk categories(RCAT), using the formula: $F(x)=1-\exp(-a.x^b)$ for any x>0 and 0 otherwise, wherein: a=about −1.58 and b=about 1.05 (a and/or b may be other desired values).

Alternatively, a probability of incurring a select number of MH episodes within the next second predetermined period (ranges of about 3 months, about 2-4 months, about 3-6 months, or as desired) is defined respectively for each of said assigned risk categories(RCAT), using the formula: $F(x)=1-\exp(-a.x^b)$ for any x>0 and 0 otherwise, wherein: a=about −1.37 and b=about 1.14 (a and/or b may be other desired values).

Alternatively, a probability of incurring a select number of MH episodes within the next third predetermined period (ranges of about 6 months, about 5-7 months, about 3-9 months, or as desired) is defined respectively for each of said assigned risk categories(RCAT), using the formula: $F(x)=1-\exp(-a.x^b)$ for any x>0 and 0 otherwise, wherein: a=about −1.37 and b=about 1.35 (a and/or b may be other desired values).

Moreover, classifications of risk for future significant hypoglycemia of the patient are assigned. The classifications are defined as follows: minimal risk, wherein said LBGI is less than about 1.25; low risk, wherein said LBGI is between about 1.25 and about 2.50; moderate risk, wherein said LBGI is between about 2.5 and about 5; and high risk, wherein said LBGI is above about 5.0 (other classification ranges can be implemented as desired).

III. Short-term Probability for Severe Hypoglycemia (SH).

Still yet another aspect of the invention includes a method, system, and computer program product for identifying 24-hour periods (or other select periods) of increased risk of hypoglycemia. This is accomplished through the computation of the short-term risk of hypoglycemia using SMBG readings collected over the previous 24 hours. In one embodiment, the invention provides a computerized method and system for evaluating the short term risk for severe hypoglycemia (SH) of a patient based on BG data collected over a predetermined duration. The method for evaluating the short term probability for severe hypoglycemia (SH) of a patient based on BG data collected over a predetermined duration comprises: computing scale values based on said collected BG data; and computing the low BG risk value (RLO) for each BG data. The computed RLO(BG) is mathematically defined as: Scale=$[\ln(BG)]^{1.0845}-5.381$, wherein BG is measured in units of mg/dl; Risk=$22.765(Scale)^2$; if (BG is less than about 112.5) then: RLO(BG)=Risk, otherwise RLO (BG)=0. Alternatively, the computed RLO(BG) is mathematically defined as: Scale=$[\ln(BG)]^{1.026}-1.861$, wherein BG is measured in units of mmol/l; Risk=$32.184(Scale)^2$; if (BG is≦about 112.5) then: RLO(BG)=Risk, otherwise RLO (BG)=0.

LBGI can be computed based on the collected BG data. The computed LBGI is mathematically defined from a series of BG readings $x_1, x_2, \ldots x_n$ taken at time points $$t_1, t_2, \ldots, t_n \text{ as: } LBGI = \frac{1}{n}\sum_{i=1}^{n} lbgi(x_i; 2),$$

where: $lbgi(BG; a) = RLO(BG)$.

Provisional LBGI can be computed based on the collected BG data. The computed provisional LBGI is mathematically defined from mathematically defined as: LBGI(1)=RLO($x_1$); RLO2(1)=0; LBGI(j)=((j−1)/j)*LBGI(j−1)+(1/j)*RLO($x_j$); and RLO2(j)=((j−1)/j)*RLO2(j−1)+(1/j)*(RLO($x_j$)−LBGI (j))$^2$.

SBGI can be computed using a mathematical formula defined as: SBGI(n)=$\sqrt{(RLO2(n))}$.

Next, the invention provides a qualification or warning of upcoming short term SH. The qualification or warning is provided if: (LBGI(150)≧2.5 and LBGI(50)≧(1.5*LBGI (150) and SBGI(50)≧SBGI(150)) then said issue of warning is qualified or provided, or RLO≧(LBGI(150)+1.5*SBGI (150)) then said issue of warning is qualified or provided, otherwise, a warning is not necessarily qualified or provided.

Alternatively, Next, the invention provides a qualification or warning of upcoming short term SH. The qualification or warning is provided if:
(LBGI(n)≧α and SBGI(n) ge (β)) then said issue of warning is qualified or provided, and/or (RLO(n)≧(LBGI(n)+γ*SBGI (n))) then said issue of warning is qualified or provided; otherwise a warning is not necessarily qualified or provided, wherein α, β, and γ are threshold parameters.

The threshold parameters α, β, and γ are defined as α=about 5, β=about 7.5, γ=about 1.5. Other possible parameter combinations are presented in the table below. The values may be approximations of the values presented below as well as any intermediate combination of values in the table below.

| α | β | γ |
|---|---|---|
| 6.4 | 8.2 | 1.5 |
| 6.0 | 7.5 | 1.5 |
| 5.5 | 7.5 | 1.5 |
| 5.0 | 7.5 | 1.3 |
| 4.9 | 7.0 | 1.2 |
| 4.8 | 7.0 | 1.2 |

IV. Exemplary Systems

Figure 6:
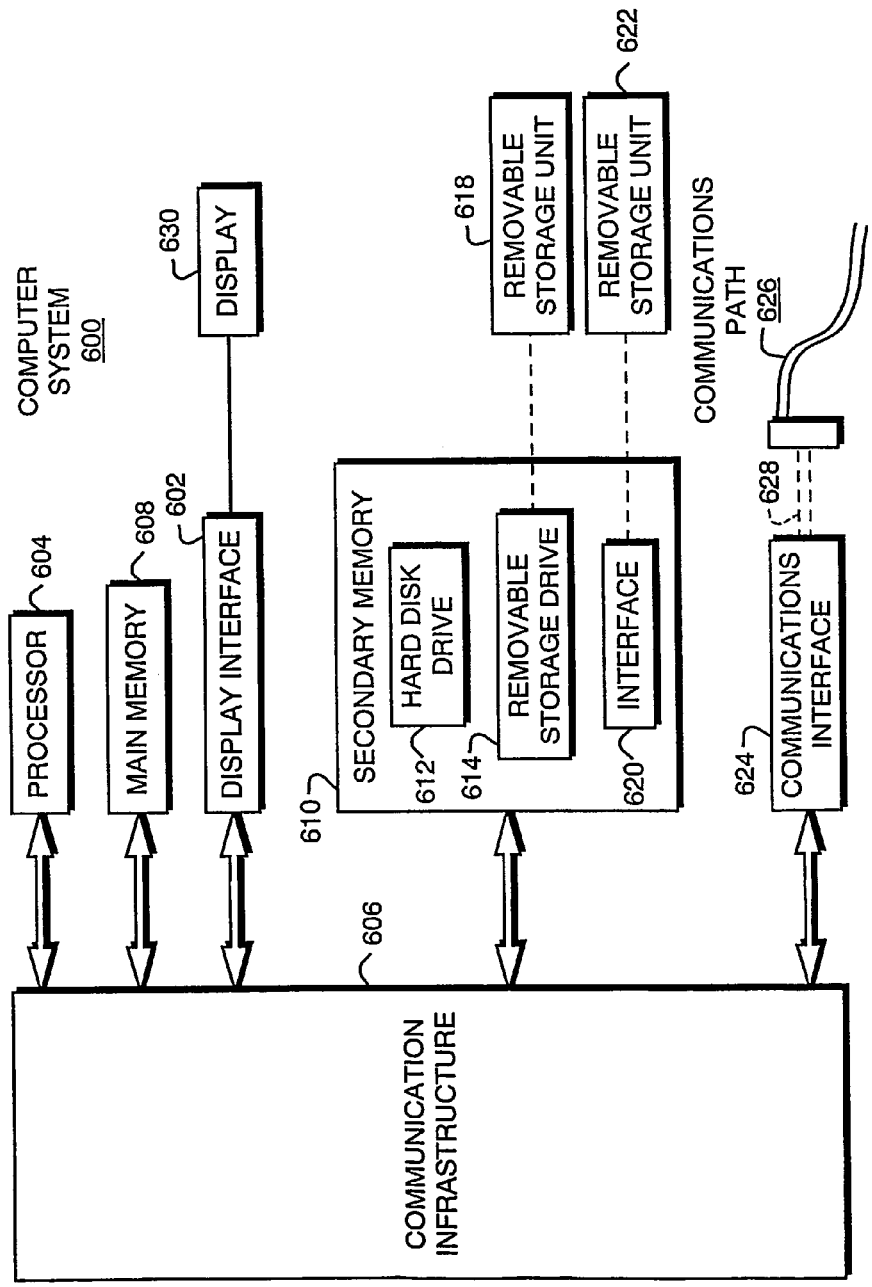
FIG. 6 is a functional block diagram for a computer system for implementation of the present invention.

The method of the invention may be implemented using hardware, software or a combination thereof and may be implemented in one or more computer systems or other processing systems, such as personal digit assistants (PDAs), or directly in blood glucose self-monitoring devices (SMBG memory meters) equipped with adequate memory and processing capabilities. In an example embodiment, the invention was implemented in software running on a general purpose computer 900 as illustrated in FIG. 6. Computer system 600 includes one or more processors, such as processor 604 Processor 604 is connected to a communication infrastructure 606 (e.g., a communications bus, cross-over bar, or network). Computer system 600 may include a display interface 602 that forwards graphics, text, and other data from the communication infrastructure 606 (or from a frame buffer not shown) for display on the display unit 630.

Computer system 600 also includes a main memory 608, preferably random access memory (RAM), and may also include a secondary memory 610. The secondary memory 610 may include, for example, a hard disk drive 612 and/or a removable storage drive 614, representing a floppy disk drive, a magnetic tape drive, an optical disk drive, a flash memory, etc. The removable storage drive 614 reads from and/or writes to a removable storage unit 618 in a well known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other means for allowing computer programs or other instructions to be loaded into computer system 600. Such means may include, for example, a removable storage unit 622 and an interface 620. Examples of such removable storage units/interfaces include a program cartridge and cartridge interface (such as that found in video game devices), a removable memory chip (such as a ROM, PROM, EPROM or EEPROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between computer system 600 and external devices. Examples of communications interface 624 may include a modem, a network interface (such as an Ethernet card), a communications port (e.g., serial or parallel, etc.), a PCMCIA slot and card, a modem, etc. Software and data transferred via communications interface 624 are in the form of signals 628 which may be electronic, electromagnetic, optical or other signals capable of being received by communications interface 624. Signals 628 are provided to communications interface 624 via a communications path (i.e., channel) 626. Channel 626 carries signals 628 and may be implemented using wire or cable, fiber optics, a phone line, a cellular phone link, an RF link, an infrared link, and other communications channels.

In this document, the terms "computer program medium" and "computer usable medium" are used to generally refer to media such as removable storage drive 614, a hard disk installed in hard disk drive 612, and signals 628. These computer program products are means for providing software to computer system 600. The invention includes such computer program products.

Computer programs (also called computer control logic) are stored in main memory 608 and/or secondary memory 610. Computer programs may also be received via communications interface 624. Such computer programs, when executed, enable computer system 600 to perform the features of the present invention as discussed herein. In particular, the computer programs, when executed, enable processor 604 to perform the functions of the present invention. Accordingly, such computer programs represent controllers of computer system 600.

In an embodiment where the invention is implemented using software, the software may be stored in a computer program product and loaded into computer system 600 using removable storage drive 614, hard drive 612 or communications interface 624. The control logic (software), when executed by the processor 604, causes the processor 604 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in SPSS control language, but could be implemented in other programs such as, but not limited to, C++ programming language or other programs available to those skilled in the art.

Figure 7:
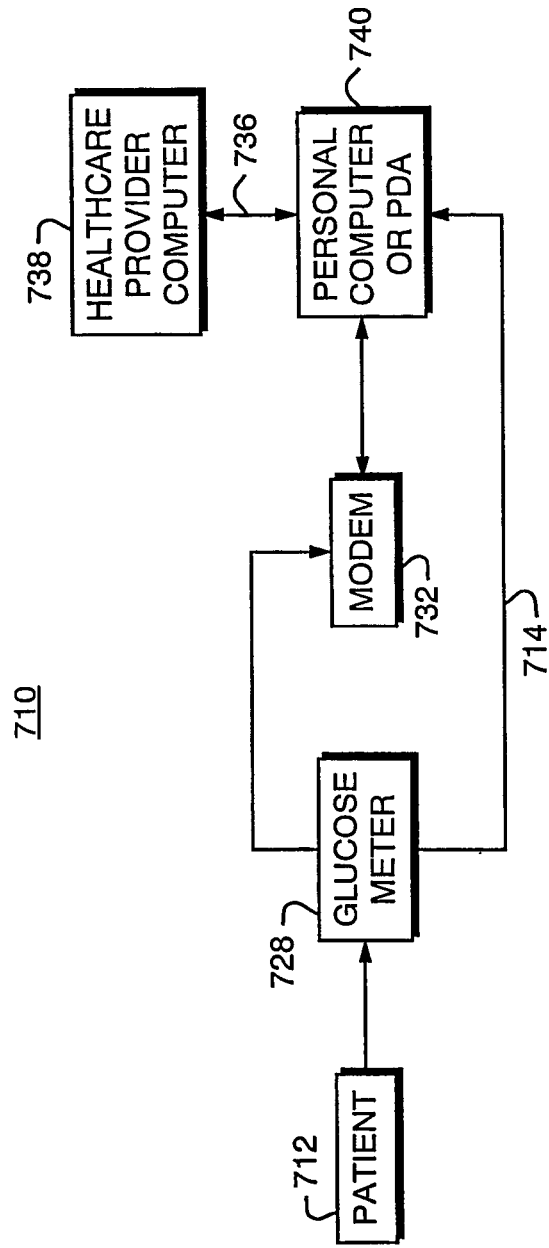
FIGS. 7-9 are schematic block diagrams of alternative variations of the present invention related processors, communication links, and systems.
Figure 8:
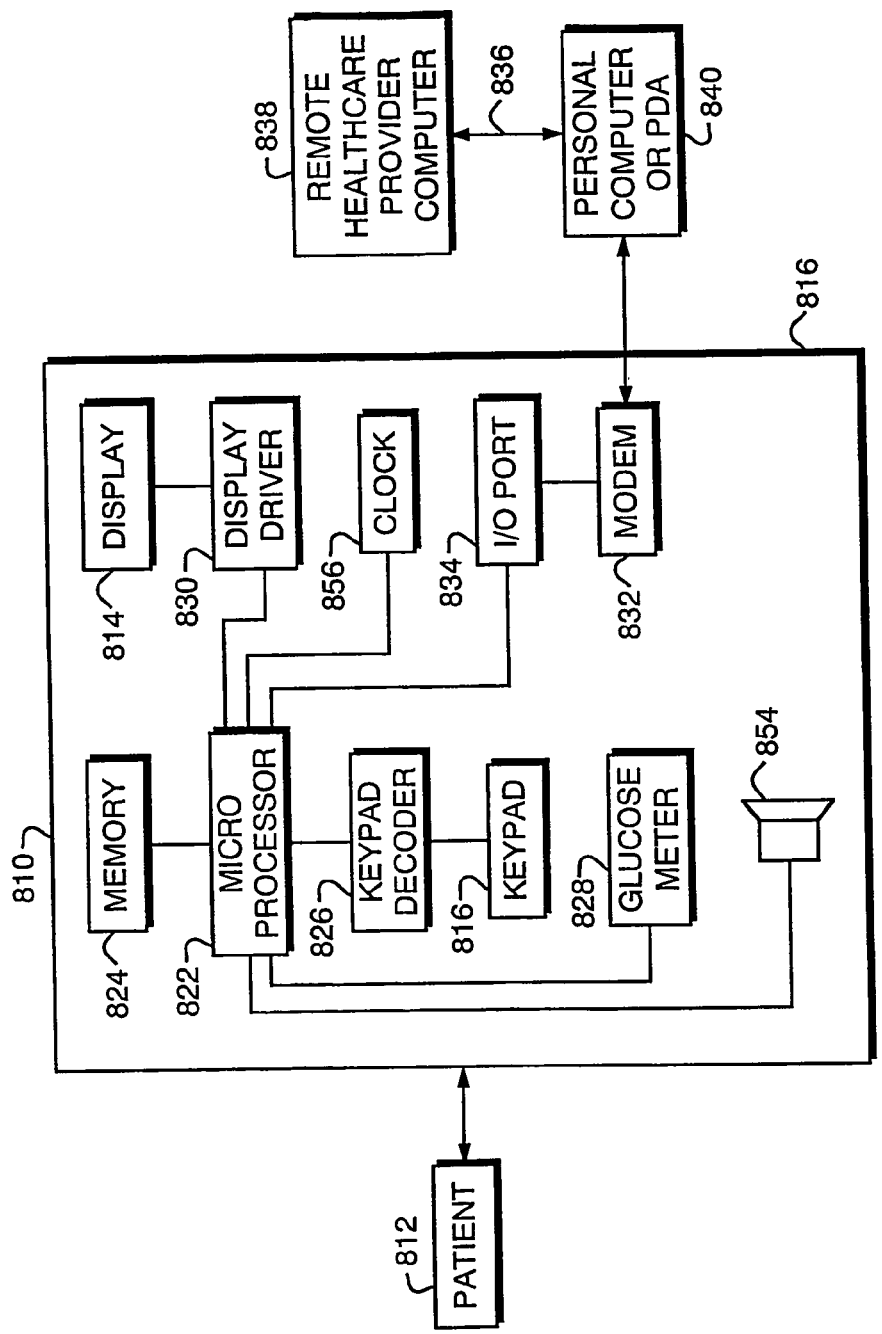
Figure 9:
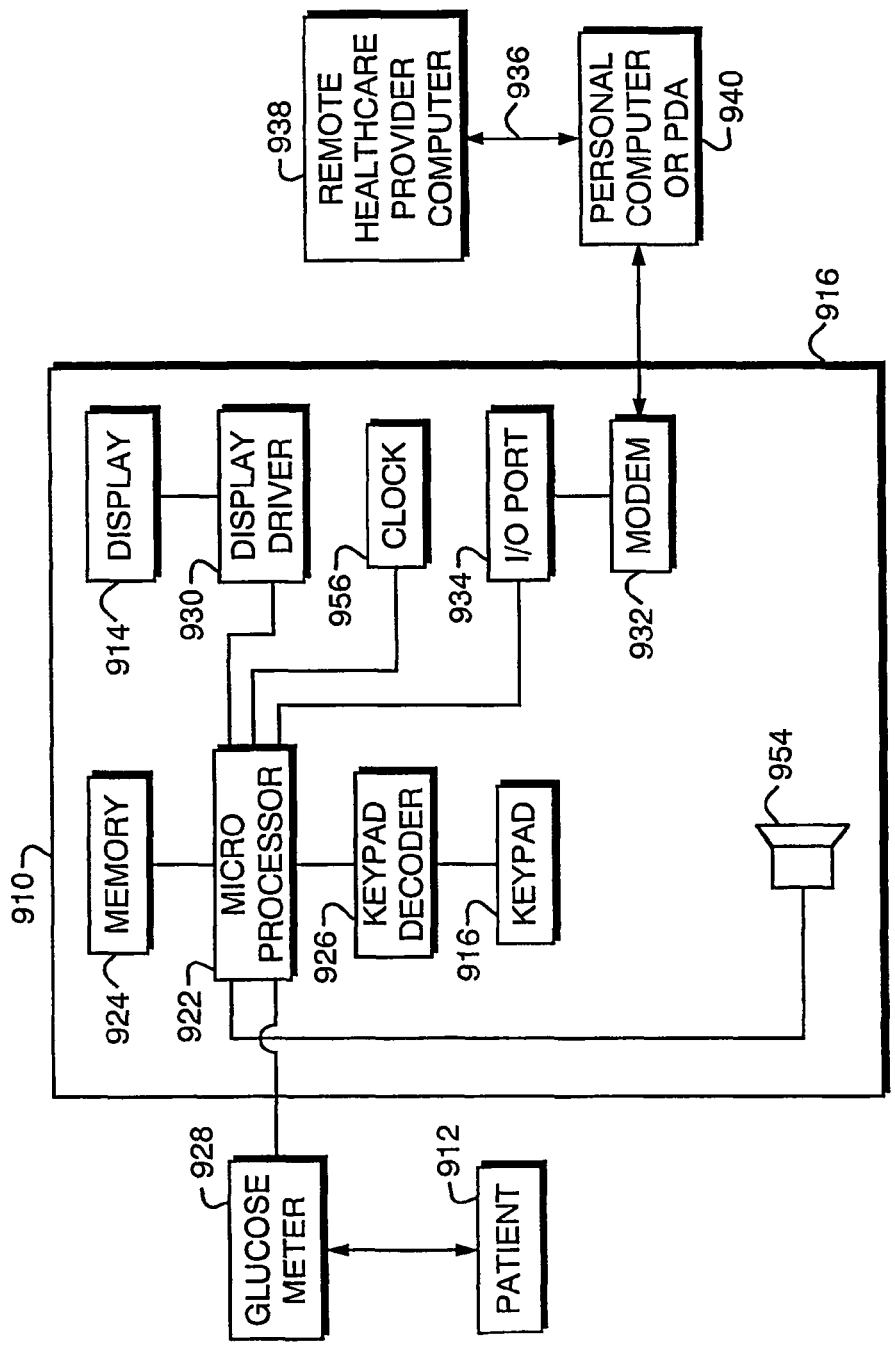

FIGS. 7-9 show block diagrammatic representation of alternative embodiments of the invention. Referring FIG. 7, there is shown a block diagrammatic representation of the system 710 essentially comprises the glucose meter 728 used by a patient 712 for recording, inter alia, insulin dosage readings and measured blood glucose ("BG") levels, Data obtained by the glucose meter 728 is preferably transferred through appropriate communication links 714 or data modem 732 to a processing station or chip, such as a personal computer 740, PDA, or cellular telephone, or via appropriate Internet portal. For instance, data stored may be stored within the glucose meter 728 and may be directly downloaded into the personal computer 740 through an appropriate interface cable and then transmitted via the Internet to a processing location. An example is the ONE TOUCH monitoring system or meter by LifeScan, Inc. which is compatible with IN TOUCH software which includes an interface cable to down load the data to a personal computer.

The glucose meter is common in the industry and includes essentially any device that can functions as a BG acquisition mechanism. The BG meter or acquisition mechanism, device, tool, or system includes various conventional methods directed toward drawing a blood sample (e.g. by fingerprick) for each test, and a determination of the glucose level using an instrument that reads glucose concentrations by electromechanical or claorimetric methods. Recently, various methods for determining the concentration of blood analytes without drawing blood have been developed. For example, U.S. Pat. No. 5,267,152 to Yang et al. (hereby incorporated by reference) describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. (of which are hereby incorporated by reference).

U.S. Pat. No. 5,139,023 to Stanley (hereby incorporated by reference) describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich (hereby incorporated by reference) describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder (of which are hereby incorporated by reference).

In addition, U.S. Pat. No. 5,279,543 to Glikfeld (hereby incorporated by reference) describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Moreover, International Publication No. WO 96/00110 to Tamada (hereby incorporated by reference) describes an iontophoretic apparatus for transdermal monitoring of a target substance, wherein an iontophoretic electrode is used to move an analyte into a collection reservoir and a biosensor is used to detect the target analyte present in the reservoir. Finally, U.S. Pat. No. 6,144,869 to Berner (hereby incorporated by reference) describes a sampling system for measuring the concentration of an analyte present.

Further yet, the BG meter or acquisition mechanism may include indwelling catheters and subcutaneous tissue fluid sampling.

The computer or PDA 740 includes the software and hardware necessary to process, analyze and interpret the self-recorded diabetes patient data in accordance with predefined flow sequences (as described above in detail) and generate an appropriate data interpretation output. Preferably, the results of the data analysis and interpretation performed upon the stored patient data by the computer 740 are displayed in the form of a paper report generated through a printer associated with the personal computer 740. Alternatively, the results of the data interpretation procedure may be directly displayed on a video display unit associated with the computer 740.

FIG. 8 shows a block diagrammatic representation of an alternative embodiment having a diabetes management system that is a patient-operated apparatus 810 having a housing preferably sufficiently compact to enable apparatus 810 to be hand-held and carried by a patient. A strip guide for receiving a blood glucose test strip (not shown) is located on a surface of housing 816. Test strip is for receiving a blood sample from the patient 812. The apparatus includes a microprocessor 822 and a memory 824 connected to microprocessor 822. Microprocessor 822 is designed to execute a computer program stored in memory 824 to perform the various calculations and control functions as discussed in great detail above. A keypad 816 is connected to microprocessor 822 through a standard keypad decoder 826. Display 814 is connected to microprocessor 822 through a display driver 830. Microprocessor 822 communicates with display driver 830 via an interface, and display driver 830 updates and refreshes display 814 under the control of microprocessor 822. Speaker 854 and a clock 856 are also connected to microprocessor 822. Speaker 854 operates under the control of microprocessor 822 to emit audible tones alerting the patient to possible future hypoglycemia. Clock 856 supplies the current date and time to microprocessor 822.

Memory 824 also stores blood glucose values of the patient 812, the insulin dose values, the insulin types, and the parameter values used by microprocessor 822 to calculate future blood glucose values, supplemental insulin doses, and carbohydrate supplements. Each blood glucose value and insulin dose value is stored in memory 824 with a corresponding date and time. Memory 824 is preferably a non-volatile memory, such as an electrically erasable read only memory (EEPROM).

Apparatus 810 also includes a blood glucose meter 828 connected to microprocessor 822. Glucose meter 828 is designed to measure blood samples received on blood glucose test strips and to produce blood glucose values from measurements of the blood samples. As mentioned previously, such glucose meters are well known in the art. Glucose meter 828 is preferably of the type which produces digital values which are output directly to microprocessor 822. Alternatively, blood glucose meter 828 may be of the type which produces analog values. In this alternative embodiment, blood glucose meter 828 is connected to microprocessor 822 through an analog to digital converter (not shown).

Apparatus 810 further includes an input/output port 834, preferably a serial port, which is connected to microprocessor 822. Port 834 is connected to a modem 832 by an interface, preferably a standard RS232 interface. Modem 832 is for establishing a communication link between apparatus 810 and a personal computer 840 or a healthcare provider computer 838 through a communication network 836. Specific techniques for connecting electronic devices through connection cords are well known in the art. Another alternative example is "bluetooth" technology communication.

Alternatively, FIG. 9 shows a block diagrammatic representation of an alternative embodiment having a diabetes management system that is a patient-operated apparatus 910, similar as shown in FIG. 8, having a housing preferably sufficiently compact to enable the apparatus 910 to be hand-held and carried by a patient. For example, a separate or detachable glucose meter or BG acquisition mechanism/module 928. There are already self-monitoring devices that are capable of directly computing Algorithms 1, 2, 3 and displaying the results to the patient without transmitting the data to anything else. Examples of such devices are ULTRA SMART fa self-monitoring device capable of directly computing Algorithms 1, 2, 3 and displaying the results to a patient) by Lifescan Inc., Milpitas, Calif. and FREESTYLE TRACKER fa self-monitoring device capable of directly computing Algorithms 1, 2, 3 and displaying the results to a patient) by Therasense, Alameda, Calif.

Accordingly, the embodiments described herein are capable of being implemented over data communication networks such as the internet, making evaluations, estimates, and information accessible to any processor or computer at any remote location, as depicted in FIGS. 6-9 and/or U.S. Pat. No. 5,851,186 to Wood, of which is hereby incorporated by reference herein. Alternatively, patients located at remote locations may have the BG data transmitted to a central healthcare provider or residence, or a different remote location.

In summary, the invention proposes a data analysis computerized (or non-computerized) method and system for the simultaneous evaluation of the two most important components of glycemic control in individuals with diabetes: HbA1c and the risk of hypoglycemia. The method, while using only routine SMBG data, provides, among other things, three sets of output.

The potential implementations of the method, system, and computer program product of the invention is that it provides the following advantages, but are not limited thereto. First, the invention enhances existing home BG monitoring devices by producing and displaying: 1) estimated categories for HbA1c, 2) estimated probability for SH in the subsequent six months, and 3) estimated short-term risk of hypoglycemia (i.e. for the next 24 hours). The latter may include warnings, such as an alarm, that indicates imminent hypoglycemic episodes. These three components can also be integrated to provide continuous information about the glycemic control of individuals with diabetes, and to enhance the monitoring of their risk of hypoglycemia.

As an additional advantage, the invention enhances existing software or hardware that retrieves SMBG data. Such software or hardware is produced by virtually every manufacturer of home BG monitoring devices and is customarily used by patients and health care providers to interpret SMBG data. The methods and system of the invention can be directly incorporated into existing home blood glucose monitors, or used for the enhancement of software that retrieves SMBG data, by introducing a data interpretation component capable of predicting both HbA1c and periods of increased risk of hypoglycemia.

Still yet another advantage, the invention evaluates the accuracy of home BG monitoring devices, both in the low and high BG ranges, and over the entire BG scale.

Moreover, another advantage, the invention evaluates the effectiveness of various treatments for diabetes.

Further still, as patients with diabetes face a life-long optimization problem of maintaining strict glycemic control without increasing their risk of hypoglycemia, the present invention alleviates this related problem by use of its simple and reliable methods, i.e., the invention is capable of evaluating both patients' glycemic control and their risk of hypoglycemia, and at the same time applying it in their everyday environments.

Additionally, the invention provides the missing link by proposing three distinct, but compatible, algorithms for evaluating HbA1c and the risk of hypoglycemia from SMBG data, to be used to predict the short-term and long-term risks of hypoglycemia, and the long-term risk of hyperglycemia.

Another advantage, the invention evaluates the effectiveness of new insulin or insulin delivery devices. Any manufacturer or researcher of insulin or insulin delivery devices can utilize the embodiments of the invention to test the relative success of proposed or tested insulin types or device delivery designs.

Finally, another advantage, the invention evaluates the effectiveness of drugs that are adjunct to insulin therapy.

EXAMPLES OF INVENTION

I. Example No. 1

This Example No. 1 consists of three algorithms for simultaneous evaluation, from routine SMBG data, of the two most important components of glycemic control in diabetes, $HbA_{1c}$ and risk for hypoglycemia. This method pertains directly to enhancement of existing home BG monitoring devices by introducing an intelligent data interpretation component capable of predicting both $HbA_{1c}$ and periods of increased risk for hypoglycemia. The data analysis method has three components (algorithms):

Algorithm 1: Evaluation of $HbA_{1c}$;
Algorithm 2: Evaluation of long-term risk for severe hypoglycemia (SH), and
Algorithm 3: Evaluation of short-term (within 24-48 hours) risk for hypoglycemia.

Algorithm 1 and 2 provide uninterrupted monitoring and information about the overall glycemic control of an individual with Type 1 or Type 2 diabetes mellitus (T1DM, T2DM), covering both the high and the low end of the BG scale. Algorithm 3 is supposed to be activated when Algorithm 2 indicates an increased long-term risk for hypoglycemia. Upon activation, Algorithm 3 requires more frequent monitoring (4 times a day) and provides 24 to 48-hour forecast of the risk for moderate/severe hypoglycemia.

Another important objective of Example 1 was to test with existing data a number of hypotheses and ideas that could potentially lead to alternative algorithms estimating $HbA_{1c}$ and computing risk for hypoglycemia in a manner that is conceptually different from the one proposed in the invention disclosure. The goal was to find potentially better solutions, or simply to verify that certain ideas do not lead to better results, which is essential for optimization and promptness of the analysis of the data that are currently being collected in Example No. 2 of the study.

Data Sets

In order to ensure that the results of our optimization can be generalized to population level, Algorithms 1 and 2 were first optimized using training data sets and then tested for accuracy using an unrelated test data set. For Algorithm 3 we currently have only one data set containing parallel SMBG and records of SH. A detailed description of the patient population follows:

(1) Training Data set 1: Ninety-six patients with T1DM, who were diagnosed at least 2 years prior to the study. Forty-three of these patients reported at least two episodes of severe hypoglycemia in the past year and 53 patients reported no such episodes during the same period. There were 38 males and 58 females. The mean age was 35±8 yr., mean duration of disease 16±10 yr., mean insulin units/kg per day 0.58±0.19, and mean $HbA_{1c}$ was 8.6±1.8%. These subjects collected approximately 13,000 SMBG readings over 40-45-day period. The frequency of SMBG was approximately 3 reading/day. This data collection was followed by 6 months of monthly diaries of moderate and severe hypoglycemic episodes. This data set was used as a training data set for Algorithm 1 (no prior $HbA_{1c}$) and for Algorithm 2.

(2) Training Data set: Eighty-five patients with T1DM, diagnosed at least 2 years prior to the study, all of whom reported SH episodes in the past year. There were 44 males and 41 females. The mean age was 44±10 years, mean duration of disease 26±11 yr., mean insulin units/kg per day 0.6±0.2, the mean baseline $HbA_{1c}$ was 7.7±1.1%, and the mean 6-month $HbA_{1c}$ was 7.4±1% (6-month $HbA_{1c}$ available for 60 subjects). These subjects collected approximately 75,500 SMBG readings during the 6 months between the two $HbA_{1c}$ assays. The frequency of SMBG in Data set 2 was higher—4-5 readings per day. In addition, during the 6 months of SMBG the subjects kept diaries of moderate and severe hypoglycemic episodes by date and time of their occurrence, resulting in 399 SH episodes. This data set was used as a training data set for Algorithm 1 (with prior $HbA_{1c}$) and for all analyses concerning Algorithm 3.

(3) The Test Data Set that we used contains data for N=600 subjects, 277 with T1DM and 323 with T2DM, all of whom used insulin to manage their diabetes. These data were collected by Amylin Pharmaceuticals, San Diego, Calif. and included 6-8 months of SMBG data (approximately 300,000 readings), accompanied by baseline and 6-month $HbA_{1c}$ determinations and some demographic data. These subjects were participating in a clinical trial investigating the effects of pramlintide (in doses of 60 to 120 micrograms) on metabolic control. The subjects' use pramlintide was randomized across the T1DM and T2DM groups (Table 1).

TABLE 1

Demographic characteristics of the subjects in the Test Data Set.

| Variable | T1DM - Mean(SD) | T2DM - Mean(SD) | p-level |
|---|---|---|---|
| Age (years) | 38.0 (13.4) | 58.1 (9.4) | <0.001 |
| Gender: Male/Female | 136/141 | 157/166 | Ns |
| Baseline $HbA_{1c}$ | 9.74 (1.3) | 9.85 (1.3) | Ns |
| $HbA_{1c}$ at month 6 | 8.77 (1.1) | 8.98 (1.3) | 0.04 |
| Duration of diabetes (years) | 14.6 (9.8) | 13.5 (7.6) | Ns |
| Age at onset (years) | 23.4 (12.8) | 44.6 (10.4) | <0.001 |
| # SMBG readings/subject/day | 3.2 (1.1) | 2.9 (0.9) | <0.005 |

Table 1 presents demographic characteristics and comparison of T1DM vs. T2DM subjects. For the first 6 months of the study the average $HbA_{1c}$ declined significantly in both T1DM and T2 DM groups, perhaps due to the use of medication, which is out of the scope of this presentation (Table 1). This relatively rapid change in $HbA_{1c}$ allowed for a better estimation of the predictive ability of Algorithm 1. In all data sets SMBG was performed using Lifescan ONE TOUCH II or ONE TOUCH PROFILE meters.

Algorithm 1: Evaluation of $HbA_{1c}$

Example No. 1 provides for, but not limited thereto, an optimization of the prediction of $HbA_{1c}$ (Algorithm 1) through: (1) Weighting higher the more proximal SMBG; (2) Weighting higher more prolonged high BG events: (3) Calibrating the High is BG Index with an earlier $HbA_{1c}$, and (4) Incorporating other patient variables, such as age, gender and duration of disease.

Algorithm 1 includes an optimal function of SMBG data that evaluates subsequent $HbA_{1c}$, as well as recommendations for the optimal duration of the data collection period and the optimal frequency of self-monitoring during that period. It is essential to note, however, that the broader goal of Algorithm 1 is to evaluate the status of patients' glycemic control. Although $HbA_{1c}$ is the accepted "gold standard" for evaluation of glycemic control, currently it is unclear whether another measure, such as average SMBG or High BG Index, would not be a better predictor of long-term complications in diabetes than $HbA_{1c}$. Until this issue is clarified, the goal of Algorithm 1 will be to estimate $HbA_{1c}$. In order to approximate as closely as possible future real applications of Algorithm 1 we proceeded as follows:

(1) First, several optimal functions using different independent variables, optimal duration, and optimal frequency of SMBG were derived from two training data sets 1 and 2, collected in our previous studies involving patients with T1DM;

(2) Then, all coefficients were fixed and Algorithm 1 was applied to the much larger test data set containing data for both T1DM and T2DM subjects collected under very different conditions in a clinical trial conducted by Amylin Pharmaceuticals.

(3) Detailed estimation of the preciseness of Algorithm 1 for various optimal functions was made using the test data set only.

This separation of training and test data sets allows us to claim that the estimated preciseness of Algorithm 1 can be generalized to any other data of subjects with T1DM or T2DM. Moreover, since the Amylin data (test data set) were collected from subjects who were undergoing treatment to lower their $HbA_{1c}$, and therefore exhibited unusually large variation of their $HbA_{1c}$ over the 6-month period of observation, we can claim that Algorithm 1 is predictive not only of relatively constant $HbA_{1c}$, but also of large and unusually rapid changes in $HbA_{1c}$. Along these same lines, Algorithm 1 would be most useful for patients who have their goal to optimize their $HbA_{1c}$, which is presumably the patient group most likely to be interested in purchasing a meter with advanced features such as continuous evaluation of $HbA_{1c}$.

Summary of the Results

The optimal SMBG data collection period is 45 days;

The optimal frequency of SMBG is 3 reading per day;

Two optimal $HbA_{1c}$ estimating functions were developed: F1—using only SMBG data, and F2—using SMBG data plus an $HbA_{1c}$ reading taken approximately 6 months prior to the $HbA_{1c}$ that is being predicted;

The evaluation of the accuracy of $HbA_{1c}$ prediction in the test data set (N=573 subjects) was done by several criteria that are detailed in the following pages (Table 2). Here we will mention that in T1DM the overall accuracy (within 20% of measured $HbA_{1c}$) of F1 was 96.5% and the overall accuracy of F2 was 95.7%. For T2DM the overall accuracy of F1 was 95.9%, the overall accuracy of F2 was 98.4%. Thus, the accuracy of both F1 and F2 is comparable to a direct measurement of $HbA_{1c}$;

Most importantly, for patients whose $HbA_{1c}$ changed 2 or more units from their baseline reading (N=68), the accuracy of F1 in predicting this change was 100% in both T1DM and T2DM, while the accuracy of F2 was 71% and 85% in T1DM and T2DM respectively;

Both F1 and F2 provided substantially more accurate estimation of $HbA_{1c}$ at 6 months than the original $HbA_{1c}$ estimate at month 0. Using the average BG as a direct estimate of $HbA_{1c}$ is not accurate as well;

A number of alternative approaches were tested, such as selecting specific times of the day (postprandial reading) for evaluation of $HbA_{1c}$, different weighting of SMBG readings according to the elapsed time between each SMBG reading and $HbA_{1c}$ determination, separate evaluation of subjects with different average blood glucose—to $HbA_{1c}$ ratio, etc. While some of these alternative approaches achieved certain better results than the two functions proposed above, none was better overall. We can conclude that the optimal functions F1 and F2 will be used in future applications of Algorithm 1.

Detailed Results—Test Data Set

The most important part of the evaluation of Algorithm 1 is the evaluation of its performance on a data that are not related to the data used for its development and optimization. From the test data set, the data of 573 subjects, N=254 with T1DM and N=319 with T2DM, were complete enough to be used for the evaluation of Algorithm 1.

Optimal Algorithm 1: For each subject, a 45-day subset of his/her SMBG reading was selected. This subset had a starting date of approximately 75 days before the subject's 6-month $HbA_{1c}$ assay and ending date approximately 30 days before that assay. Since in this data set the time of $HbA_{1c}$ assay is known only approximately, the elapsed time between last SMBG reading taken into analysis and $HbA_{1c}$ is not exact. This time period was selected through sequential optimization of its duration and its ending point (how long before $HbA_{1c}$). The optimal duration was 45 days. The optimal ending time was 1 month prior to $HbA_{1c}$. In other words, a 45-day SMBG would predict the values of $HbA_{1c}$ approximately one month ahead. However, the prediction of any other $HbA_{1c}$ value between days 45 and 75 is almost as good—the differences are numerical rather than of clinical significance. Similarly, the difference between a 45-day monitoring period and a 60-day monitoring period is not great. However, monitoring periods shorter than 45 days cause a rapid decline in predictive power.

The optimal estimation functions are linear and are given by the formulas:

Estimate 1—Without prior knowledge of $HbA_{1c}$:

$$F1 = 0.809098*BGMM1 + 0.064540*LBGI1 - 0.151673*RHI1 + 1.873325$$

Estimate 2—Knowing a prior $HbA_{1c}$ (approximately 6 months ago).

$$F2 = 0.682742*HBA0 + 0.054377*RHI1 + 1.553277$$

In these formulas BGMM1 is the average blood glucose computed from the 45 days of SMBG readings; LBGI1 and RHI1 are the Low and the High BG Indices computed from the same readings, and HBA0 is the baseline $HbA_{1c}$ reading that is used for Estimate 2 only. The values of the coefficients are optimized using the training data set and relevant statistics and plots are presented in section Detailed Results—Training data set.

The functions F1 and F2 produce point estimates of $HbA_{1c}$, i.e. each function produces an estimated value of $HbA_{1c}$. Interval estimates can be obtained by using the regression error estimates presented in section Detailed Results—Training data set. However, applied to the test data set, these interval estimates will not be true 90% or 95% confidence intervals for $HbA_{1c}$ because they are originally derived from the training data set and are only applied to the test data (see also the statistical note in the next section).

Evaluation of the accuracy of Algorithm 1: Tables 2A and 2B present results from the evaluation of the optimal Algorithm 1 with data from the test data set for subjects with T1DM and T2DM, respectively. Several criteria were used:
(1) Absolute deviation (AERR) of Estimated from measured $HbA_{1c}$;
(2) Absolute percent deviation (PERR) of Estimated from measured $HbA_{1c}$;
(3) Percent Estimates within 20% of measured $HbA_{1c}$ (HIT 20),
(4) Percent readings within 10 of measured $HbA_{1c}$ (HIT 10), and
(5) Percent readings outside of a 25%-zone around measured $HbA_{1c}$ (MISS 25).

TABLE 2A

Accuracy of Algorithm 1 in T1DM (N = 254 subjects).

|  | F1 | F2 | Average BG | Prior $HbA_{1c}$ | P-value |
|---|---|---|---|---|---|
| AERR | 0.77 | 0.61 | 1.68 | 1.1 | <0.001 |
| PERR (%) | 8.3 | 7.1 | 19.4 | 12.8 | <0.001 |
| HIT20 (%) | 96.5 | 95.7 | 61.0 | 81.0 | <0.001 |
| HIT10 (%) | 65.4 | 75.5 | 29.9 | 48.2 | <0.001 |
| MISS 25 (%) | 2.4 | 1.6 | 28.4 | 9.9 | |

TABLE 2B

Accuracy of Algorithm 1 in T2DM (N = 319 subjects).

|  | F1 | F2 | Average BG | Prior $HbA_{1c}$ | P-value |
|---|---|---|---|---|---|
| AERR | 0.72 | 0.57 | 1.92 | 0.87 | <0.001 |
| PERR (%) | 7.6 | 6.4 | 20.9 | 11.7 | <0.001 |
| HIT20 (%) | 95.9 | 98.4 | 56.4 | 82.8 | <0.001 |
| HIT10 (%) | 70.2 | 79.3 | 29.5 | 53.3 | <0.001 |
| MISS 25 (%) | 1.2 | 0.6 | 36.7 | 8.2 | <0.001 |

The first two columns in Tables 2A and 2B present the results for the optimal functions F1 and F2 respectively. The third column presents the accuracy of the estimation if the average BG (in mmol/l) was taken as an estimate of $HbA_{1c}$. The fourth column presents the same accuracy measures computed using the $HbA_{1c}$ assay at time 0 as an estimate of $HbA_{1c}$ at 6 months. It is evident that for both T1DM and T2DM F2 is a little better overall estimate of $HbA_{1c}$ than F1. Most importantly, both F1 and F2 are substantially better estimates of $HbA_{1c}$ than its earlier value, or than the average BG. This is especially true for the % estimates that fell outside of the 25% accuracy zone. The difference between the performance of F1 and F2 and the estimate from a prior $HbA_{1c}$ assay is highly significant (column 4).

Statistical Note: It is important to note that it is not appropriate to evaluate the accuracy of Algorithm 1 using traditional, regression-type criteria, such as $R^2$ or F and p values from ANOVA table. This is because the parameter estimates were derived from another unrelated data set (the training data) and are only applied to this test data set. Thus, statistical assumptions for the underlying model are violated (for example in the test data set the sum of the residuals will not be zero) and therefore $R^2$, F, and p lose their statistical meaning.

Further evaluation of the accuracy of Algorithm 1 in the test data set was done by reviewing the T1DM and T2DM subjects who had a substantial change in their SMBG reading from the baseline to 6-month follow-up. Tables 3A and 3B present list of the T1DM and T2DM subjects who had an absolute change in their $HbA_{1c}$ equal to or greater than 2 units. In each subject group 34 subjects had such a change in $HbA_{1c}$. Algorithm 1, function F1, predicted 100% of such changes in both T1DM and T2DM. The predictive power of F2 was diminished due to the inclusion of baseline $HbA_{1c}$ in the equation (which partially pulls the estimates back to the baseline value of $HbA_{1c}$) and was 71% in T1DM and 85% in T2DM. The baseline $HbA_{1c}$ was outside of the 20% zone from 6-month $HbA_{1c}$ for all but 2 subjects:

TABLE 3A

T1DM subjects who experienced change in their $HbA_{1c}$ >= 2 units.

| ID HBA0 | HBA0 | HBA6 | DHBA | F1 | F2 | HIT F1 | HIT F2 | HIT |
|---|---|---|---|---|---|---|---|---|
| 6504 | 12.0 | 7.0 | 5.00 | 6.82 | 9.90 | 100.00 | .00 | .00 |
| 6613 | 10.5 | 6.8 | 3.70 | 8.02 | 9.37 | 100.00 | .00 | .00 |
| 4003 | 12.4 | 8.9 | 3.50 | 8.45 | 10.73 | 100.00 | .00 | .00 |
| 6204 | 11.0 | 7.5 | 3.50 | 7.29 | 9.45 | 100.00 | .00 | .00 |
| 3709 | 13.0 | 9.7 | 3.30 | 8.99 | 11.54 | 100.00 | 100.00 | .00 |
| 4701 | 12.8 | 9.5 | 3.30 | 9.50 | 11.61 | 100.00 | .00 | .00 |
| 3614 | 11.9 | 8.7 | 3.20 | 8.24 | 10.30 | 100.00 | 100.00 | .00 |
| 3602 | 11.5 | 8.3 | 3.20 | 7.93 | 9.94 | 100.00 | 100.00 | .00 |

TABLE 3A-continued

T1DM subjects who experienced change in their $HbA_{1c}$ >= 2 units.

| ID HBA0 | HBA0 | HBA6 | DHBA | F1 | F2 | HIT F1 | HIT F2 | HIT |
|---|---|---|---|---|---|---|---|---|
| 6008 | 11.3 | 8.3 | 3.00 | 9.30 | 10.53 | 100.00 | .00 | .00 |
| 3723 | 13.0 | 10.1 | 2.90 | 8.80 | 11.46 | 100.00 | 100.00 | .00 |
| 7010 | 12.7 | 9.8 | 2.90 | 8.09 | 10.89 | 100.00 | 100.00 | .00 |
| 6208 | 11.5 | 8.7 | 2.80 | 8.42 | 10.09 | 100.00 | 100.00 | .00 |
| 6202 | 10.6 | 7.8 | 2.80 | 7.91 | 9.37 | 100.00 | .00 | .00 |
| 3924 | 9.9 | 7.2 | 2.70 | 7.71 | 8.72 | 100.00 | .00 | .00 |
| 8211 | 11.0 | 8.3 | 2.70 | 8.76 | 10.32 | 100.00 | .00 | .00 |
| 6012 | 9.3 | 6.7 | 2.60 | 7.82 | 8.35 | 100.00 | .00 | .00 |
| 3913 | 11.0 | 8.4 | 2.60 | 7.88 | 9.54 | 100.00 | 100.00 | .00 |
| 6701 | 11.2 | 8.6 | 2.60 | 8.75 | 10.07 | 100.00 | 100.00 | .00 |
| 2307 | 10.6 | 8.1 | 2.50 | 7.95 | 9.27 | 100.00 | 100.00 | .00 |
| 3516 | 11.8 | 9.3 | 2.50 | 7.76 | 10.03 | 100.00 | 100.00 | .00 |
| 5808 | 9.6 | 7.2 | 2.40 | 7.61 | 8.52 | 100.00 | 100.00 | .00 |
| 2201 | 11.8 | 9.5 | 2.30 | 8.90 | 10.71 | 100.00 | 100.00 | .00 |
| 4010 | 12.4 | 10.1 | 2.30 | 8.57 | 11.15 | 100.00 | 100.00 | .00 |
| 6210 | 11.9 | 9.6 | 2.30 | 8.33 | 10.40 | 100.00 | 100.00 | .00 |
| 4904 | 11.3 | 9.1 | 2.20 | 8.63 | 10.29 | 100.00 | 100.00 | .00 |
| 6709 | 10.3 | 8.1 | 2.20 | 7.83 | 9.04 | 100.00 | 100.00 | .00 |
| 6619 | 9.5 | 7.3 | 2.20 | 7.64 | 8.57 | 100.00 | 100.00 | .00 |
| 3921 | 10.9 | 8.8 | 2.10 | 7.20 | 9.19 | 100.00 | 100.00 | .00 |
| 6603 | 11.0 | 8.9 | 2.10 | 8.18 | 9.89 | 100.00 | 100.00 | .00 |
| 7415 | 10.6 | 8.5 | 2.10 | 7.94 | 9.27 | 100.00 | 100.00 | .00 |
| 6515 | 9.8 | 7.8 | 2.00 | 7.13 | 8.54 | 100.00 | 100.00 | .00 |
| 3611 | 10.3 | 8.3 | 2.00 | 8.36 | 9.23 | 100.00 | 100.00 | .00 |
| 3732 | 13.2 | 11.2 | 2.00 | 9.30 | 11.99 | 100.00 | 100.00 | 100.00 |
| 7409 | 10.0 | 8.0 | 2.00 | 7.99 | 9.04 | 100.00 | 100.00 | .00 |

TABLE 3B

T2DM subjects who experienced change in their $HbA_{1c}$ >= 2 units.

| ID HBAO | HBAO | HBA6 | DHBA | F1 | F2 | HIT F1 | HIT F2 | HIT |
|---|---|---|---|---|---|---|---|---|
| 6754 | 10.8 | 7.0 | 3.80 | 6.90 | 9.03 | 100.00 | .00 | .00 |
| 6361 | 11.3 | 7.6 | 3.70 | 8.51 | 10.20 | 100.00 | .00 | .00 |
| 6270 | 12.0 | 8.6 | 3.40 | 7.85 | 10.03 | 100.00 | 100.00 | .00 |
| 6264 | 11.1 | 7.8 | 3.30 | 8.31 | 9.70 | 100.00 | .00 | .00 |
| 6355 | 11.8 | 8.6 | 3.20 | 7.99 | 9.90 | 100.00 | 100.00 | .00 |
| 3961 | 10.8 | 8.0 | 2.80 | 9.13 | 9.73 | 100.00 | .00 | .00 |
| 6555 | 11.1 | 8.3 | 2.80 | 8.11 | 9.55 | 100.00 | 100.00 | .00 |
| 8052 | 11.7 | 8.9 | 2.80 | 7.68 | 9.80 | 100.00 | 100.00 | .00 |
| 5356 | 9.7 | 7.0 | 2.70 | 6.75 | 8.20 | 100.00 | 100.00 | .00 |
| 3966 | 10.3 | 7.7 | 2.60 | 8.08 | 9.07 | 100.00 | 100.00 | .00 |
| 908 | 9.5 | 6.9 | 2.60 | 7.47 | 8.23 | 100.00 | 100.00 | .00 |
| 6554 | 10.7 | 8.1 | 2.60 | 8.16 | 9.42 | 100.00 | 100.00 | .00 |
| 2353 | 11.1 | 8.7 | 2.40 | 8.99 | 9.90 | 100.00 | 100.00 | .00 |
| 4064 | 11.3 | 8.9 | 2.40 | 7.89 | 9.88 | 100.00 | 100.00 | .00 |
| 6351 | 10.1 | 7.7 | 2.40 | 7.92 | 8.63 | 100.00 | 100.00 | .00 |
| 7551 | 12.2 | 9.8 | 2.40 | 9.17 | 11.02 | 100.00 | 100.00 | .00 |
| 6358 | 8.4 | 6.1 | 2.30 | 7.00 | 7.32 | 100.00 | .00 | .00 |
| 3965 | 10.1 | 7.8 | 2.30 | 7.83 | 8.64 | 100.00 | 100.00 | .00 |
| 914 | 11.1 | 8.8 | 2.30 | 9.57 | 10.33 | 100.00 | 100.00 | .00 |
| 1603 | 10.2 | 7.9 | 2.30 | 8.02 | 8.88 | 100.00 | 100.00 | .00 |
| 1708 | 10.8 | 8.6 | 2.20 | 7.62 | 9.24 | 100.00 | 100.00 | .00 |
| 3761 | 12.4 | 10.2 | 2.20 | 9.13 | 10.86 | 100.00 | 100.00 | .00 |
| 3768 | 11.2 | 9.0 | 2.20 | 8.29 | 9.74 | 100.00 | 100.00 | .00 |
| 326 | 10.3 | 8.2 | 2.10 | 7.45 | 8.78 | 100.00 | 100.00 | .00 |
| 109 | 9.3 | 7.2 | 2.10 | 7.70 | 8.18 | 100.00 | 100.00 | .00 |
| 1501 | 11.9 | 9.8 | 2.10 | 8.52 | 10.18 | 100.00 | 100.00. | .00 |
| 3964 | 13.7 | 11.6 | 2.10 | 10.08 | 12.65 | 100.00 | 100.00 | 100.00 |
| 4352 | 12.2 | 10.1 | 2.10 | 9.51 | 11.14 | 100.00 | 100.00 | .00 |
| 7858 | 12.1 | 10.0 | 2.10 | 9.53 | 11.01 | 100.00 | 100.00 | .00 |
| 4256 | 10.6 | 8.6 | 2.00 | 8.76 | 9.69 | 100.00 | 100.00 | .00 |
| 4752 | 10.1 | 8.1 | 2.00 | 8.51 | 8.87 | 100.00 | 100.00 | .00 |
| 6556 | 11.1 | 9.1 | 2.00 | 8.72 | 9.68 | 100.00 | 100.00 | .00 |
| 6562 | 7.9 | 5.9 | 2.00 | 7.07 | 7.04 | 100.00 | 100.00 | .00 |
| 8255 | 10.9 | 8.9 | 2.00 | 8.90 | 9.87 | 100.00 | 100.00 | .00 |

In Tables 3A and 3B:
ID—subject's ID number;
HBA0—baseline $HbA_{1c}$;
HBA6—measured 6-month $HbA_{1c}$;
DHBA—absolute difference between baseline and 6-month $HBA_{1c}$;
F1—Estimated $HbA_{1c}$ by Function F1, SMBG data only;
F2—Estimated $HbA_{1c}$ by Function F2 using prior $HbA_{1c}$ assay;
Hit F1=100 if F1 is within 20% of 6-month $Hba_{1c}$ reading, 0 otherwise;
Hit F2=100 if F2 is within 20% of 6-month $Hba_{1c}$ reading, 0 otherwise, and
Hit HbA0=100 if baseline $HbA_{1c}$ is within 20% of 6-month $Hba_{1c}$ reading, 0 otherwise.

Detailed Results—Training Data Set

This section describes the steps to optimization of Algorithm 1. This optimization included two parts: (1) Assuming that no previous $HbA_{1c}$ reading is available, and (2) Assuming that a prior $HbA_{1c}$ could be used for prediction of $HbA_{1c}$.

Several different functions were considered for description of the relationship between SMBG data and $HbA_{1c}$. Optimal, in terms of accuracy and simplicity of computation, appeared to be a linear function of the average of SMBG readings, Low and High BG Indices, if no prior HbA1c reading is used and another linear function of a prior $HbA_{1c}$ and the High BG Index. Nonlinear relationships did not enhance the goodness-of-fit of the models and therefore are not considered for practical application.

Training Data set 1—No prior $HbA_{1c}$ A linear regression model was used to optimize the coefficient of function F1. The optimal coefficients were presented in the previous section. Here we give data about the goodness-of-fit of the model:

| Multiple R | .71461 |
|---|---|
| R Square | .51067 |

| Analysis of Variance | | | |
|---|---|---|---|
| | DF | Sum of Squares | Mean Square |
| Regression | 3 | 154.57097 | 51.52366 |
| Residual | 90 | 148.10903 | 1.64566 |
| F = 31.30889 | | Signif F = .0000 | |

Figure 11:
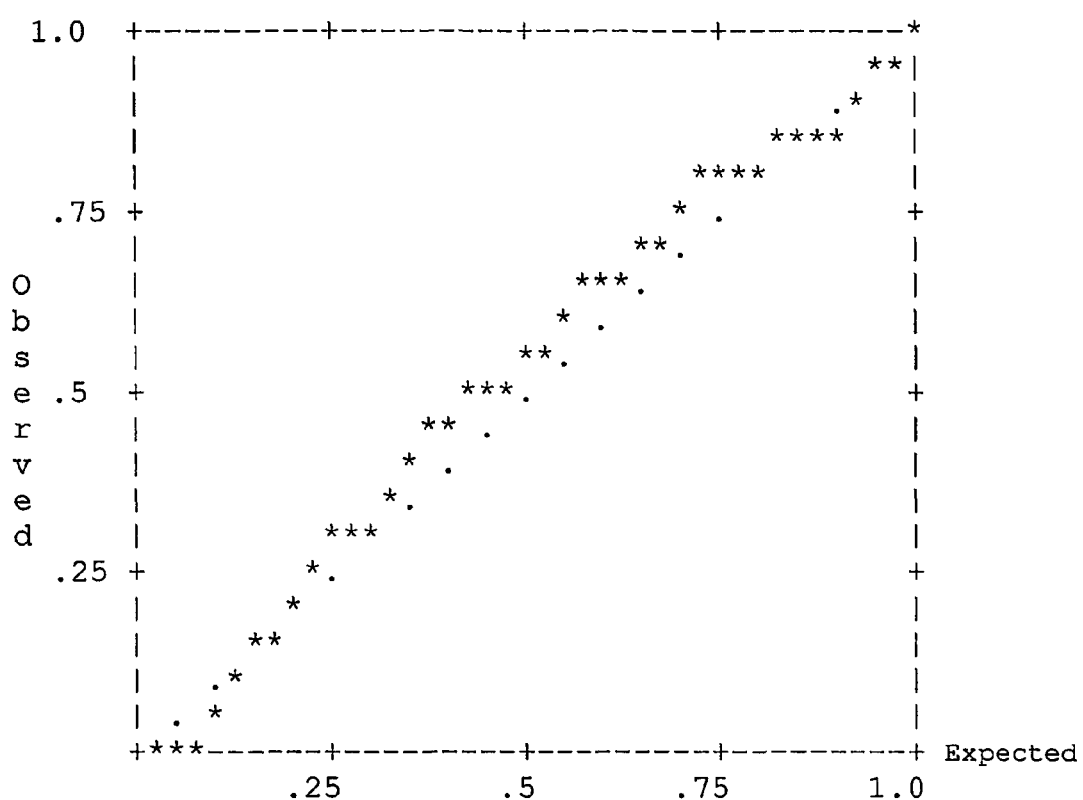
FIG. 11 graphically shows the analysis of the residuals of this model showed a close to normal distribution of the residuals for Training Data set 1 of Example No. 1.

Analysis of the residuals of this model showed a close to normal distribution of the residuals (see FIG. 11). The SD of the residuals was 1.2 (the mean is 0 by definition). Therefore we can accept that this model described the data well.

Training Data set 2—Prior $HbA_{1c}$: Again, a linear regression model was used to optimize the coefficient of function F2. The optimal coefficients were presented in the previous section. Here we give data about the goodness-of-fit of the model:

| Multiple R | .86907 |
|---|---|
| R Square | .75528 |

| Analysis of Variance | | | |
|---|---|---|---|
| | DF | Sum of Squares | Mean Square |
| Regression | 4 | 38.70237 | 9.67559 |
| Residual | 54 | 12.54000 | .23222 |
| F = 41.66522 | | Signif F = .0000 | |

Figure 12:
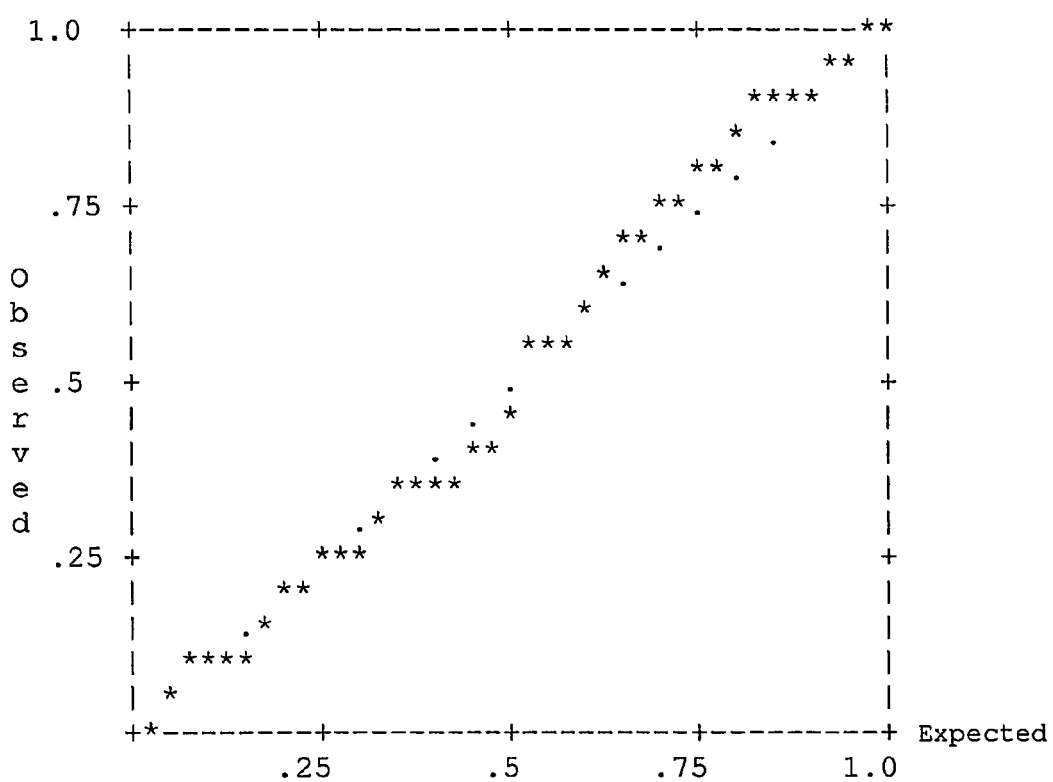
FIG. 12 graphically shows the analysis of the residuals of this model showed a close to normal distribution of the residuals 1 of Example No. 1

Analysis of the residuals of this model showed a close to normal distribution of the residuals (see FIG. 12). The SD of the residuals was 0.47. Therefore we can accept that this model described the data well.

In addition, comparing the models without and with a prior HbA1c, we can conclude that if a prior HbA1c is available for inclusion in the computations, the resulting model is substantially better both in terms of $R^2$ and in terms of residual error.

However, as we saw in the previous section, a prior $HbA_{1c}$ does not contribute to the overall accuracy of prediction in an unrelated dataset and, in certain cases when $HbA_{1c}$ changed substantially, is even obstructing the ability of the algorithm to account for rapid changes. Thus, we can conclude that, even if a prior $HbA_{1c}$ maybe better from a statistical point of view, it may not have a sufficient practical utility to justify an inclusion of input of a reading in future meters. We also don't know what could be the elapsed time between an HbA1c assay and SMBG profile that would still render the HBA1c input useful. Perhaps this depends on the change of HBA1c during that time period—as we saw in the previous section, a change of 2 HbA1c units makes a prior HbA1c reading completely useless.

The Ratio of SMBG to $HbA_{1c}$

We will now present an alternative way to improve the statistical accuracy of the model fit and to keep a reasonable clinical applicability. It turns out that the ratio between the average of 45 days of SMBG readings and $HbA_{1c}$ is a measure that has an almost perfect normal distribution (as evidenced by Kolmogorov-Smirnov test) and, most importantly, identifies three groups of subjects for whom this ratio is below 1.0, between 1.0 and 1.2, and above 1.2. Each of the first two groups accounts for approximately 40% of the subjects, the third group accounts for approximately 20% of the subjects. This is valid for both T1DM and T2DM and is observed in the training as well as in the test data sets. In addition, this ratio seems to be pretty stable over time and is perhaps a measure that reflects patients SMBG habits (for example, if SMBG is performed mostly at times when BG is low, the resulting average will underestimate $HbA_{1c}$ and the corresponding ratio will be below 1.0). Keeping in mind that this is just a hypothesis that cannot be validated with the available data, we make some analyses that seem to demonstrate certain utility in knowing each person's ratio at some point of time. This may seem equivalent to knowing a prior $HbA_{1c}$, and it is perhaps equivalent in terms of data input, however the use of the ratio is very different than the use of a prior $HbA_{1c}$. Instead of being included directly into the prediction formula, the ratio is used to classify the person into using one of three different prediction formulas. These new formulas do not include $HbA_{1c}$ directly and therefore do not suffer by the inertia of prediction that such inclusion may cause. In addition the average $HbA_{1c}$ is not substantially different between the three groups defined by the ratio and is not correlated to the ratio, so the reason for different ratios in different persons must be unrelated to $HbA_{1c}$.

If we first classify the subjects in three groups according to their ratio and perform separate regression in the training data set, the goodness-of fit of the regression models increases substantially: (1) In group 1 (Ratio<1.0) we get Multiple R=0.86 and $R^2$=0.73; (2) In group 2 (Ration between 1.0 and 0.1.2) the fit is almost perfect, R-0.97, $R^2$=0.94, and (3) In group 3 (ratio>1.2) the fit is worst R=0.69, $R^2$=0.47. Since all three regression models do not include a prior $HbA_{1c}$, we can conclude that the goodness-of-fit increases dramatically for about 80% of the subjects, remains the same for the rest 20% of the subjects, and these subjects for whom the fit will be worse can be identified in advance.

Further, separating the test data set in three groups according to the subject's ratio, we get prediction accuracy similar to the accuracy we have achieved before (Tables 4A and 4B):

TABLE 4A

Accuracy of Algorithm 1 in T1DM (N = 254 subjects).

|  | Ratio ≤ 1.0 | 1.0 ≤ Ratio ≤ 1.2 | Ratio ≥ 1.2 |
|---|---|---|---|
| AERR | 0.70 | 0.63 | 0.74 |
| PERR (%) | 7.8 | 7.4 | 7.9 |
| HIT20 (%) | 93.8 | 93.0 | 95.5 |
| HIT10 (%) | 68.8 | 73.4 | 72.7 |
| MISS 25 (%) | 3.1 | 2.6 | 0.0 |

TABLE 4B

Accuracy of Algorithm 1 in T2DM (N = 319 subjects).

|  | Ratio ≤ 1.0 | 1.0 ≤ Ratio ≤ 1.2 | Ratio ≥ 1.2 |
|---|---|---|---|
| AERR | 0.63 | 0.68 | 0.89 |
| PERR (%) | 7.6 | 7.8 | 8.8 |
| HIT20 (%) | 97.4 | 95.0 | 95.3 |
| HIT10 (%) | 67.2 | 65.3 | 57.7 |
| MISS 25 (%) | 0.0 | 1.7 | 0.0 |

In short, knowing the SMBG to HBA1c ratio for each subject and using separate estimates accordingly, seem to improve the statistical performance of the models without losing clinical accuracy.

Other Hypotheses and Ideas that Were Tested

We have tested a number of other hypotheses and ideas which may prove useful at least for prompt and more focused analysis of the data that are collected by Example No. 2. A brief account of the results follows:

(1) $HbA_{1c}$ is most associated (correlated) with SMBG readings taken in the afternoon hours—from 12 noon to 6 p.m. and least associated with fasting SMBG readings (4 a.m.-8 a.m.). However, it does not follow that taking only postprandial SMBG readings would improve the prediction of $HbA_{1c}$. on the contrary, the prediction would become worse if the [relatively small but important] contribution of all hours throughout the day is ignored. It is possible to improve a the prediction of $HbA_{1c}$ a little if different hours throughout the day get different weighting, however the improvement is not sufficient to justify this additional complication of the model;

(2) The relationship between $HbA_{1c}$ and average SMBG is substantially stronger in T2DM compared to T1DM, even if the two groups are matched by $HBA_{1c}$. In terms of direct correlation, in T1DM the coefficient is about 0.6 while in T2DM the coefficient is about 0.75 throughout the studies;

(3) Experiments with different weighting of SMBG reading dependent on the elapsed time between SMBG and $HBA_{1c}$ assay (such as weighting higher more proximal results) did not yield better prediction of $HBA_{1c}$;

(4) Inclusion of demographic variables, such as age, duration of diabetes, gender, etc., does not improve the prediction of HBA1c;

(5) The simplest possible linear relationship between $HbA_{1c}$ and average SMBG (measured in mmol/l) is given by the formula: $HbA_{1c}=0.41046*BGMM+4.0775$. Although statistically inferior to the formulas F1 and F2, this formula provides $HbA_{1c}$ estimates that are about 95% accurate in both T1DM and T2DM (in terms of deviation less than 20% from $HbA_{1c}$ assay) and maybe useful if the computation of the Low and High BG Indices presents an issue for incorporation in a meter (however, the prediction of hypoglycemia cannot be done without computing the Low BG Index and therefore this formula might be useful only for meters that include Algorithm 1 but not include Algorithms 2 and 3).

Algorithm 2: Evaluation of Long-Term Risk for SH.

Example No. 1 provides for, but not limited thereto, an expansion of Algorithm 2 to include estimating individual probabilities for biochemical significant hypoglycemia (BSH, defined as BG reading <=39 mg/dl) or biochemical moderate hypoglycemia (BMH, defines as 39 mg/dl<BG reading <=55 mg/dl). In addition, we planned to evaluate whether Algorithm 2 predicts better occurrence of nocturnal (midnight to 7:00 am) SH, compared to daytime SH.

Algorithm 2 is a classification algorithm. That is, based on SMBG data for a subject, it classifies the subject in a certain risk category for future BSH or MSH. In order to approximate as closely as possible future real applications of Algorithm 2 we proceeded as follows:

(4) First, several optimal classification variables and optimal classification categories optimal duration, and optimal frequency of SMBG were derived from training data set 1;

(5) Then, the test data set was split into two sections: first 45 days, and the rest of the data. The optimal parameters of Algorithm 2 were applied to the first 45-day portion of the data and the so estimated probabilities for future BSH or MSH were used to predict BSH and MSH in the second portion of the data;

(6) Detailed estimation of the preciseness of Algorithm 2, was made using test data only.

This separation of training and test data sets allows us to claim that the estimated preciseness of Algorithm 2 can be generalized to any other data of subjects with T1DM or T2DM. Moreover, since the Amylin data were collected from subjects who were undergoing intensive treatment, we can speculate that Algorithm 2 is tested and proven useful in subjects with changing and increasing risk for hypoglycemia.

Summary of the Results

The optimal SMBG data collection period needed for estimation of the probability for future BSH or BMH is 40 to 45 days. The optimal frequency of SMBG is 3 to 4 readings per day. Larger number of readings does not lead to a substantial increase of the predictive power of Algorithm 2. With less than 3 reading per day the predictive power declines. However, this requirement refers to average number of readings per day for the 45-day observation period, it does not necessarily mean that 3-4 readings need to be performed every day;

The relationship between predictor variables and future SH and MH is strictly nonlinear. Consequently, linear methods are not applicable for optimal prediction, although an $R^2=50\%$ can be achieved by a direct linear model (in comparison, the best result in the DCCT was 8% prediction of future SH);

A separate prediction of nocturnal SH is generally weaker than prediction of daytime SH;

Fifteen risk categories for future BSH and BMH were identified. The best separation of categories was achieved on the basis of the Low BG Index alone, although combinations between the low BG Index and other variables worked similarly well;

Although the frequencies of BSH and BMH were different between T1DM and T2DM (see Table 5), the conditional frequencies, given a risk category, were not different between T1DM and T2DM. This allowed for unified approach to the risk of SH and MH;

Various empirical probabilities for future were computed and compared for the 15 risk categories. All comparisons were highly significant, p's<0.0005.

These empirical probabilities were approximated by a two-parameter Weibull distributions yielding theoretical probabilities for future BSH and BMH in each risk category.

if (LBGI gt 5.25 and LBGI le 6.50) RCAT=13.

if (LBGI gt 6.50) RCAT=14.

Observed frequency of BSH and BMH: For each subject, any occurrences of BSH and BMH registered by SMBG were counted for 1-month, 3-month, and 6-month periods following the initial 45-day data collection. Table 5A presents the observed frequencies of 0, >=1, >=2, and >=3 BSH and BMH for T1DM, Table 5B presents the same data for T2DM:

TABLE 5A

Observed frequency of BSH and BMH in T1DM

|  | BSH (BG $\leq$ 39 mg/dl) | | | BMH (39 mg/dl < BG $\leq$ 55 mg/dl) | | |
| --- | --- | --- | --- | --- | --- | --- |
|  | 1 month | 3 months | 6 months | 1 month | 3 months | 6 months |
| Average #/Subject | 0.82 | 1.77 | 2.74 | 3.64 | 8.33 | 12.93 |
| % Ss with 0 episodes | 62.8 | 50.8 | 46.6 | 25.2 | 18.0 | 17.7 |
| % Ss with $\geq$ 2 episodes | 18.8 | 33.1 | 38 | 64.3 | 75.6 | 77.1 |
| % Ss with $\geq$ 3 episodes | 9.8 | 23.3 | 28.2 | 50.8 | 68.0 | 71.1 |

TABLE 5B

Observed frequency of BSH and BMH in T2DM

|  | BSH (BG $\leq$ 39 mg/dl) | | | BMH (39 mg/dl < BG $\leq$ 55 mg/dl) | | |
| --- | --- | --- | --- | --- | --- | --- |
|  | 1 month | 3 months | 6 months | 1 month | 3 months | 6 months |
| Average #/Subject | 0.18 | 0.53 | 0.76 | 1.11 | 2.93 | 4.59 |
| % Ss with 0 episodes | 91.4 | 84.9 | 81.3 | 73.0 | 61.1 | 55.8 |
| % Ss with $\geq$ 2 episodes | 3.6 | 8.6 | 10.1 | 18.1 | 26.7 | 30.3 |
| % Ss with $\geq$ 3 episodes | 1.5 | 5.9 | 7.4 | 13.9 | 21.4 | 25.8 |

The goodness-of-fit of these approximation was very good—all coefficients of determination were above 85%, some as high as 98% (see FIGS. 1-5 and 9-10).

Detailed Results—Test Data Set

Identifying personal risk categories for SH/MH: The data for all 600 subjects were used for these analyses. The Low BG Index (LBGI was computed for each subject from his/her first 45 days of SMBG data collection. Then, the LBGI for was classified in one of the 15 optimal risk categories (variable RCAT ranging from 0 to 14) as derived in training data set 1. These risk categories are defined by the inequalities:

if (LBGI le 0.25) RCAT=0.
if (LBGI gt 0.25 and LBGI le 0.5) RCAT=1.
if (LBGI gt 0.50 and LBGI le 0.75) RCAT=2.
if (LBGI gt 0.75 and LBGI le 1.00) RCAT=3.
if (LBGI gt 1.00 and LBGI le 1.25) RCAT=4.
if (LBGI gt 1.25 and LBGI le 1.50) RCAT=5.
if (LBGI gt 1.50 and LBGI le 1.75) RCAT=6.
if (LBGI gt 1.75 and LBGI le 2.00) RCAT=7.
if (LBGI gt 2.00 and LBGI le 2.50) RCAT=8.
if (LBGI gt 3.00 and LBGI le 3.50) RCAT=9.
if (LBGI gt 3.50 and LBGI le 4.00) RCAT=10.
if (LBGI gt 4.00 and LBGI le 4.50) RCAT=11.
if (LBGI gt 4.50 and LBGI le 5.25) RCAT=12.

Nocturnal BSH and BMH represented approximately 15% of all episodes registered by SMBG. As in the training data set the correlation between nocturnal-episodes and all predictor variables was weaker. We conclude that a targeted prediction of nocturnal episodes would be ineffective.

Empirical Probabilities for future BSH and BMH: Certain empirical probabilities for future BSH and BMH were computed in each of the 15 risk categories. These probabilities include: (1) Probabilities for at least one BSH or BMH within the next 1 month, 3 months, and 6 months; (2) Probabilities for at least two BSH or BMH within the next 3 months and 6 months, and (3) Probabilities for at least three BSH or BMH within the next 6 months. Of course, it is possible to compute any other combinations probabilities upon request.

A most important conclusion from this analysis was that, given a risk category, the probabilities for future BSH and BMH did not differ significantly between T1DM and T2DM. This allows for an unified approach to empirical and theoretical estimation of these probabilities in both T1DM and T2DM. Consequently, the data for T1DM and T2DM patients were combined for the following analyses.

FIGS. 1-5 and 9-10 present scatter-plots of the six computed empirical probabilities plotted along the 15 risk categories. The empirical probabilities for BSH are presented by black triangles, while the empirical probabilities for BMH are presented by red squares.

All sets of empirical probabilities were compared across the 15 risk categories using univariate ANOVAs, and all p-levels were below 0.0005. Therefore, we observe highly significant differences between the frequencies of BSH and BMH episodes in the different risk categories.

Theoretical Probabilities for future BSH and BMH: In order to be able to use direct-formula estimation of the probabilities for future BSH and BMH, we approximated the empirical probabilities using two-parameter Weibull probability distribution. The Weibull distribution function is given by the formula:

$$F(x)=1-exp(-a.x^b) \text{ for any x>0 and 0 otherwise}$$

Statistical Note: The parameters a and b are greater than 0 and are called scale and shape parameter, respectively. In the special case b=1, Weibull's distribution becomes exponential. This distribution is frequently used in engineering problems as the distribution of randomly occurring technical failures that are not completely unrelated to each other (If the failures are completely unrelated, then they would form a Poisson process that would be described by an exponential distribution, e.g. b=1). The situation here is remotely similar—we need to describe the distribution of events (failures) that are not completely independent and tend to occur in clusters as evidenced by our previous research.

Each set of empirical probabilities was approximated by the theoretical formula given above. The parameters were estimated using nonlinear least squares (with initial parameter estimates given by a linear double-logarithmic model). The goodness-of-fit of each model was evaluated by its coefficient of determination ($D^2$) This statistics has a meaning similar to that of $R^2$ in linear regression, however $R^2$ is not applicable to non-linear models.

The model fits are presented in FIGS. 1-6 as black lines for the probabilities of BSH and as dashed lines for the probabilities of BMH. Above each figure we present the parameter estimates for the corresponding models, thus we give direct formulas for computing-probabilities of 0, >=1, >=2, >=3 BSH or BMS episodes in periods of 1 month, 3 months, and 6 months following initial SMBG. Some of these formulas, or their versions, can be included in monitoring devices or software as indicators of risk for SH and MH.

The values of $D^2$ (and its square root D) are given below each figure as indicators of the preciseness of approximation. All values are above 85% and some reach 98%, which demonstrates that the approximation is very good and confirms that theoretical, instead of empirical probabilities could be used in future studies/application.

The theoretical probabilities for one or more moderate or severe hypoglycemic episodes are given by the formulas as shown in FIG. 1:

$$P(MH>=1)=1-exp(-exp(-1.5839)*Risk^{**} 1.0483)$$

$$P(SH>=1)=1-exp(-exp(-4.1947)*Risk^{**} 1.7472)$$

FIG. 1 presents the empirical and theoretical probabilities for moderate (dashed line) and severe (black line) hypoglycemia within one month after the SMBG assessment for each of the 15 categories of risk level defined by the Low BG Index. Since the models are nonlinear, the goodness-of-fit is evaluated by their coefficient of determination $D^2$, an analog of $R^2$ in linear models. The coefficients of determination and their square roots are as follows:
SH Model: $D^2$ 96%, D=98%.
MH Model: $D^2$=87%, D=93%.

Figure 2:
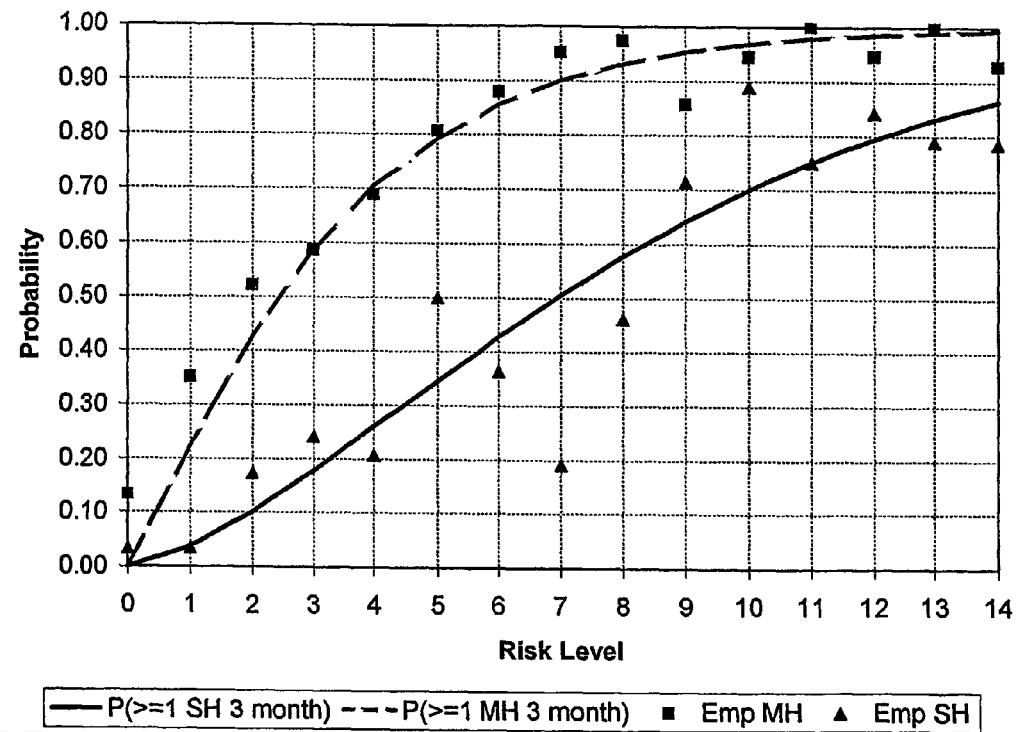
FIG. 2 graphically presents the empirical and theoretical probabilities for moderate (dashed line) and severe (black line) hypoglycemia within three months after the SMBG assessment for each of the 15 categories of risk level defined by the Low BG Index of Example No. 1.

The theoretical probabilities for one or more moderate or severe hypoglycemic episodes are given by the formulas as shown in FIG. 2:

$$P(MH>=1)=1-exp(-exp(-1.3731)*Risk^{**} 1.1351)$$

$$P(SH>=1)=1-exp(-exp(-3.2802)*Risk^{**} 1.5050)$$

FIG. 2 presents the empirical and theoretical probabilities for moderate (dashed line) and severe (black line) hypoglycemia within three months after the SMBG assessment for each of the 15 categories of risk level defined by the Low BG Index.

The coefficients of determination and their square roots are as follows:
SH Model: $D^2$=93%, D=97%.
MH Model: $D^2$=87%, D=93%.

Figure 3:
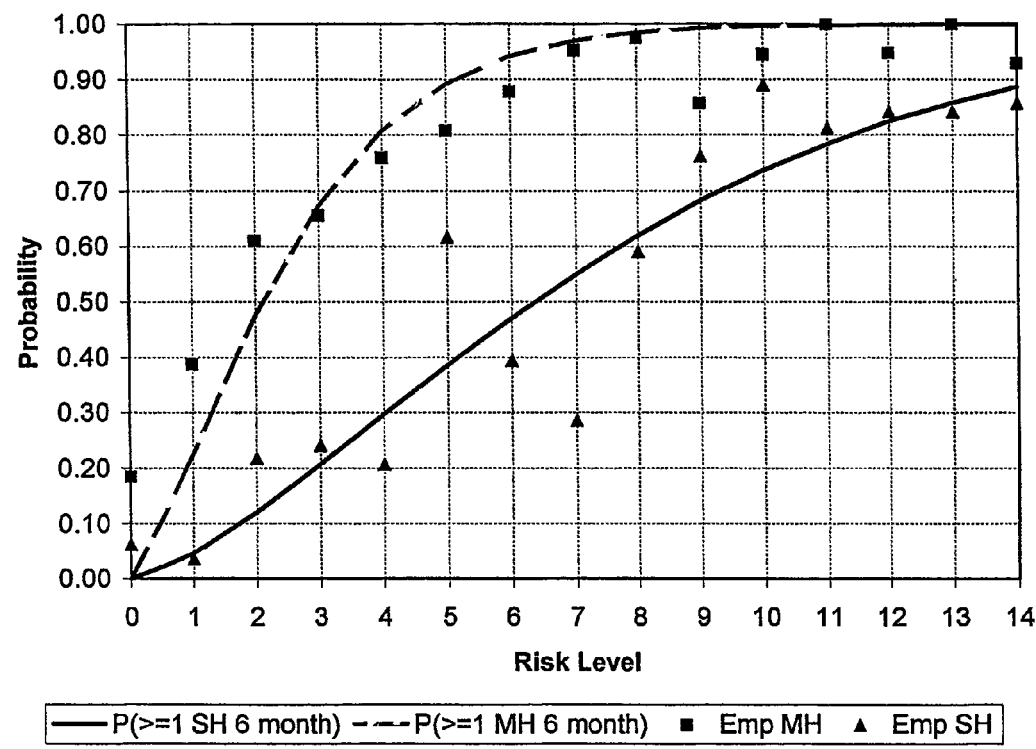
FIG. 3 graphically presents the empirical and theoretical probabilities for moderate (dashed line) and severe (black line) hypoglycemia within six months after the SMBG assessment for each of the 15 categories of risk level defined by the Low BG Index of Example No. 1.

The theoretical probabilities for one or more moderate or severe hypoglycemic episodes are given by the formulas as shown in FIG. 3:

$$P(MH>=1)=1-exp(-exp(-1.3721)*Risk^{**} 1.3511)$$

$$P(SH>=1)=1-exp(-exp(-3.0591)*Risk^{**} 1.4549)$$

FIG. 3 presents the empirical and theoretical probabilities for moderate (dashed line) and severe (black line) hypoglycemia within six months after the SMBG assessment for each of the 15 categories of risk level defined by the Low BG Index.

The coefficients of determination and their square roots are as follows:
SH Model: $D^2$=86%, D=93%.
MH Model: $D^2$=89%, D=95%.

Figure 4:
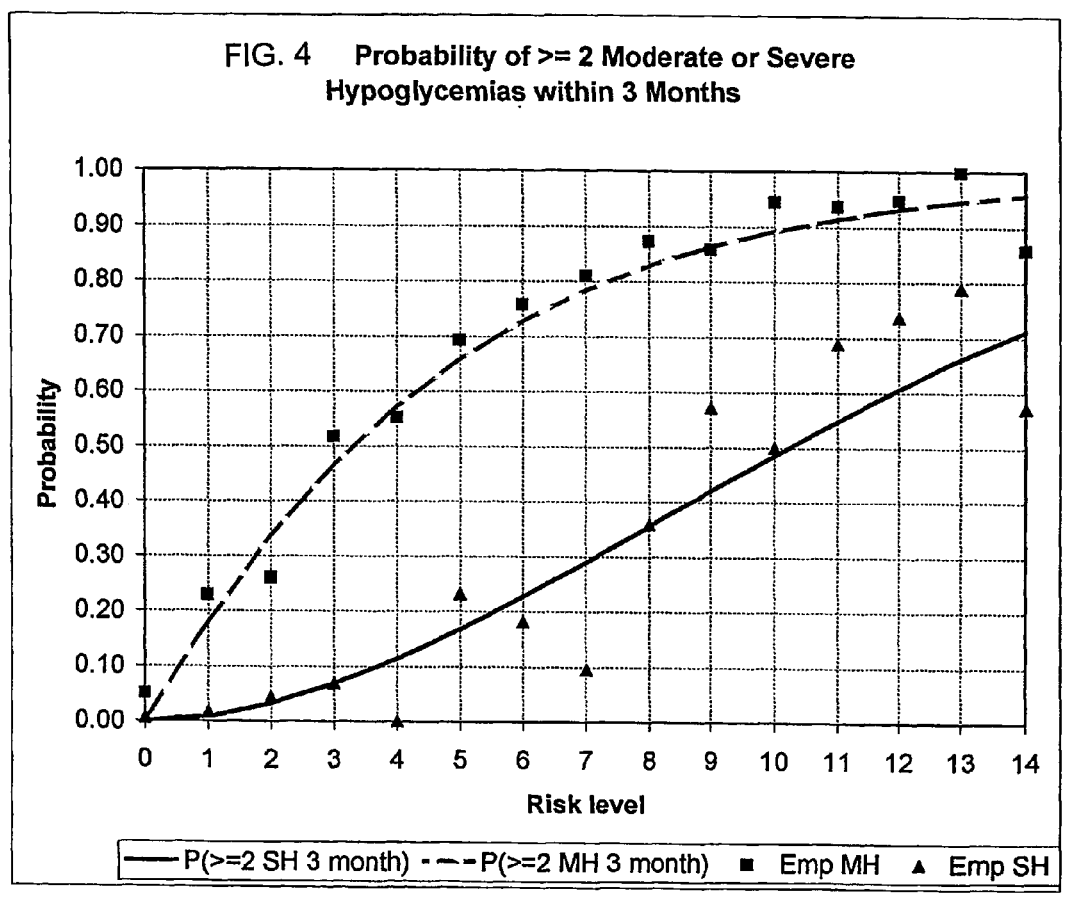
FIG. 4 graphically presents the empirical and theoretical probabilities for 2 or more moderate (dashed line) and sever (black line) hypoglycemic episodes within three months after the SMBG assessment for each of the 15 categories of risk level defined by the Low BG Index of Example No. 1.

The theoretical probabilities for two or more moderate or severe hypoglycemic episodes are given by the formulas as shown in FIG. 4:

$$P(MH>=2)=1-exp(-exp(-1.6209)*Risk^{**} 1.0515)$$

$$P(SH>=2)=1-exp(-exp(-4.6862)*Risk^{**} 1.8580)$$

FIG. 4 presents the empirical and theoretical probabilities for 2 or more moderate (dashed line) and severe (black line) hypoglycemic episodes within three months after the SMBG assessment for each of the 15 categories of risk level defined by the Low BG Index.

The coefficients of determination and their square roots are as follows:
SH Model: $D^2$=98%, D=99%.
MH Model: $D^2$=90%, D=95%.

Figure 5:
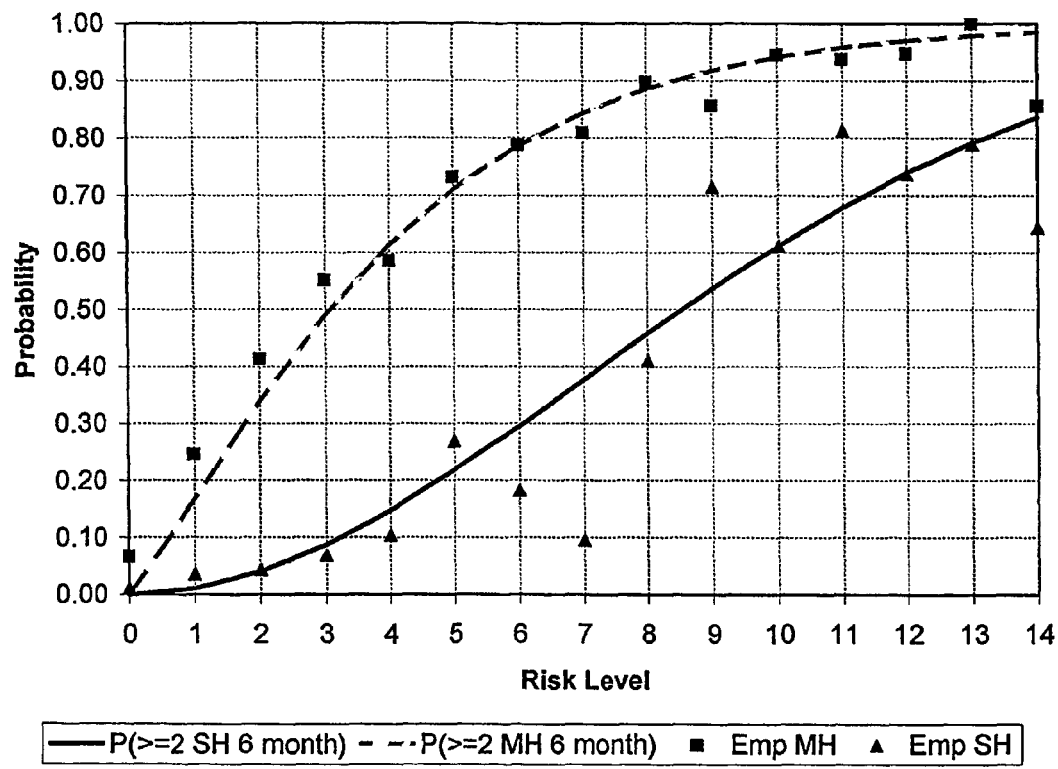
FIG. 5 graphically presents the empirical and theoretical probabilities for 2 or more moderate (dashed line) and severe (black line) hypoglycemic episodes within six months after the SMBG assessment for each of the 15 categories of risk level defined by the Low BG Index of Example No. 1.

The theoretical probabilities for two or more moderate or severe hypoglycemic episodes are given by the formulas as shown in FIG. 5:

$$P(MH>=2)=1-exp(-exp(-1.7081)*Risk^{**} 1.1955)$$

$$P(SH>=2)=1-exp(-exp(-4.5241)*Risk^{**} 1.9402)$$

FIG. 5 presents the empirical and theoretical probabilities for 2 or more moderate (dashed line) and severe (black line) hypoglycemic episodes within six months after the SMBG assessment for each of the 15 categories of risk level defined by the Low BG Index.

The coefficients of determination and their square roots are as follows:
SH Model: $D^2$=98%, D=99%.
MH Model: $D^2$=89%, D=95%.

The theoretical probabilities for three or more moderate or severe hypoglycemic episodes are given by the formulas as shown in FIG. 9:

$$P(MH>=3)=1-exp(-exp(-2.0222)*Risk^{**} 1.2091)$$

$$P(SH>=3)=1-exp(-exp(-5.5777)*Risk^{**} 2.2467)$$

Figure 10:
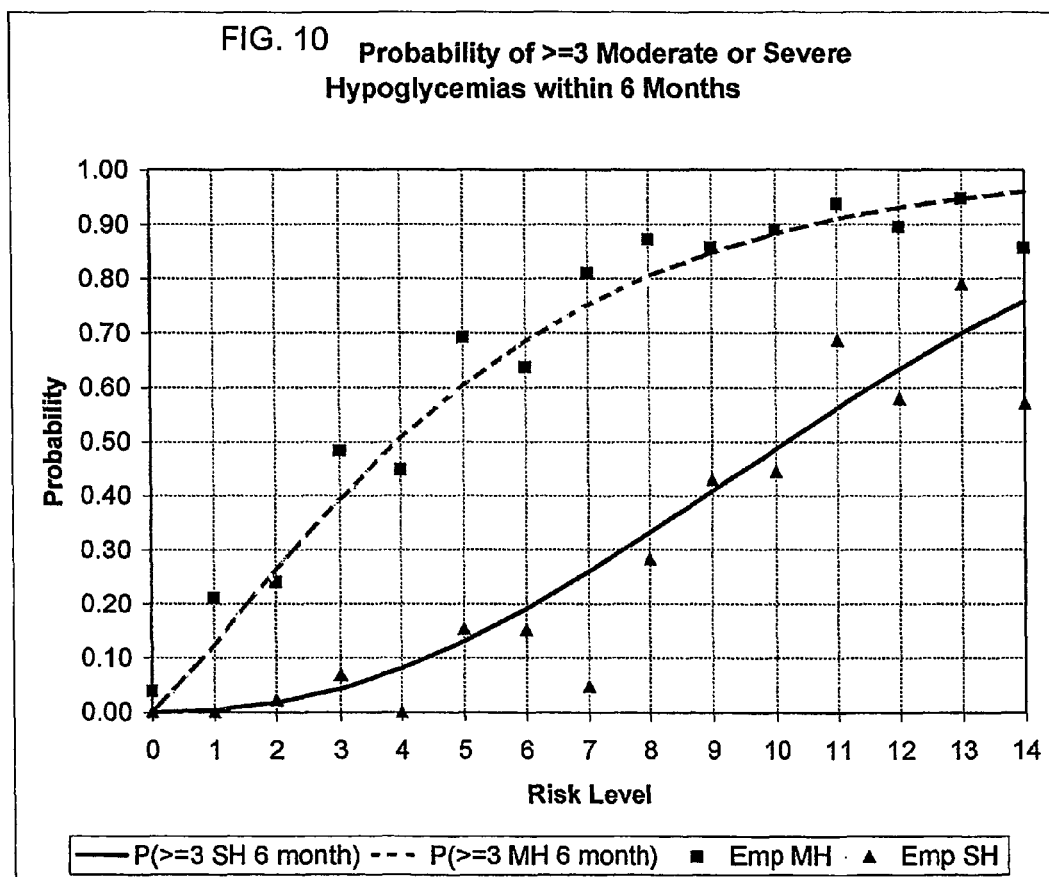
FIG. 10 graphically presents the empirical and theoretical probabilities for 3 or more moderate (dashed line) and severe (black line) hypoglycemic episodes within six months after the SMBG assessment for each of the 15 categories of risk level defined by the Low BG Index of Example No. 1.

FIG. 10 presents the empirical and theoretical probabilities for 3 or more moderate (dashed line) and severe (black line)

hypoglycemic episodes within six months after the SMBG assessment for each of the 15 categories of risk level defined by the Low BG Index.

The coefficients of determination and their square roots are as follows:
SH Model: $D^2$=97%, D=99%.
MH Model: $D^2$=90%, D=95%.

Detailed Results—Training Data Set

The training data set contained SMBG data followed by monthly diaries of severe hypoglycemia. As opposed to the test data set where BSH and BMH were identified by cutoff BG values, the monthly diaries contained report of symptomatic severe episodes defined as unconsciousness, stupor, inability for self-treatment, or significant cognitive impairment due to hypoglycemia. Within 6 months following SMBG the subjects reported on average 2.24 such episodes per person with 67% of the subjects reporting no such episodes. From a statistical point of view, this alone makes the distribution of SH episodes substantially skewed and unsuitable for application of linear methods. Nevertheless linear regression could be used to evaluate the relative contribution of various variables to the prediction of SH, but not for building the final model. We performed the following three analyses:

(1) No knowledge of SH history: Ignoring any knowledge of history of SH, we used regression to predict future SH from baseline $HbA_{1c}$ and SMBG characteristics such as average BG, Low BG Index, and estimated BG risk rate of change (all variables are described in the original invention disclosure). As repeatedly found before, $HbA_{1c}$ and average BG did not have any contribution to the forecast of SH. The final regression model included the Low BG Index and the BG risk rate of change and had the following goodness-of-fit:

| | |
|---|---|
| Multiple R | .61548 |
| R Square | .37882 |
| Analysis of Variance | |
| F = 27.74772 | Signif F = .0000 |

Variables in the Equation

| Variable | B | SE B | Beta | T | Sig T |
|---|---|---|---|---|---|
| LBGI | 4.173259 | .649189 | 2.104085 | 6.428 | .0000 |
| RATE | −5.749637 | 1.091007 | −1.724931 | −5.270 | .0000 |
| (Constant) | −2.032859 | .790491 | | −2.572 | .0117 |

(2) Knowledge of prior SH: When we included the number of SH episodes in the previous year as reported in a screening questionnaire, this variable accounted for an additional 11% of the variance of future SH:

| | |
|---|---|
| Multiple R | .70328 |
| R Square | .49461 |
| Analysis of Variance | |
| F = 29.35999 | Signif F = .0000 |

Variables in the Equation

| Variable | B | SE B | Beta | T | Sig T |
|---|---|---|---|---|---|
| SH | .337323 | .074286 | .375299 | 4.541 | .0000 |
| LDR | −4.350779 | 1.036380 | −1.305264 | −4.198 | .0001 |
| RLO | 3.134519 | .631684 | 1.580371 | 4.962 | .0000 |
| (Constant) | −2.136619 | .717334 | | −2.979 | .0037 |

(3) Without knowledge of the number of prior SH, just knowing whether a person had or did not have prior SH, we were able to account for 45% of the variance of future SH using only SMBG variables;

(4) Finally, two separate linear models accounted for 55% of the variance in daytime SH vs. 25% of the variance in nocturnal SH. The direct correlations of all predictor variables with nocturnal SH were also weaker. Nocturnal episodes represented 30% of all SH.

Figure 13:
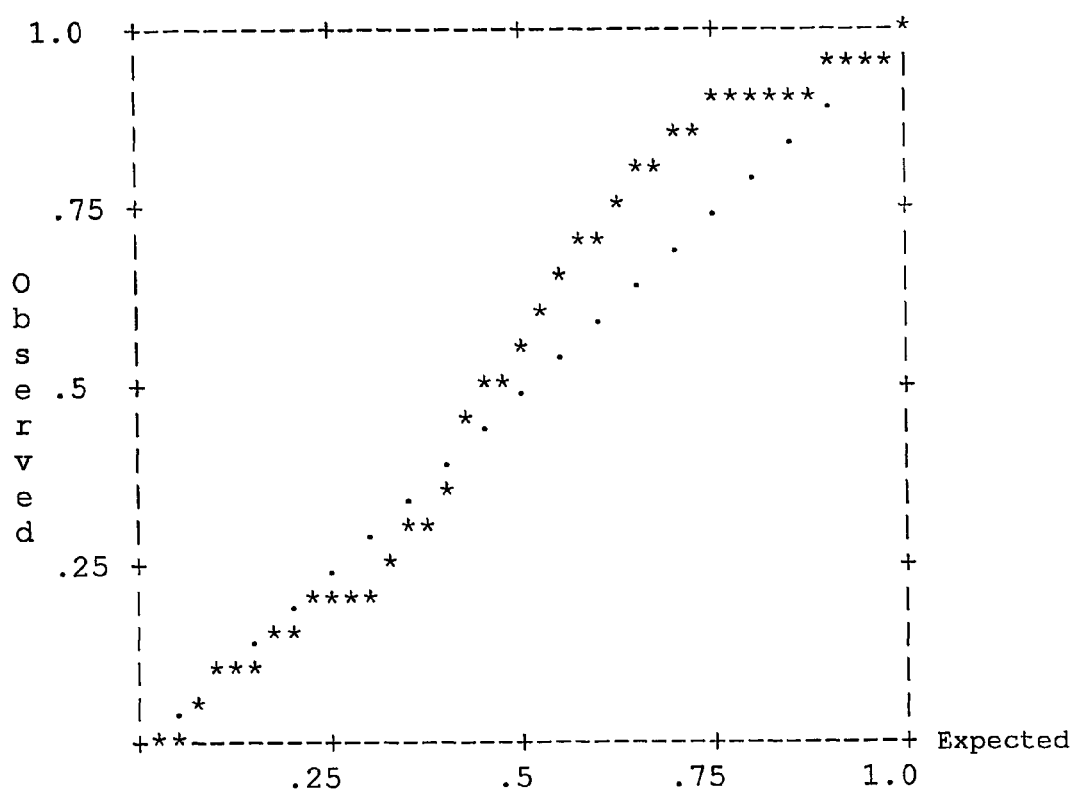
FIG. 13 graphically shows a statistical evidence for that is given by the normal probability plot 1 of Example No. 1.
Figures 18A, 18B:
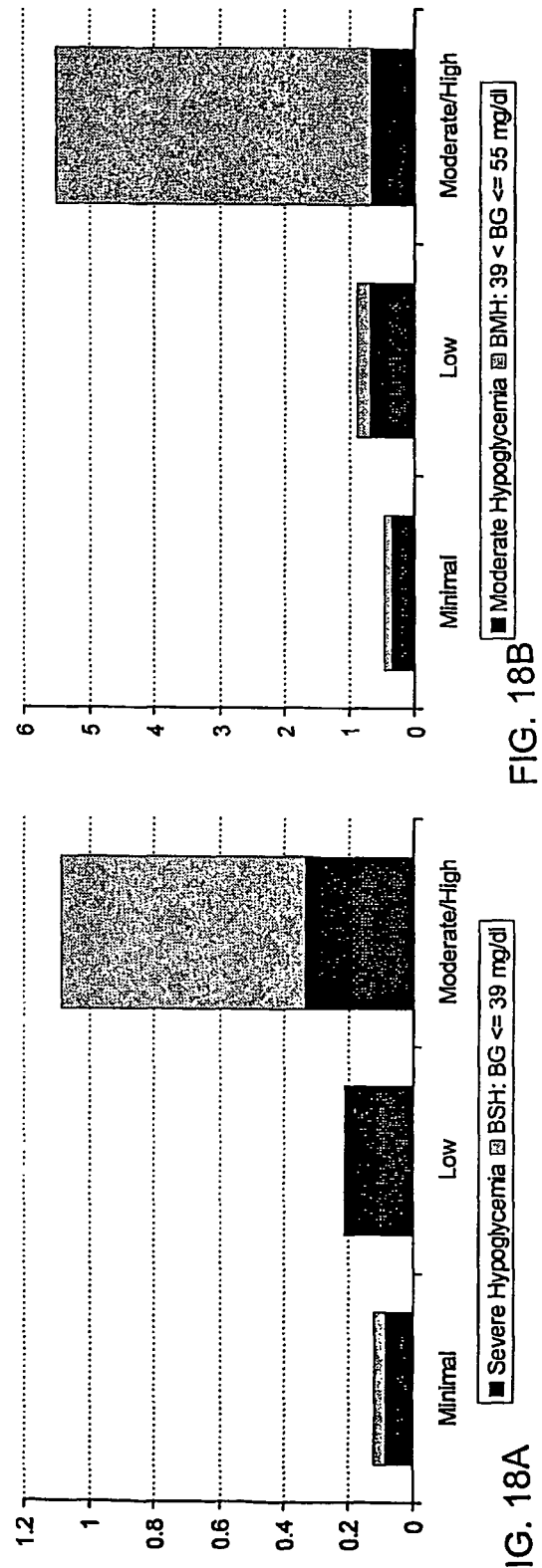
FIGS. 18(A)-(B) graphically present a one-month risk for significant hypoglycemia in T2DM predicted by the LBGI for ANOVA of number of severe hypoglycemic episodes by risk group ($F=6.0$, $p<0.005$) and ANOVA of number of moderate hypoglycemic episodes by risk group ($F=25.1$, $p<0.001$) in Example No. 2.

We conclude that a linear predictive model could directly account for about 40 to 50% of the variance of future SH. However, such a model is not well balanced in terms of its residual errors (which is due to the highly skewed distribution of the number of SH episodes across the diabetic population). A statistical evidence for that is given by the normal probability plot of FIG. 13, which shows a substantial deviation of the standardized residuals from their expected values:

Thus, we adopt another approach to predicting SH based on classification of subjects into risk categories using their SMBG data and estimation of the probabilities for subsequent SH in these categories. We attempted various classification models maximizing the difference between the risk categories and trying to achieve a maximum resolution of risk evaluation (in terms of maximal number of categories).

The best results were achieved by the classification based on the Low BG Index alone that had 15 risk categories (presented in the beginning of the previous section).

In addition to its best separation between categories, this result has other advantages as well: (1) No prior knowledge of history of SH is required; (2) The calculation is relatively simple and does not require tracking of temporal variables such as BG rate of change, and (3) The classification appeared to be equally applicable to both T1DM and T2DM patients (which is coherent with no requirements for knowledge of prior SH).

Algorithm 3: Evaluation of Short-Term Risk for Hypoglycemia

Example No. 1 provides for, but not limited thereto, an optimization of Algorithm 3 in terms of:

(1) Utilization of baseline long-term risk (from Algorithm 2) and $HbA_{1c}$ (from Algorithm 1);
(2) Risk criterion/threshold for hypoglycemia alert;
(3) Frequency of SMBG;
(4) Whether a hypoglycemia alert should be issued if an increased risk for hypoglycemia is detected and there is no SMBG for certain period of time, and
(5) Contribution of demographic variables such as history of severe hypoglycemia.

Introduction

As opposed to Algorithms 1 and 2, which have a longer history of development, Algorithm 3 deals with a proposition that was, until recently, considered impossible. In fact, there is still a general perception that prediction of any future BG value (hypoglycemia in particular) is not possible on the basis of previously known values (Bremer T and Gough D A. Is blood glucose predictable from previous values? A solicitation for data. *Diabetes,* 1999, 48: 445-451.). Our previous work, reported in one manuscript and presented in detail in the invention disclosure available to Lifescan, Inc. disputes this general perception. In order to explain the basis for this dispute and to clarify the reasoning behind Algorithm 3, we include the following paragraph.

Our "philosophy" in quantifying characteristics of diabetes: Hormonal interactions are governed by dynamic-control biochemical networks that have a more or less complex structure of principal nodes and conduits, depending on the studied endocrine system. Diabetes disrupts the network control of insulin-glucose dynamics at various levels. For example, in T1DM the natural production of insulin is completely eliminated, while in T2DM the utilization of insulin in the cell is obstructed by a greater insulin resistance. In T1DM (and frequently in T2DM) some form of external insulin replacement is required, which makes the control system vulnerable to imperfect external factors, including the timing and amount of pill or insulin injection, food eaten, physical activity, etc. This frequently leads to extreme BG excursions into hypoglycemia and hyperglycemia. In many, but not in all cases, hypoglycemia triggers an endocrine response, known as counterregulation. Thus, in mathematical terms, BG fluctuations over time are the measurable result of the action of a complex dynamic system, influenced by a number of internal and external factors. However, it is well known from the theory of dynamical systems that when the complexity of control increases, a purely deterministic system evolves to display random macro-behavior. Consequently, within short periods of time (minutes) the BG fluctuations observed at a human level would be nearly-deterministic, while over longer periods of time the fluctuations would be nearly-random, including extreme transitions, such as SH episodes. Thus, stochastic modeling and statistical inference are most appropriate for analysis of the system over longer periods of time—a paradigm adopted by Algorithms 1 and 2 that use our originally developed measures, such as the LBGI and HBGI, to predict, after a certain observation period, a range of values, or a probability of an event. Over short periods of time BG fluctuations can be modeled and predicted using deterministic networks, which would be the case with future intelligent insulin-delivery devices linked to continuous monitoring.

Algorithm 3 operates in an intermediate time scale of a few hours to a few days and therefore requires a combination of statistical inference and deterministic modeling. The former will be used to assess the baseline risk for SH for an individual, while the latter will be used for a dynamical tracking of individual parameters and forecast of SH episodes prior to their occurrence. When implemented in a device Algorithm 3 would work as follows:

(1) The device collects certain baseline information for the subject and establishes individual baseline parameters;
(2) Then, the device begins tracking a certain set of properties of the SMBG data;
(3) The device is equipped with a decision-making rule that decides when to raise a flag for upcoming SH and when to lower this flag if the data indicate that the threat is reduced;
(4) When the flag is raised, we assume that the subject is warned for SH in the following 24 hours (prediction time).

This dynamical prediction creates theoretical problems at both the level of model parameter optimization and at the level of evaluation of the preciseness of the optimal solution. We will begin with clarifying the second problem, as it is most important for understanding the action of Algorithm 3.

Evaluating the Preciseness of Algorithm 3: While Algorithms 1 and 2 employ a static forecast and the criterion for evaluation of these algorithms is theoretically apparent—a better predictive value, with Algorithm 3 the optimization criterion is no longer straightforward. This is because by increasing the percentage of predicted SH episodes, we unavoidably increases the number of "raised flags," which in turn increases the number of potential "false alarms." The matter is additionally complicated by the fact that a "false alarm" is not clearly defined. In its pure form, a false alarm would be a raised flag that is not followed by and SH episode. However, SH could be avoided if the person perceives symptoms and takes an appropriate action. Thus, even if the biochemical potential for SH may present, an event may not occur. In order to deal with this problem we adopt the following optimization criterion:

(1) Maximize the prediction of upcoming SH within 24 hours;
(2) Minimize the ratio $R_{ud}$ of duration periods of "flag up" to "flag down".

While the first of these two points is clear, the second may need an additional explanation. Looking from the perspective of an implementation of Algorithm 3 in a meter, at every SMBG determination the meter decides whether to raise a flag or not to raise a flag for upcoming SH. When the flag is raised, it may stay up for some time (along several subsequent SMBG readings) until a decision is made to take the flag down. Thus, we will have an alternating process of "flag up" and "flag down" with the changes happening at points of SMBG. The ratio $R_{ud}$ referred to in point (2) above, is the average time for a person, counted while the flag is up, divided to the average time counted while the flag is down.

Our previous best result presented in the Invention disclosure was a prediction of 44% of SH episodes within 24 hours, and $R_{ud}=1:7$, e.g. one day of high-risk alert was alternating with 7 days of no alert. Since at that time we assumed that the warning period was at least 24 hours, the algorithm was optimized to raise a flag no more frequently than once a week. Given that this analysis was done using data for subjects who were experiencing high rate of SH episodes, this ratio was considered acceptable.

During Example No. 1 of this study we had to use the same data set for refinement of Algorithm 3 since there is no other data available that include simultaneous SMBG records and records of SH. We also used a similar criterion to evaluate the preciseness of Algorithm 3. However, we changed substantially everything else. The tracking of the data, the parameter estimation, all threshold values and the decision-making rule are no longer the same. These changes were caused by a new idea that SH is preceded by certain "depletion" of the body's reserves to counterregulate and that this depletion can be tracked by using SMBG data. The exact implementation of this idea is described in the section "Decision-making Rule." Since the decision-making rule involves a continuous criterion and a somewhat artificial cutoff, several solutions are presented and one is selected as optimal for further investigation. However, upon presentation of these results, we may decide to select another solution to be implemented in future applications of Algorithm 3.

Summary of the Results

First, it is important to note that all results presented below go well beyond statistical significance. As we will see in a few examples in the next section, the observed differences are always highly significant (with p-values below any imaginable significance level). The point of Algorithm 3 is to predict occurrence of SH episodes on an individual basis. The results are:

(1) The minimum baseline observation period is 50 SMBG readings taken over approximately two weeks with a frequency of 3-4 readings a day. After this time each subject is classified in one of two risk groups that later use different decision-making rules;

(2) From the 6 months of data that we have we find that it is sufficient to make this group assignment once in the beginning of observation. Thus, we can assume that about every 6 months the meter would use 50 reading to reevaluate its owner's group assignment;

(3) The optimal lag of SMBG tracking is 100 to 150 readings taken with a frequency of 3-4 readings per day. In other words, the optimal decision-making criterion would be based on a computation using all 150 readings in a meter's memory. This was done to simulate the memory capacity of ONE TOUCH ULTRA. In general, good results are achieved using a lag of only 20 readings taken over a week, but a longer lag yields better prediction;

(4) The decision-making rules is based on a new computational procedure that tracks subjects Low BG Index and other related parameters using "provisional mean" computation. Special software was designed to implement this procedure and to process the data that we had available. From a programming point of view, the code needed for implementation of this procedure is only about 20 lines, which includes the computation of the LBGI;

(5) Several decision-making rules (using various parameters) were investigated. Regardless of the frequency of SMBG, these rules achieved prediction of SH within 24 hours anywhere from 43.4% with $R_{ud}$=1:25 to 53.4% with $R_{ud}$=1:7. Thus, compared to our previous result, the prediction of SH within 24 hours increased by 10%;

(6) As an optimal solution for further investigation we choose the decision-making rule that predicted 50% of SH within 24 hours and had $R_{ud}$=1:10. The following results refer to this optimal solution under different conditions:

(7) The optimal frequency of SMBG is 4 readings per day. If this frequency is achieved, the prediction of SH within 24 hours increases to 57.2% with the same $R_{ud}$=1:10. Other frequencies of SMBG are investigated and reported as well;

(8) If we extend the prediction period to 36, or 48 hours, the prediction of SH increases to 57% and 63% respectively, with the same $R_{ud}$=1:10;

(9) Utilizing baseline information increases substantially the prediction of SH. In fact, the 10% increase over our previous version of Algorithm 3 is entirely due to the use of baseline tracking. However, this baseline tracking is now modeled as a two-week period of self-calibration of the meter that does not use any additional input from the subject;

(10) Personal/demographic information, such as history of SH or prior $HbA_{1c}$, does not contribute to a better short-term prediction of SH;

(11) Raising a flag whenever there is a prolonged period of no SMBG activity is not justified. The only times when the meter would issue warning for upcoming SH would be the times of usage. This is because a major part of the prediction of SH is based on the recurrence (clustering) of very low BGs. An assessment of this recurrence is presented in an abstract (Kovatchev et al. Recurrent Hypoglycemia and Severe Hypoglycemia (SH) in T1DM Patients With History of Multiple SH) prepared for the June 2002 ADA meeting (See Appendix).

Detailed Description of the Data Processing

The meter stores SMUG readings together with the date and exact time (hour, minute, second) of each reading. Thus, in Training Data set 2 we have for each subject a certain temporal sequence of SMBG records. During the study, a total of 75,495 SMBG readings (on average 4.0±1.5 per subject per day) were downloaded from the participants' memory meters. From subjects' monthly diaries, we had the date and time of SH episodes that had occurred. Subjects reported 399 (4.7±6.0 per subject) SH episodes. Sixty-eight (80%) of the participants experienced one or more episodes of SH. These subjects did not differ from those who did not experience SH (the remaining 20% of the subjects) in terms of any of their demographic characteristics.

Pre-Processing of the Data: Special software was developed for pre-processing of the data. This included: (1) Assembling of the memory meter data for each subject into a continuous 6-8-month sequence of BG readings, and (2) Matching of each subject's records of SH with this sequence by date and time. The latter was performed as follows: for each SMBG reading the time (hours/minutes) until the nearest SH episode, and the time elapsed from the latest SH episode, were computed. Thus, it was possible to: (1) time 24-hour, 48-hour, etc. periods backward and forward from each SH episode, and (2) time periods between SMBG readings. Due to the nature of SH (stupor, unconsciousness), no SMBG was performed exactly at the time of SH, thus SH episodes for the purposed of Algorithm 3 do not include biochemical significant hypoglycemia that was used for Algorithm 2. The average per SH episode minimum elapsed time between SH and the nearest preceding SMBG reading was 5.2±4.1 hours; 29 SH episodes (7%) were preceded by a SMBG reading within 15 minutes. For each SH episode, we counted how many SMBG readings were performed within 24 h, 36 h, 48 h, and 72 h prior to that episode.

Computing of Baseline Risk Values and Self-Calibration: The Low BG Index for each subject is computed on his/her first SNBG readings. It was determined that the minimum number of reading required to compute a baseline LBGI is 50 taken over approximately 2 weeks. Therefore for each new meter we need to anticipate an initial two-week self-calibration period during which the meter would be scanning the overall risk for SH of its owner. After the initial period, the person is classified into one of two risk groups: Low-moderate risk (LBGI≦3.5, LM Group) or moderate-to-high risk (LBGI>3.5, MH Group). Our test data show that a more precise classification would not be necessary. This classification allows for different decision-making rules to be used in the LM and MH groups and raises the hit rate of the algorithm by approximately 10% as compared to its original hit rate presented in the invention disclosure.

With the test data re-calibration of the baseline risk was not necessary. Thus, we can assume that if the person does not undergo changes in treatment, re-calibration would be performed approximately every 6 months. This is consistent with the results of Algorithm 2 showing that the long-term prediction of SH is quite valid for 6 months after the initial observation period.

However, if the person experiences rapid changes in his/her glycemic control, re-calibration maybe required more frequently. The decision for re-calibration can probably be automated and based on observed increasing differences between the running risk value (see the next paragraph) and the baseline LBGI. However, the available data do not allow us to clarify this issue since the subjects that we observed did not have substantial changes in their risk for hypoglycemia.

Computing SMBG Parameters: After the pre-processing step, another piece of software was designed to compute SMBG parameters that would be used for prediction of imminent SH. This software included:

(1) Computing of a Low BG Risk value (RLO) for each BG reading that is done by the following code (here BG is measured in mg/dl, if the units are mmol/l the coefficients are different):

```
scale=(ln(bg))**1.08405 − 5.381
risk=22.765*scale*scale
if (bg_1 le 112.5) then
    RLO=risk
else
    RLO=0
endif
```

(2) For each SMBG reading with a sequential number n, BG(n), computing of a running value of the LBGI(n), and another statistics, SBGI(n) that is the standard deviation of the low BG risk values. These two parameters were computed with a certain lag (k) backwards from each SMBG reading, e.g. included that reading, BG(n), and (k−1) readings taken prior to BG(n).

(3) The computation of LBGI(n) and SBGI(n) used a new provisional means procedure that is based on the following recursive code:
Initial values at n−k (or at the max (1,n−k) to be exact in order to account for meter readings with a sequential number less than k):

$LBGI(n-k)=rlo(n-k)$ $rlo2(n-k)=0$

Values for any consecutive iteration j between n−k and n:

$LBGI(j)=((j-1)/j)*LBGI(j-1)+(1/j)*RLO(j)$ $rlo2(j)=((j-1)/j)*rlo2(j-1)+(1/j)*(RLO(j)-LBGI(j))**2$ After this cycle is completed we have the value of LBGI (n) and we compute $SBGI(n)=sqrt(rlo2(n))$ Since the maximum of n is 150 for ONE TOUCH ULTRA meters, the search for an optimal lag k was performed within the range of k=10 to k=150. Although the difference in performance was not significant, the optimal lag was determined to be k=150 (see the next section for examples).

Decision-Making Rule: At each SMBG reading the procedure decides whether to raise a flag warning for upcoming SH, or not. If the flag is raised, the procedure decides whether to bring it down. These decisions depend on three threshold parameters, $\alpha, \beta, \gamma$ that work as follows:

For subject at low-to-moderate risk (LM group):
FLAG=0
if $(LBGI(n) \geq \alpha$ and $SBGI(n) \geq \beta)$ FLAG=1
if $(RLO(n) \geq (LBGI(n)+\gamma*SBGI(n)))$ FLAG=1

For subjects in the moderate-to-high risk group only the second if-statement is active. In other words, the flag is raised (e.g. becomes equal to 1) if both the running value of LBGI(n) and its standard deviation SBGI(n) exceed certain threshold values, and is also raised if the current value of the low BG risk RLO(n) exceeds the value of LBGI(n) plus $\gamma$ standard deviations.

An heuristic explanation: The values of LBGI(n) and SBGI(n) reflect slower changes in risk for hypoglycemia—it takes a few days of SMBG to substantially change these values. Since elevated LBGI(n) means more frequent and extreme recent hypoglycemia, we can conclude that LBGI(n) and SBGI(n) reflect a persistent depletion (or lack of replenishment) of counterregulatory reserves over the course of several days. In addition, SBGI(n) is a marker, of the stability of the system—a larger SBGI(n) indicates that a subjects' BG fluctuations increase and therefore the control system becomes unstable and vulnerable to extreme aberrations. Thus, the first logical expression reflects the notion that SH occurs whenever the couterregulatory defenses are exhausted and the controls (external or internal) become unstable. The second logical expression accounts for acute changes in the low BG risk, triggering a flag whenever the current Low BG risk value is suddenly becomes greater than its running average. The fact that for subjects in the moderate-to-high risk group only the second logical expression is relevant goes along with these subjects' eventual "permanent depletion" and "permanent instability" status. Since these subjects continuously run low BG values, and their BG is unstable, any acute hypoglycemic episode would be capable of triggering SH. In general, a flag for severe hypoglycemia is raised either after a period of low unstable BG, or after an acute hypoglycemic event that deviates substantially (in a risk space) from the latest running risk average (that maybe already high). It follows that SH episodes that are not preceded by any of these warning signs will remain unaccounted for by this algorithm. Below in Table 5C we present a sample output that illustrates the action of Algorithm 3 for several subjects:

TABLE 5C

A Sample Output that Illustrates the Action of Algorithm 3 for Several Subjects:

| ID | BG | SH | FLAG | TIME | Here $\alpha = 5, \beta = 7.5, \gamma = 1.5$ |
|---|---|---|---|---|---|
| 135 | 70 | .00 | .00 | 53.75 | For subject # 135 the first flag is raised |
| 135 | 77 | .00 | .00 | 41.09 | about 30 hours prior to SH and stays up for |
| 135 | 124 | .00 | .00 | 35.02 | the next reading whish is taken 16 hours |
| 135 | 51 | .00 | 1.00 | 30.44 | later and 14 hour prior to SH. This latter |
| 135 | 50 | .00 | 1.00 | 14.72 | reading and the two readings that follow |
| 135 | 66 | .00 | <24 h | 10.60 | are within 24 hours prior to SH, so we |
| 135 | 49 | .00 | 1.00 | 8.30 | consider this episode to be predicted. |
| 135 |  | 1.00 |  |  | Nevertheless, the flag is brought up again about 8 hours and 20 minutes prior to SH. |
| 135 | 97 | .00 | .00 | 140.05 | A second SH episode for this subject is |
| 135 | 130 | .00 | .00 | 25.17 | flagged 36 minutes in advance. |
| 135 | 59 | .00 | .00 | 20.20 |  |
| 135 | 76 | .00 | .00 | 5.23 |  |
| 135 | 41 | .00 | 1.00 | .62 |  |

TABLE 5C-continued

A Sample Output that Illustrates the Action of Algorithm 3 for Several Subjects:

| ID | BG | SH | FLAG | TIME | Here α = 5, β = 7.5, γ = 1.5 |
|---|---|---|---|---|---|
| 135 |  | 1.00 |  |  |  |
| 219 | 200 | .00 | .00 | 40.72 | This subject gets two warnings - |
| 219 | 64 | .00 | .00 | 37.88 | approximately 28.7 and 11.2 hours prior to |
| 219 | 43 | .00 | 1.00 | 28.73 | this SH episode. |
| 219 | 225 | .00 | .00 | 16.22 |  |
| 219 | 38 | .00 | 1.00 | 11.18 |  |
| 219 | 43 | .00 | <24 h | 10.87 |  |
| 219 | 75 | .00 | <24 h | 4.52 |  |
| 219 |  | 1.00 |  |  |  |
| 222 | 156 | .00 | .00 | 19.08 | This subject gets a warnings approximately |
| 222 | 176 | .00 | .00 | 13.23 | 4 hours and 45 minutes prior to this SH |
| 222 | 83 | .00 | .00 | 9.72 | episode. |
| 222 | 66 | .00 | .00 | 7.83 |  |
| 222 | 42 | .00 | 1.00 | 4.75 |  |
| 222 |  | 1.00 |  |  |  |
| 223 | 228 | .00 | .00 | 18.80 | This subject experienced two recurrent SH |
| 223 | 149 | .00 | .00 | 14.15 | episodes within 12 hours. The flag is raised |
| 223 | 41 | .00 | 1.00 | 5.85 | approximately 6 hours before the first |
| 223 |  | 1.00 |  |  | episode and therefore we consider both |
| 223 | 110 | .00 | <24 H | 6.00 | episodes to be in the predicted risk high- |
| 223 |  | 1.00 |  |  | risk 24-hour tume period. |

Each line of this output presents an SMBG reading, or an SH episode (without a reading). ID is subject's ID number, BG is BG level in mg/dl, SH=1 whenever SH episode occurs. FLAG=1 if Algorithm 3 decides to raise the flag; TIME is the time to the nearest SH episode in hours.

Optimizing the of Lag of the Provisional Means Procedure: In a prior publication we have reported that in the period 48 to 24 hours before SH the average BG level decreased and the BG variance increased. In the 24-hour period immediately preceding SH average BG level dropped further, the variance of BG continued to increase, and there was a sharp increase in the LBGI. In the 24-hour period following SH, average BG level normalized, however the BG variance remained greatly increased. Both the average BG and its variance returned to baseline levels within 48 hours after SH (see Kovatchev et al. Episodes of Severe Hypoglycemia in Type 1 Diabetes are Preceded, and Followed, within 48 Hours by Measurable Disturbances in Blood Glucose. *J of Clinical Endocrinology and Metabolism*, 85: 4287-4292, 2000). We now use these observations to optimize the lag of the provisional means procedure, k, employed by Algorithm 3 on the basis of the deviations in the average values of LBGI(n) and SBGI(n) observed within 24 hour prior to SH. In short, the lag for computing LBGI(n) and SBGI(n) was chosen to maximize the difference that these measures display within 24 hours prior to SH compared to the rest of the study, excluding periods immediately after SH when the system is out of balance. The optimal lag was found to be k=150. Tables 6A and 6B present the means of LBGI(n) and SBGI(n) for several values of the parameter k. and for both subject groups, low-moderate risk and moderate-high risk. It is evident that the difference between various values of k is not great, thus in a practical application any value of k≧10 would be appropriate. However, based on the current data we would recommend k=150, and all further computations use this lag. This recommendation is also based on the reduced variance in LBGI(n) and SBGI(n) at larger lag values, that is reflected by larger t-values below:

TABLE 6A

LBGI(n) within 24 hour prior to SH vs. the rest of the time for different lags:

| LBGI | Low-moderate risk (LM Group) | | | | Moderate-high risk (MH Group) | | | |
|---|---|---|---|---|---|---|---|---|
|  | 24 h prior SH | Rest of the time | t | p | 24 h prior SH | Rest of the time | t | p |
| k = 10 | 4.99 | 3.32 | 9.2 | <.000... | 6.94 | 5.28 | 11.0 | <.000... |
| k = 20 | 4.73 | 3.34 | 9.4 | <.000... | 6.56 | 5.32 | 11.0 | <.000... |
| k = 30 | 4.54 | 3.35 | 9.1 | <.000... | 6.50 | 5.34 | 11.3 | <.000... |
| k = 50 | 4.53 | 3.34 | 9.8 | <.000... | 6.54 | 5.36 | 11.7 | <.000... |
| k = 100 | 4.45 | 3.29 | 11.2 | <.000... | 6.53 | 5.40 | 12.3 | <.000... |
| k = 150* | 4.46 | 3.26 | 12.1 | <.000... | 6.56 | 5.41 | 12.9 | <.000... |

TABLE 6B

SBGI(n) within 24 hour prior to SH vs. the rest of the time for different lags:

| SBGI | Low-moderate risk (LM Group) | | | | Moderate-high risk (MH Group) | | | |
|---|---|---|---|---|---|---|---|---|
| | 24 h prior SH | Rest of the time | t | p | 24 h prior SH | Rest of the time | t | p |
| k = 10 | 7.50 | 5.35 | 9.0 | <.000... | 9.64 | 7.78 | 11.4 | <.000... |
| k = 20 | 8.31 | 6.28 | 10.1 | <.000... | 10.36 | 8.91 | 10.7 | <.000... |
| k = 30 | 8.50 | 6.68 | 9.5 | <.000... | 10.82 | 9.38 | 11.5 | <.000... |
| k = 50 | 8.78 | 7.04 | 10.0 | <.000... | 11.30 | 9.80 | 12.3 | <.000... |
| k = 100 | 9.19 | 7.33 | 11.7 | <.000... | 11.69 | 10.18 | 13.5 | <.000... |
| k = 150* | 9.42 | 7.42 | 13.7 | <.000... | 11.88 | 10.33 | 15.1 | <.000... |

*Optimal solution

As seen in Tables 6A and 6B both LBGI and SBGI become highly significantly elevated in the 24-hour periods preceding SH. Thus, one is tempted to run a direct discriminant or logistic model to predict upcoming SH. Unfortunately such standard statistics don't work very well, although both models are highly statistically significant. The discriminant model (that worked better than logistic regression) predicted correctly 52.6% of upcoming SH episodes. However, its flag-up to flag-down ratio was quite poor $-R_{ud}=1:4$. Therefore this model was biased towards the larger amount of data points, a bias that is to be expected in any statistical procedure. Consequently, we had to employ the decision-making rule presented above.

Accuracy of Prediction of Severe Hypoglycemia

Optimization of the Threshold Parameters $\alpha$, $\beta$, and $\gamma$: Below we present a detailed account of the predictive power of Algorithm 3 using various combinations of its threshold parameters $\alpha$, $\beta$, and $\gamma$. Since the relationship between these parameters and the desired outcome (high prediction of SH and minimal ratio $R_{ud}$) is quite complex, the optimization procedure that we used did not reach a single solution. Also, it seems that there is no need for a single solution either. It is probably a business, rather than mathematical decision, what would be an acceptable % of prediction of SH, given a "flag up" to "flag down" ratio. Thus, we do not claim that any of the presented below solution is optimal. However, in order to explore this subject further, we accept that a 50% prediction of future SH with $R_{ud}=1:10$ is a base for investigating other than 24 hours prediction periods as well as various requirements for the number of SMBG readings per day required for a better risk profile.

Table 7 presents the performance of Algorithm 3 at several combinations of the values of $\alpha$, $\beta$, and $\gamma$ that are representative for the relationship between the percentage of predicted SH (hit rate) and the ratio $R_{ud}$ which we could call "annoyance index." Table 7 also includes the average total time (in days) per subject spent in alert vs. no-alert status during the study, i.e. the summary result from the alternating process of warning-no-warning periods that a subject would experience using this algorithm which illustrates the meaning of the ratio $R_{ud}$.

TABLE 7

Prediction of SH: Hits, Annoyance Index, and Average Times:

| | | | | | Total for study (days) | |
|---|---|---|---|---|---|---|
| α | β | γ | % Hit | $R_{ud}$ | Flag up | Flag Down |
| 6.4 | 8.2 | 1.5 | 43.4 | 1:25 | 7.8 | 198.9 |
| 6.0 | 7.5 | 1.5 | 45.2 | 1:20 | 9.6 | 197.3 |

TABLE 7-continued

Prediction of SH: Hits, Annoyance Index, and Average Times:

| | | | | | Total for study (days) | |
|---|---|---|---|---|---|---|
| α | β | γ | % Hit | $R_{ud}$ | Flag up | Flag Down |
| 5.5 | 7.5 | 1.5 | 47.2 | 1:15 | 12.9 | 194.1 |
| 5.0 | 7.5 | 1.5 | 49.9 | 1:10 | 19.0 | 190.1 |
| 5.0 | 7.5 | 1.3 | 51.3 | 1:9.5 | 19.5 | 185.7 |
| 4.9 | 7.0 | 1.2 | 53.1 | 1:8.4 | 21.6 | 182.0 |
| 4.8 | 7.0 | 1.2 | 53.4 | 1:7 | 25.5 | 178.2 |

The highlighted solution is used for all further analyses. Given that the participants in this study experienced 4.7 SH episodes on average, 19 days of high-alert periods seem to be acceptable, if these alerts would prevent 50% of SH. In addition, high-alert periods tend to come in clusters. Therefore we can assume that in practice, long and relatively calm periods will alternate with a few days of high-risk warnings. The last line in Table 7 presents a solution with a $R_{ud}=1:7$, which is equivalent to the solution presented in the invention disclosure. However, the current solution has almost 10% higher hit rate, 53.4% compared to 44% in our previous algorithm. When the hit rate is comparable to our previous algorithm, the annoyance ratio is below 1:20, i.e. three times better.

FIG. 14 presents the smoothed dependence between the hit rate and the ratio $R_{ud}$ expressed in percentage. It is evident that the ratio between "flag up" and "flag down" increases rapidly when the hit rate of Algorithm 3 increases. Thus, given these data it maybe unjustified to pursue parameter combinations resulting in a higher than 50% hit rate:

Alternative Prediction Periods: In the beginning of the description of Algorithm 3 we made the basic assumption that an SH episode would be considered predicted if the flag is raised within the 24-hour period of time preceding this episode. This assumption resulted in the hit rates reported in the previous section. We will now present computations of the hit rate based on other prediction periods ranging from 12 to 72 hours. Throughout this experiment the parameters $\alpha$, $\beta$, and $\gamma$ remain fixed at 5.0, 7.5, and 1.5 respectively, i.e. at their values in the solution highlighted of Table 7. Therefore the flag-up rate remains the same as in this solution with $R_{ud}=1:10$, and only the hit rate changes since we change the definition of a hit. FIG. 15 presents the dependence between the prediction period and the corresponding hit rate.

It is evident that the hit rate increases rapidly with the increase of the prediction period to about 24 hours and then the increase of the hit rate gradually slows down. Therefore, we can conclude that 24 hours ahead is an optimal and a reasonable forecast period.

Optimal Number of SMBG Readings Per Day. Finally we experiment with the requirement of how many readings per day are needed in order to produce an optimal forecast of SH.

As we said in the beginning, all reported SH episodes were 399. Of these episodes 343 had any SMBG reading available in the preceding 24 hours (additional 3 episodes had any reading within the preceding 48 hours and additional 4 episodes had any reading within the preceding 72 hours). It follows that more than 50 SH episodes (14%) did not have any reasonable preceding SMBG reading that would help with their prediction. The 343 episodes that had at least one prior SMBG reading within 24 hours were used for the computation of the hit rates in the previous section. The other episodes were naturally excluded from the computation.

Further analysis shows that the hit rate increases rapidly with the number of readings taken before an SH episode. However, if we impose a strict requirement for a certain number of readings to be available in order to consider an SH episode, we see that the number of SH episodes that meet this requirement rapidly decreases (Table 8). This is due to subjects' non-compliance with the study requirements and is maybe a good reason to incorporate in future meters some sort of a warning message that Algorithm 3 will not be useful and would be switched off if there are no SMBG readings taken at an appropriate rate.

Table 8 presents the number of SH episodes that had available certain number of preceding SMBG readings and the hit rate of Algorithm 3 for these episodes. The highlighted row of the table contains the optimal solution from Table 7 that was used as a base for all subsequent computations. All hit rates are given in terms of a 24-hour prediction period, i.e. flag within the 24 hours preceding SH. We can conclude that with an increased subjects' compliance the accuracy of Algorithm 3 in prediction SH would increase substantially. With 5 SMBG reading per day the accuracy is up 10% from its base of 50% hit:

TABLE 8

Performance of Algorithm 3, Given a Certain Number of Prior SMBG Readings

| Number of Preceding SMBG Readings | SH episodes that satisfy the requirement in column 1 (% of total number of SH) | Hit Rate |
|---|---|---|
| At least 1 within 24 hours | 343 (86%) | 49.9% |
| At least 3 within 24 hours | 260 (65%) | 54.2% |
| At least 4 within 24 hours | 180 (45%) | 57.2% |
| At least 5 within 24 hours | 103 (26%) | 64.1% |
| At least 4 within 36 hours | 268 (67%) | 52.6% |
| At least 5 within 36 hours | 205 (51%) | 54.6% |
| At least 6 within 36 hours | 146 (37%) | 60.3% |
| At least 7 within 36 hours | 107 (27%) | 60.7% |
| At least 6 within 48 hours | 227 (57%) | 53.3% |
| At least 7 within 48 hours | 187 (47%) | 54.0% |
| At least 8 within 48 hours | 143 (36%) | 55.9% |
| At least 9 within 48 hours | 107 (27%) | 59.8% |

Other Potential Enhancements That Were Tested

The attempts to increase the predictive power of Algorithm 3 by inclusion of external parameters, such as number of SH episodes in the previous year, or baseline HbA1c were unsuccessful. Evidently, the short-term prediction of SH is mainly dependent on current or recent events. However, a limitation of this study is that all participating subjects had a history of $\geq 2$ SH episodes in the previous year.

Finally, we tested whether an alert for SH should be issued if an increased risk for hypoglycemia is detected and there is no SMBG for certain period of time. This was done in an attempt to predict at least some of the SH episodes that were not preceded by any SMBG readings. This was not successful, generating predominantly false alarms. This result comes as an additional confirmation of the importance of compliance with an SMBG protocol comprised of sufficiently frequent SMBG readings.

Appendix: Abstract

Example No. 1 evaluates the frequency of recurrent hypoglycemia and SH (defined as stupor or unconsciousness that preclude self-treatment) following a low blood glucose (BG<3.9 mmol/l) episode.

Eighty-five patients (41 female) with T1DM and history of >2 episodes of SH in the last year performed SMBG 3-5 times per day for 6 to 8 months and recorded in diaries any SH episodes by date and time. Subjects' average age was 44±10 years, duration of diabetes 26±11 years, $HbA_{1c}$ 7.7±1.1%.

All SMBG readings (n=75,495) were merged by date and time with subjects' SH episodes (n=399; SH events generally do not have a corresponding SMBG reading). For each SMBG reading, or SH episode, the elapsed time since the nearest previous low BG (<3.9 mmol/l) was computed. Table 9 below presents the percentage of readings in 3 hypoglycemic ranges: BG<1.9 mmol/l, 1.9-2.8 mmol/l, and 2.8-3.9 mmol/l, as well as the percentage of SH episodes, that were preceded by a Low BG reading (BG<3.9 mmol/l) within 24 hours, 24-48 hours, 48-72 hours, and more than 72 hours. The last column presents Runs tests rejecting the hypotheses that the days containing low BG readings (or SH episodes) are randomly distributed across time. The negative Z-values of the tests show "clustering" of days with and without hypoglycemic readings or SH episodes.

TABLE 9

Percentage of hypoglycemia/SH preceded by a low BG:

| BG | <24 h. | 24-48 h. | 48-72 h. | >72 h. | Runs Test Z | p-level |
|---|---|---|---|---|---|---|
| <3.9 mmol/l | 50% | 21% | 10% | 19% | −13.6 | <.0001 |
| 2.8-3.9 mmol/l | 52% | 20% | 10% | 18% | −18.3 | <.0001 |

TABLE 9-continued

Percentage of hypoglycemia/SH preceded by a low BG:

| BG | <24 h. | 24-48 h. | 48-72 h. | >72 h. | Runs Test Z | p-level |
|---|---|---|---|---|---|---|
| 1.9-2.8 mmol/l | 55% | 20% | 7% | 18% | −14.7 | <.0001 |
| SH | 64% | 11% | 6% | 19% | −11.1 | <.0001 |

We conclude that more than half of all hypoglycemic SMBG readings and approximately ⅔rds of all SH episodes, are preceded by at least one hypoglycemic reading within the previous 24 hours. In addition, hypoglycemic events tend to appear in clusters. Thus, an initial hypoglycemic episode may be a warning sign for upcoming recurrent hypoglycemia.

II. Example No. 2

This method uses routine self-monitoring blood glucose (SMBG) data and pertains directly to enhancement of home SMBG devices by introducing intelligent data interpretation logic, capable of predicting both $HbA_{1c}$ and periods of increased risk for significant hypoglycemia. The method has two components: (1) Algorithm 1 estimating $HbA_{1c}$, and (2) Algorithms 2 & 3 predicting long-term and short-term (within 24 hours) significant hypoglycemia, respectively. In this report we describe the steps of development, optimization and validation of the $HbA_{1c}$ estimation Algorithm 1, as well as its accuracy in estimating laboratory acquired $HbA_{1c}$.

Objective:

The primary goal was to reach an accuracy of 95% of measurements within ±1 $HbA_{1c}$ unit of a laboratory reference, which is the National Glycohemoglobin Standardization Program (NGSP) Criterion for accuracy for $HbA_{1c}$ assays.

Methods:

Subjects: SMBG data was captured for 100 subjects with Type 1 and 100 subjects with Type 2 diabetes mellitus (T1DM, T2DM) for 6 months and 4 months respectively, with $HbA_{1c}$ tests taken at months 0, 3 and 6 in T1DM and months 0, 2 and 4 in T2DM.

Development and Optimization of Algorithm 1: The Training Data Set consisted of SMBG and $HbA_{1c}$ data collected up to month 3 for T1DM and up to month 2 for T2DM. These Training Data were used for optimization of Algorithm 1 and for evaluation of a number of sample selection criteria that would ensure better accuracy. The sample selection criteria are requirements for any SMBG sample collected by the meter, which, if met, ensure accurate estimation of $HbA_{1c}$ from that sample. Consequently, the meter will scan every SMBG sample and if the sample selection criteria are met, will compute and display $HbA_{1c}$ estimate. After analyzing various cut points the following criteria were selected:

1. Test Frequency: In order to generate an estimate of $HbA_{1c}$, the meter will require an average of 2.5 tests or more per day over the last 60 days, e.g. a total of 150 SMBG readings over the past two months. It is important to note that this is an average per day, testing every day is not required.
2. Randomness of data: Certain 60-day samples with only post-prandial testing, or insufficient nighttime tests (<3% of sample) are to be excluded. In addition a safeguard against highly concentrated testing at one modal time of day was incorporated. These criteria are described in detail in the report.

Results: Prospective Validation and Accuracy of Algorithm 1:

The algorithm, including the sample selection criteria, was then applied to Test Data Set 1, which included SMBG and $HbA_{1c}$ data for two months prior to T1DM and T2DM subjects' last $HbA_{1c}$, and to an independent Test Data Set 2 consisting of 60 T1DM subjects who participated in a previous NIH study. The estimates obtained by Algorithm 1 were compared to reference $HbA_{1c}$ levels for validation purposes. In Test Data Set 1 the algorithm reached the NGSP criteria with an accuracy of 95.1% within +1 $Hba_{1c}$ unit of the lab reference. In Test Data Set 2 the algorithm reached the NGSP criteria as well with an accuracy of 95.5% within ±1 $Hba_{1c}$ unit of the lab reference. Investigation of the sample selection criteria showed that 72.5% of all subjects would generate such an accurate estimate every day, and 94% of all subjects would generate such an accurate an estimate about once every 5 days.

Conclusion: Routine SMBG data allow for accurate estimate of $HbA_{1c}$ that meets the NGSP criterion for accuracy of direct $HbA_{1c}$ assays.

Subjects & Inclusion Criterion

We have consented 100 subjects with Type 1 Diabetes (T1DM) and 100 subjects with Type 2 Diabetes (T2DM). One hundred seventy-nine subjects, 90 with T1DM and 89 with T2DM, completed significant portions of the SMBG data collection. The data of these 179 subjects were used for testing Algorithms 2 and 3. However, the testing of Algorithm 1 required that the subjects had not only SMBG data, but $HbA_{1c}$ data and SMBG records taken in the 60 days prior to SMBG. At month 3 of this study (month 2 for T2DM), 153 subjects (78 with T1DM) had completed $HbA_{1c}$ data and SMBG data meeting the above criterion. In addition, we used for testing of Algorithm 1 data for N=60 subjects with T1DM who participated in our previous NIH study (NIH). The demographic characteristics of all subjects are presented in Table 10.

TABLE 10

Demographic characteristics of the subjects.

| Variable | T1DM | T2DM | NIH |
|---|---|---|---|
| Age (years) | 41.5 (11.6) | 50.9 (8.1) | 44.3 (10.0) |
| Gender: % Male | 41% | 43% | 46% |
| Duration of diabetes (years) | 20.1 (10.1) | 11.7 (8.2) | 26.4 (10.7) |
| Body mass index | 25.4 (4.7) | 34.2 (8.1) | 24.3 (3.4) |
| Baseline $HbA_{1c}$ | 7.5 (1.1) | 8.5 (2.1) | 7.6 (1.0) |
| Second $HbA_{1c}$ | 7.3 (1.2) | 7.9 (1.6) | 7.4 (0.8) |
| Third $HbA_{1c}$ | 7.0 (0.9) | 7.5 (1.1) | — |
| # SMBG readings/subject/day | 5.4 (2.3) | 3.5 (0.8) | 4.1 (1.9) |
| # Days with SMBG readings in the 2 months preceding second $HbA_{1c}$ | 56.9 (5.4) | 57.3 (4.3) | 37.5 (14.3) |

Observed Meter Errors

Our investigation showed that the major reason for incomplete data within 60 days prior to $HbA_{1c}$ assays, or elsewhere, was not subject noncompliance, but meter failure. The time and date of the ONE TOUCH ULTRA meter could "jump" to a random date/time (e.g. November 2017), apparently if the patient depressed the "M" button for too long. We were checking the date/time of each meter upon return and we found that such event occurred in 60 meters throughout the course of the study. The time/date shift affected 15,280 readings, or approximately 10% of all readings. We stored these readings separately and had a student review them. In many, but not in all cases he was able to restore the date/time sequence of the readings. This error, together with a few meters lost in the mail, reduced the number of subjects with good data for Algorithm 1 analyses from 179 to 141. The data of 12 subjects were restored, which brought the final count to 153 subjects, 78 with T1DM and 75 with T2DM, who had uninterrupted time sequence of data prior to $HbA_{1c}$, suitable for testing of Algorithm 1.

Procedure

All subjects signed IRB-approved consent forms and attended orientation meetings where they were introduced to the ONE TOUCH ULTRA meter and completed screening questionnaires. Immediately after the introductory meeting all subjects visited a UVA laboratory and had blood drawn for baseline $HbA_{1c}$. T1DM subjects were followed for 6 months with laboratory $HbA_{1c}$ assays at months 3 and 6; T2DM subjects were followed for 4 months with laboratory $HbA_{1c}$ assays at months 2 and 4. Self-monitoring (SMBG) data were regularly downloaded from the meters and stored in databases. Parallel recording of significant hypoglycemic and hyperglycemic episodes was done by an automated e-mail/telephone tracking system every two weeks.

Data Storage and Cleaning

The raw data from ONE TOUCH ULTRA were stored in InTouch databases separately for T1DM and T2DM subjects. These raw data were cleaned for subject and meter errors using custom developed software and, in some cases, manual data cleaning (see Meter Errors above). When correction was not possible, the data was discarded.

In order to ensure that the results of our optimization can be generalized to population level, the algorithms were first optimized using a training data set and then validated using test data sets.

The Training Data set included 60 days of SMBG data taken prior to T1DM subjects' 3-month $HbA_{1c}$ determination. This data set was used to optimize the formulas for Algorithm 1. The data of T2DM subjects collected prior to their 2-month $HbA_{1c}$ were used to identify Sample Selection Criteria, which were not apparent in T1DM data. However, T2DM subjects' data were not used for optimization of Algorithm 1 formulas. The file containing these data is PASS01.DAT.

Test Data Set 1 included 60 days of SMBG data taken prior to T1DM subjects' 6-month $HbA_{1c}$ determination, and T2DM subjects' 4-month $HbA_{1c}$. Below we will refer to these data as Data Set 1. The file containing these data is PASS02.DAT.

Test Data Set 2 contained data for N=60 subjects with T1DM from a previous NIH study. These data were collected using ONE TOUCH PROFILE meters. Below we will refer to these data as Data Set 2. The file containing these data is HAT0.XLS.

The Variables in PASS01.DAT, PASS02.DAT, and HAT0.XLS are as Follows:

ID, MONTH, DAY, HOUR, YEAR—self-explanatory ID number and time of reading.
PLASBG—BG as recorded by One Touch Ultra (N/A in HAT0.DAT because One Touch Profile was used).
RISKLO, RISKHI—control variables representing the result of data transformation (see below).
BG and BGMM—BG converted to whole blood BG, and then presented in mmol/l (see below).

The aggregated (per subject) data, $HbA_{1c}$, its estimate, and estimation errors are stored in Excel files PASS1.XLS and PASS2.XLS.

The Variables in PASS1.XLS. PASS2.XLS, and HAT1.XLS are as Follows:
ID, TYPE (of diabetes)
HBA1—reference baseline HbA1c value
HBA2—reference HbA1c at 3 months(2 months for T2DM)—this is to be predicted;
EST2 and ERR2—Estimate of HbA1c and its error;
Control variables (all variables used by Algorithm 1):
BGMM1—average BG in mmol/l (see Part 2 below);
RLO1, RHI1—lowland high BG indices (see Part 2 below);
L06—low BG index at night—computed on readings between midnight and 6:59 a.m. (i.e. if (0.le..HOUR.le.6));
NC1=number of SMBG readings in the past 60 days;
NDAYS=number of days with SMBG readings in the past 60 days.
N06-% of SMBG readings in time intervals 0-6:59; 7-12:59;
EXCLUDE=0,1—samples suggested for exclusion by the algorithm, if EXCLUDE=1.

The files PASS01.DAT and PASS1.XLS can be matched by subject's ID number. Similarly, files PASS02.DAT and PASS2.XLS and HAT0.XLS and HAT1.XLS can be matched by subject's ID number. The raw data and all second-generation data files were transmitted to LifeScan, Inc.

Development of Algorithm 1
Formula Derivation:

Most of the exploration and the development of Algorithm 1 occurred during Example No. 1 of this project. Example No. 1 did not include data collection. Instead, we used a data set collected in a clinical trial by Amylin Pharmaceuticals. Example No. 1 suggested three possible formulas for estimation of HbA1c from SMBG data: (1) A formula using average SMBG, Low and High BG Indices; (2) A formula using average SMBG and a previous reference HbA1c reading, and (3) A simple linear formula using average SMBG only (see Example No. 1).

Another objective criterion for accuracy of $HbA_{1c}$ estimation was set forward (in Example No. 1 we used least squares estimation, % error, and absolute error to evaluate the accuracy of each formula). This new requirement translated into a different optimization criterion for Algorithm 1, e.g. the formulas were no longer optimized to produce minimal sum of squares of the errors (least squares estimation), but to fit the estimates within an uniform±1 band from reference $HbA_{1c}$.

In order to do so we analyzed the errors of our first linear model (formula Example No. 1) with respect to this uniform fit, using the Training Data for T1DM subjects only. We found that these errors were positively correlated (r=0.3) with subjects' High BG Index and used this relationship to correct our first linear model. We found that it was best using the High BG Index as a categorical variable, splitting the subject sample into groups with increasing High BG Index, and introducing corrections to the linear model within each group. The idea was to introduce corrections using the Low BG Index within each particular group, not throughout the whole sample as it was suggested in Example No. 1. This change was dictated by the different scheme of optimization based on the NGSP criterion.

Thus, based on Training Data for T1DM subjects, we finalized the following Algorithm 1:

Part 1—Pre-Processing of the Data:
BG=PLASBG/1.12 (converts plasma to whole blood BG, which is used throughout).
BGMM=BG/18 (converts BG to mmol/l).
The following lines compute Low and High BG Index for each SMBG reading:
COM SCALE=(ln(BG))**1.08405-5.381.
COM RISK1=22.765*SCALE*SCALE.
COM RISKLO=0.
IF (BG le 112.5) RISKLO=RISK1.
COM RISKHI=0.
IF (BG gt 112.5) RISKHI=RISK1.
The following lines aggregate the data per subject:
BGMM1=average (BGMM) per subject;
RLO1=average (RISKLO) per subject;
RHI1=average (RISKHI) per subject;
L06=average (RISKLO) computed only for readings during the night, missing if there are no readings at night.
N06, N12, N24-% of SMBG readings in time intervals 0-6:59; 7-12:59, and 18-23:59, e.g. if (0.le.HOUR.le.6)), if (7.le.HOUR.le.12)), and if (18.le.HOUR.le.24)), respectively.
NC1=total number of SMBG readings in the past 60 days;
NDAYS=number of days with SMBG readings in the past 60 days.

Part 2—Estimation Procedure:
This estimation procedure is based on the linear model from our Example No. 1:

$$HbA_{1c}=0.41046*BGMM+4.0775.$$

Analyzing the errors of this formula we found that the errors depend on the High BG Index. Thus, we classified all subjects on the base of their High BG Index, and then introduced corrections to the linear model within each category as follows:

A. Each subject is assigned a group depending on his/her High BG Index:
  if (RHI1 le 5.25 or RHI1 ge 16) GRP=0.
  if (RHI1 gt 5.25 and RHI1 lt 7.0) GRP=1.
  if (RHI1 ge 7.0 and RHI1 lt 8.5) GRP=2.
  if (RHI1 ge 8.5 and RHI1 lt 16) GRP=3.
B. For each group we have the following estimates:
  E0=0.55555*BGMM1+2.95.
  E1=0.50567*BGMM1+0.074*L06+2.69.
  E2=0.55555*BGMM1−0.074*L06+2.96.
  E3=0.44000*BGMM1+0.035*L06+3.65.
  EST2=E0.
  if (GRP eq 1) EST2=E1.
  if (GRP eq 2) EST2=E2.
  if (GRP eq 3) EST2=E3.
C. Corrections for some rarely occurring outliers:
  if (missing(L06)) EST2=E0.
  if (RLO1 le 0.5 and RHI1 le 2.0) EST2=E0−0.25.
  if (RLO1 le 2.5 and RHI1 gt 26) EST2=E0−1.5*RLO1.
  if ((RLO1/RHI1) le 0.25 and L06 gt 1.3) EST2=EST2−0.08.

Accuracy Criteria
In order to evaluate the accuracy of Algorithm 1 we use several standard criteria:
  1) NGSP Accuracy Criterion requires at least 95% of all estimates to be within ±1 $HbA_{1c}$ unit from reference $HbA_{1c}$.
  2) Average absolute deviation of Estimated from measured $HbA_{1c}$;
  3) Average percent deviation of Estimated from measured $HbA_{1c}$.

Important Note: The NGSP accuracy criterion is designed for testing of devices that measure $HbA_{1c}$ directly. Here we apply this criterion to estimates of $HbA_{1c}$ from SMBG data. However, the goal of such estimates is not to replace $HbA_{1c}$ laboratory measurement, it is to assist patients and physicians in the day-to-day management of diabetes. As opposed to laboratory measurement, the estimates utilize data that are available anyway and are available on a daily basis, without requiring special equipment or visit at the physician's office.

To illustrate how other direct measures of $HbA_{1c}$ agree with traditional laboratory measures, we tested blood sample from 21 IDDM patients and analyzed for $HbA_{1c}$ with both the DCA 2000 and the clinical laboratory. Out of these 21 tests there was one large error of 2.5 units $HbA_{1c}$. Table 11 presents the accuracy results of this FDA approved office device:

TABLE 11

Accuracy of DCA 2000 in T1DM:

| | DCA 2000 |
|---|---|
| NGSP criterion - % within ±1 $HbA_{1c}$ unit | 95.2% |
| Average absolute error (units $HbA_{1c}$) | 0.45 |
| Average percent error | 5.7% |

Sample Selection Criteria

Formula Derivation:
The estimation of HBA1c uses 60 consecutive days of SMBG. We will refer to such 60 consecutive days of SMBG as sample. Each person generates numerous samples in the course of his/her SMBG. In fact, each new measurement brings about a new sample, slightly different than the previous one. Thus, it is a natural assumption that the meter should have some control points for the quality of SMBG sample data from which $HbA_{1c}$ is to be estimated.

Therefore, after the general algorithm formula was optimized, it was then applied to the entire Training Data Set (data for T1DM and T2DM subjects) in order to investigate conditions under which a SMBG sample would result in an inaccurate estimation of $HbA_{1c}$.

This investigation concentrated on the following patterns occurring in SMBG that would result in inaccurate estimation:

1) Infrequent SMBG—certain number of reading is needed over two months in order to estimate HbA1c. If this number is not achieved, the estimation maybe inaccurate;

2) Patterns of SMBG skewed towards hyperglycemia occurring when subjects test predominantly after meals, or use oral medications with a primary concern of high BG;

3) Skewed temporal patterns of SMBG, e.g. testing predominantly at a few fixed times each day, which does not yield a good daily profile of a subject's BG fluctuations.

After investigating such patterns, we selected optimal sample selection criteria based on the most accurate and least exclusionary cut points. For a detailed description of the programming logic and statements for coding purposes please refer to Appendix A.

Final Sample Selection Criteria:

Criterion 1. Test Frequency: The algorithm will require that a 60-day sample contain an average of at least 2.5 tests per day, e.g. at least 150 SMBG readings over the last 60 days to generate an HbA1c estimate (NC1>=150).

Criterion 2. Randomness of Data:

2a) Oral Therapy/Postprandial Testing: (RLO1/RHI1>=0.005). In some SMBG samples the distribution of SMBG appeared to be very skewed towards hyperglycemia. This happened predominantly in T2DM subjects, who appeared to measure only at high BG. We have hypothesized that these samples contained no testing at low glucose ranges. Our investigation showed that about $1/3^{rd}$ of such samples would result in an overestimate of $HbA_{1c}$ ($2/3^{rds}$ would still result in accurate estimates). Based on that we recommend the meter to display no results, if a skewed sample is encountered, which in terms of computation is, formulated as LBGI to be at least ½% of the HBGI.

2b) Testing during the night: ($NO_6$>=3%). This criterion ensures that at least some of nighttime glycemia is accounted for. This criterion requires that 3% of all the readings occur at night (between midnight and 7:00 am). In other words, a sample will be acceptable if at least 5 out of 150 readings, taken over 2 months, are during the night. Note that patients are often advised to test at night, so this criterion promotes good management.

2c) Safeguard against highly abnormal testing patterns: A sample will not result in an estimate if more than ¾ of its readings occur in any one daily 6-hour interval. For example, if 80% of all tests in a sample occur right after breakfast, an estimate will not be produced. This criterion was requested by LifeScan, Inc. as a safeguard against people trying to "beat the algorithm", and it would allow us to thereby defend the validity, especially with clinicians.

Accuracy in the Training Data Set with Sequentially Employed Sample Selection:

The following tables describe the impact of the selected sample selection criteria on the accuracy and number of exclusions in the Training Data Set. Note that the accuracy of the final version of Algorithm 1 developed as a part of this study (Final Algorithm), and the accuracy of the simplest linear function that has been developed in Example No. 1 and included in the Example No. 1, (see First Linear Model).

For each model we present its accuracy without any sample selection criteria and with sequentially applied sample selection Criterion 1—Test Frequency, # readings NR≧150, and Criterion 2—Randomness of Data, as described above.

As seen in all tables, the accuracy of Algorithm 1 improves with sequentially applied sample selection criteria and reaches the NGSP required 95% after applying all criteria. These latter results are highlighted in the tables.

TABLE 12A

Final Sample Selection Criteria in Training Data Set - all subjects:

| | Final Algorithm | | | First Linear Model | | |
|---|---|---|---|---|---|---|
| | No sample exclusion | Criterion 1 | Criteria 1 and 2 | No sample exclusion | Criterion 1 | Criteria 1 and 2 |
| NGSP criterion - % within ±1 $HbA_{1c}$ unit | 93% | 93% | 95.5% | 83% | 83% | 90% |
| Average absolute error (units $HbA_{1c}$) | 0.54 | 0.53 | 0.47 | 0.61 | 0.59 | 0.52 |
| Average percent error | 7.2% | 7.2% | 6.8% | 8.2% | 8.2% | 7.6% |
| # of subjects with absolute error >1 | 11 | 9 | 5 | 26 | 22 | 11 |

TABLE 12B

Final Sample Selection Criteria in Training Data Set - T1DM: The coefficients of Algorithm 1 were optimized in this sample, which explains the high accuracy even without sample selection.

| | Final Algorithm | | | | First Linear Model | |
|---|---|---|---|---|---|---|
| | No sample exclusion | Criterion 1 | Criteria 1 and 2 | No sample exclusion | Criterion 1 | Criteria 1 and 2 |
| NGSP criterion - % within ±1 $HbA_{1c}$ unit | 96% | 96% | 96% | 86% | 88% | 90% |
| Average absolute error (units $HbA_{1c}$) | 0.45 | 0.46 | 0.45 | 0.54 | 0.53 | 0.51 |
| Average percent error | 6.3% | 6.6% | 6.5% | 7.7% | 7.8% | 7.6% |

TABLE 12C

Final Sample Selection Criteria in Training Data Set - T2DM: The Sample Selection Criterion 2 (Randomness of data) was developed primarily using this sample, which explains the 5% increase in accuracy when this criterion is applied.

|  | Final Algorithm | | | First Linear Model | | |
|---|---|---|---|---|---|---|
|  | No sample exclusion | Criterion 1 | Criteria 1 and 2 | No sample exclusion | Criterion 1 | Criteria 1 and 2 |
| NGSP criterion - % within ±1 $HbA_{1c}$ unit | 89% | 90% | 95% | 80% | 79% | 91% |
| Average absolute error (units $HbA_{1c}$) | 0.63 | 0.62 | 0.52 | 0.68 | 0.66 | 0.53 |
| Average percent error | 8.2% | 8.0% | 7.3% | 8.7% | 8.5% | 7.5% |

Frequency of Sample Exclusion in the Training Data:

The meter has a chance of estimating $HbA_{1c}$ at every new reading. If a sample does not meet the selection criteria, then the meter would not display a $HbA_{1c}$ estimate and would:
 (a) Wait until an appropriate sample is accumulated, or
 (b) If an appropriate sample is not accumulated, e.g. is a person has a permanently skewed measurement pattern, the meter could issue a prompt for SMBG pattern correction.

Our investigation shows that the majority of subjects (>95%) would get at least 10 $HbA_{1c}$ estimates over 60 days (as long as they measure frequently enough), and only 2% of the subjects would get no estimate due to skewed measurement patterns. These 2% of subjects would need to be prompted to correct their measurement pattern. Complete results of this investigation are given below:

We computed how many days (out of 60) a meter would not be able to show $HbA_{1c}$ results to a person due to samples that do not meet the selection criteria:
 1) For 72.5% of all subjects the meter will be able to report $HbA_{1c}$ every day;
 2) For additional 7.5% of all subjects the meter will be able to report $HbA_{1c}$ on 45 to 59 days (out of 60);
 3) For additional 10% of all subjects the meter will be able to report $HbA_{1c}$ on 12 to 44 days;
 4) For 9 subjects (5.9%) the meter would not be able to report $HbA_{1c}$ unless they change SMBG pattern.

Important Note: Most of these subjects would not get an estimate because they did not meet the Test Frequency Criterion 1, e.g. their samples always had less than 150 readings. Therefore, at least 94% of all subject will get at least one $HbA_{1c}$ estimate about every 5 days without changing their measurement pattern (this includes T1DM and T2DM).

If we require at least 150 readings for 60 days, only 3 subjects would not get $HbA_{1c}$ estimate:
 1) 95.6% will get at least 10 $HbA_{1c}$ estimates over 60 days;
 2) 2.2% will not get any estimates.

Thus, approximately 98% of the subjects who measure on average 2.5 times a day will get $HbA_{1c}$ estimate over 60 days, >95% will get estimate at least once a week. We conclude that the Sample Selection Criterion 2—Randomness of Data has, over time, a minimal impact on the display of $HbA_{1c}$ estimates. Only about 2% of the subjects would need to be prompted to improve their SMBG pattern.

It should be noted that the sample selection criteria are applicable to improve the accuracy of any formula estimating $HbA_{1c}$. The selection criteria are independent from any particular algorithm/formula and are applied before the estimation begins. For example, when applied, the sample selection criteria improve the accuracy of the latest Algorithm 1 developed as part of this study, and the accuracy of our first linear model presented in Example No. 1.

In addition, examining the effect of some other sample selection criteria reveals ways we can improve the accuracy further, should that be desirable. For example, when one of the original test frequency criteria was applied to the data, it demonstrated some incremental utility. This criterion is described further in Appendix E.

Prospective Validation of Algorithm 1:

Accuracy in Test Data Set 1:

The algorithm, including the final sample selection criteria, was then applied to Test Data Set 1 (SMBG for two months prior to last $HbA_{1c}$ for T1DM 1 and T2DM subjects) to generate $HbA_{1c}$ estimates. These estimates were then compared to reference $HbA_{1c}$ in order to prospectively validate Algorithm 1. Table 13 presents a summary of the results of this validation. A more detailed account of the impact of each of the sample selection criteria on the accuracy of the algorithm and can be found in Appendix C.

TABLE 13

Accuracy of Algorithm 1 Applied Prospectively:

| | Final Algorithm with Criteria 1 and 2 | | |
|---|---|---|---|
| | All Subjects | T1DM | T2DM |
| NGSP criterion - % within ±1 $HbA_{1c}$ unit | 95.1% | 97% | 93% |
| Average absolute error (units $HbA_{1c}$) | 0.45 | 0.38 | 0.54 |
| Average percent error | 6.2% | 5.4% | 7.4% |

Accuracy in Test Data Set 2:

Another independent NIH data set (N=60 subjects with T1DM) was used to validate the results with similar accuracy of 95.5% within 1 $HbA_{1c}$ percent units of the lab reference (Table 14):

TABLE 14

Accuracy of Algorithm 1 in Independent NIH Data Set:

| | All Subjects (T1DM) |
|---|---|
| NGSP criterion - % within ±1 $HbA_{1c}$ unit | 95.5% |
| Average absolute error (units $HbA_{1c}$) | 0.42 |
| Average percent error | 5.9% |

Comparison of Accuracy of Algorithm 1 to FDA-Approved Office Device:

As shown in Table 15 below, the accuracy of Algorithm 1 is comparable to the accuracy of $HbA_{1c}$ assays used in physicians' offices. As described in the Accuracy Criteria section, the DCA 2000 data was taken to illustrate how other direct measures of $HbA_{1c}$ agree with laboratory measures. We analyzed for $HbA_{1c}$ blood samples from 21 T1DM patients with both the DCA 2000 and the clinical laboratory. Out of these 21 tests there was one large error of 2.5 units $HbA_{1c}$:

TABLE 15

Accuracy of DCA 2000 in T1DM compared to Algorithm 1:

| | DCA 2000 | TEST DATA SET 1 | TEST DATA SET 2 |
|---|---|---|---|
| NGSP criterion - % within ± 1 $HbA_{1c}$ unit | 95.2% | 95.1% | 95.5% |
| Average absolute error (units $HbA_{1c}$) | 0.45 | 0.45 | 0.42 |
| Average percent error | 5.7% | 6.2% | 5.9% |

Frequency of Sample Exclusion in the Test Data:

As we discussed as part of the development of Algorithm 1, the meter has a chance of estimating $HbA_{1c}$ at every new reading. If a sample does not meet the selection criteria, then the meter would not display a $HbA_{1c}$.

We used Test Data Sets 1 and 2 to prospectively estimate the frequency of sample exclusion. In order to do so, we computed on how many days (out of 60) a meter would be able to show $HbA_{1c}$ results to a person, e.g. on how many days a person would have samples meeting the sample selection criteria. Tables 16A and 16B present summaries of these results for Test Data Sets 1 and 2. We include data for all subjects, and separately for subjects who measured on average 1.5 times/day (90 SMBG readings over 60 days) and 2.5 times/day (150 SMBG readings over 60 days):

TABLE 16A

Frequency of Sample Exclusion in Test Data Set 1:

| | All subjects (N = 148) | Subjects who measured on average >1.5 times/day (N = 146) | Subjects who measured on average >2.5 times/day (N = 130) |
|---|---|---|---|
| Percent of subjects to whom the meter will be able to report $HbA_{1c}$ every day; | 69.6% | 72.6% | 77.7% |
| Percent of subjects to whom the meter will be able to report $HbA_{1c}$ once every 3 days; | 87.8% | 91.1% | 93.1% |
| Percent of subjects to whom the meter will be able to report $HbA_{1c}$ once a week. | 91.9% | 95.5% | 96.9% |

TABLE 16B

Frequency of Sample Exclusion in Test Data Set 2:

| | All subjects (N = 60) | Subjects who measured on average >1.5 times/day (N = 55) | Subjects who measured on average >2.5 times/day (N = 30) |
|---|---|---|---|
| Percent of subjects to whom the meter will be able to report $HbA_{1c}$ every day. | 51.7% | 83.6% | 80.0% |
| Percent of subjects to whom the meter will be able to report $HbA_{1c}$ once every 3 days; | 95.0% | 100.0% | 100.0% |
| Percent of subjects to whom the meter will be able to report $HbA_{1c}$ once a week. | 96.7% | 100.0% | 100.0% |

Conclusion:

Tables 13-16 demonstrate that the meter would be able to produce an accurate estimate of $HbA_{1c}$, meeting the 95% NGSP accuracy criterion, on average once a week, for >96% of those who measure on average 2.5 times a day.

Appendix A—Software Logic for Sample Selection Criteria

Sample Selection Criteria—some SMBG samples are suggested for exclusion by the algorithm, or a message is issued to the subjects to correct their SMBG pattern. The sample selection criteria are programmed as follows:

Criterion 1. Test Frequency: The algorithm will require that a 60-day sample contain an average of at least 2.5 tests per day, e.g. at least 150 SMBG readings over the last 60 days to generate an, $HbA_{1c}$ estimate:
EXCLUDE=0.
if (NC1>=150) EXCLUDE=1.

Criterion 2. Randomness of Data:

2a) Oral Therapy/Postprandial Testing: In some SMBG samples the distribution of SMBG appeared to be very skewed towards hyperglycemia. This happened predominantly in T2DM subjects, who appeared to measure only at high BG. We have hypothesized that these samples contained no testing at low glucose ranges. Our investigation showed that about $1/3^{rd}$ of such samples would result in an overestimate of $HbA_{1c}$ ($2/3^{rds}$ would still result in accurate estimates). Based on that we recommend the meter to display no results, if a skewed sample is encountered, which in terms of computation is formulated as LBGI to be at least ½% of the HBGI.
if (RLO1/RHI1 lt 0.005) EXCLUDE=1.

2b) Testing during the night: (NO6>=3%). This criterion ensures that at least some of nighttime glycemia is accounted for. This criterion requires that 3% of all the readings occur at night (between midnight and 7:00 am). In other words a sample will be acceptable if at least 5 out of 150 readings, taken over 2 months, are during the night. Note that patients are often advised to test at night, so this criterion promotes good management.
if (N06 le 3.0) EXCLUDE=1.

2c) Safeguard against highly abnormal testing patterns: A sample will not result in an estimate if more than ¾ of its readings occur in any one daily 6-hour interval. For example, if 80% of all tests in a sample occur right after breakfast, an estimate will not be produced. This criterion was requested by LifeScan, Inc. as a safeguard against people trying to "beat the algorithm", and it would allow us to thereby defend the validity, especially with clinicians. In our data there are no samples that are so highly abnormal to trigger this criterion (See the Appendix B—Criterion 2c for detailed information). In terms of software implementation, the following frequencies will need to be computed from SMBG data:

M12-% SMBG readings from 6:00 am to noon (Breakfast)
M18-% SMBG readings from Noon to 6:00 pm (Lunch)
M24-% SMBG readings from 6:00 pm to 12:00 (Dinner)
M06-% SMBG readings from 12:00 to 6:00 am (Nighttime)
M15-% SMBG readings from 9:00 am to 3:00 pm
M21-% SMBG readings from 3:00 pm to 9:00 pm
M03-% SMBG readings from 9:00 pm to 3:00 am
M09-% SMBG readings from 3:00 am to 9:00 am
Then for any combination of (i,j) listed above:
if (Mij gt 75.0) EXCLUDE=1.

Appendix B—Sample Selection Criterion 2C

The criterion was suggested by LifeScan, Inc. as a Safeguard against highly abnormal testing patterns. The intent of this criterion is to prevent people from being able to "beat" the algorithm.

Basically, the criteria stipulate that You will not get an estimate if more than ¾ of your readings (or other desired number) occur in any one daily 6 hour interval or other desired interval).

So, for example, if more than ¾ of the tests occur after dinner, they will not get an estimate. This will give us more support to a general claim that people who do not test randomly will not be included in the calculation. I understand that the specific calculation and coding for this may seem complex, but the key here is that we may have to only put "You must test randomly throughout the day" or something similar as a broad claim to cover all of our exclusion criteria (except the test frequency). If we are required to, we can simply put a more exact definition in fine print such as "No daily 6 hour interval can have more than 75% of all the readings." This safeguard, along with our other criteria, may improve the clinical acceptance of the algorithm.

More Detail:
The 4 six hour intervals defined as follows:
6:00 am to noon (Breakfast)
Noon to 6:00 pm (Lunch)
6:00 pm to 12:00 (Dinner)
12:00 to 6:00 am (Nighttime)

This criteria could be run twice with different time intervals in order to prevent is people from concentrating testing around the cutpoints for the following six hour intervals, and thereby inappropriately still meeting this first criteria. For example if they had 40% at 11:50 pm and 40% at 12:10 pm, they would still have clustered testing but get by on the first pass of intervals, but not on the second pass of intervals.

Second Set of Intervals:
9:00 am to 3:00 pm
3:00 pm to 9:00 pm
9:00 pm to 3:00 am
3:00 am to 9:00 pm Note that alternatively, from a coding standpoint, one could apply the following instead for the same result:

No 18-hour period would have less than 25% of the readings.

You would have to run this against every 18-hour period staged by 3 hours:
9:00 am to 3:00 am
12:00 noon to 6:00 am
3:00 am to 9:00 am
6:00 pm to 12:00 noon
9:00 pm to 3:00 pm
12:00 midnight to 6:00 pm
3:00 am to 9:00 pm
6:00 am to 12:00 midnight Appendix C—Incremental Effect of Sample Selection Criteria on Accuracy of Algorithm 1 in Test Data Set 1

As described in the development of the algorithm, the following tables refer to Algorithm 1 developed as a part of this study (Final Algorithm), and the accuracy of the simplest linear function that has been developed in Example No. 1 and included in the Example No. 1, (see First Linear Model). The tables present the accuracy of Algorithm 1 in Test Data Set 1 without sample exclusion and with sequential application of the two sample selection criteria:

TABLE 17A

Accuracy of Algorithm - all subjects:

| | Final Algorithm | | | First Linear Model | | |
|---|---|---|---|---|---|---|
| | No sample exclusion | Criterion 1 | Criteria 1 and 2 | No sample exclusion | Criterion 1 | Criteria 1 and 2 |
| NGSP criterion - % within ±1 $HbA_{1c}$ unit | 86% | 91% | 95.1% | 83% | 85% | 89% |
| Average absolute error (units $HbA_{1c}$) | 0.56 | 0.48 | 0.45 | 0.59 | 0.54 | 0.49 |
| Average percent error | 7.4% | 6.7% | 6.2% | 7.8% | 7.5% | 7.0% |
| # of subjects with absolute error >1 | 21 | 10 | 5 | 25 | 16 | 11 |

Criterion 1 - Test Frequency, # readings NR >150, and

Criterion 2 - Randomness of Data, as described under Sample Selection Criteria:

TABLE 17B

Accuracy of Algorithm 1 in T1DM:

|  | Final Algorithm | | | First Linear Model | | |
|---|---|---|---|---|---|---|
|  | No sample exclusion | Criterion 1 | Criteria 1 and 2 | No sample exclusion | Criterion 1 | Criteria 1 and 2 |
| NGSP criterion - % within ±1 $HbA_{1c}$ unit | 90% | 95% | 97% | 90% | 93% | 95% |
| Average absolute error (units $HbA_{1c}$) | 0.45 | 0.40 | 0.38 | 0.49 | 0.45 | 0.43 |
| Average percent error | 6.1% | 5.6% | 5.4% | 6.9% | 6.7% | 6.4% |

TABLE 17C

Accuracy of Algorithm 1 in T2DM:

|  | Final Algorithm | | | First Linear Model | | |
|---|---|---|---|---|---|---|
|  | No sample exclusion | Criterion 1 | Criteria 1 and 2 | No sample exclusion | Criterion 1 | Criteria 1 and 2 |
| NGSP criterion - % within ±1 $HbA_{1c}$ unit | 81% | 86% | 93% | 76% | 76% | 81% |
| Average absolute error (units $HbA_{1c}$) | 0.68 | 0.59 | 0.54 | 0.69 | 0.64 | 0.57 |
| Average percent error | 8.6% | 8.0% | 7.4% | 8.7% | 8.6% | 7.8% |

Appendix D—Alternative Testing Frequency Criterion

A superior Testing Frequency criterion may contribute more significantly to the accuracy of Algorithm 1. This is because reasons for employing the Testing Frequency Criterion 1 were based not solely on data analysis, but on other considerations. If Criterion 1 requiring 150 readings in 2 months is found too restrictive, an alternative solution maybe used. This is the original Testing Frequency criterion, which required 35 days (out of 60) with SMBG readings with an average frequency of 1.8 readings/day, e.g. a total of 63 readings taken over 35 out of 60 days. Table 18 demonstrates that with this original relaxed testing frequency criterion, plus Criterion 2 (randomness of data), the accuracy of Algorithm 1 exceeds 95%:

Important Note: In addition, this alternative criterion screens out samples, which have big chunk of missing data, e.g. if SMBG was discontinued for 4 weeks and then the person comes back, $HbA_{1c}$ estimate should not be displayed. A clear example of such a pattern occurred in Test Data Set 2—the subject who had the largest error in his/her $HbA_{1c}$ estimate had collected 159 readings over only 30 out of 60 days. Thus, it is possible for a subject to meet the requirement of 150 readings with readings collected quickly over a few days, which may result in inaccurate HbA1c estimation.

TABLE 1

Accuracy of Algorithm 1 using alternative Testing Frequency Criterion (35 of readings/1.8 readings/day) and the Randomness of Data Criterion:

|  | Training Data Set | | | Test Data Set 1 | | | Test Data Set 2 |
|---|---|---|---|---|---|---|---|
|  | All Ss | T1DM | T2DM | All Ss | T1DM | T2DM |  |
| NGSP criterion - % within ±1 $HbA_{1c}$ unit | 95% | 96% | 94% | 95% | 97% | 92% | 100% |
| Average absolute error (units $HbA_{1c}$) | 0.48 | 0.44 | 0.55 | 0.46 | 0.39 | 0.55 | 0.40 |
| Average percent error | 6.8% | 6.3% | 7.6% | 6.3% | 5.5% | 7.2% | 5.5% |

Exemplary Definitions for Example No. 2 (But not Limited Thereto)
1) Severe hypoglycemia (SM) is identified as low blood glucose (BG) resulting in stupor, seizure, or unconsciousness that precludes self-treatment;
2) Moderate hypoglycemia (MH) is identified as severe neuroglycopenia disrupting subject's activity, but not precluding self-treatment;
3) Biochemical severe hypoglycemia (BSH) is defined as plasma BG reading <=39 mg/dl;
4) Biochemical moderate hypoglycemia (BMH) is defines as plasma BG reading between 39 and 55 mg/dl.
5) All of the above will be referred to as significant hypoglycemia.

ADDITIONAL OBJECTIVES

The data from this Example were used to validate prospectively the following algorithms:
Algorithm 2—a classification algorithm using 30-45 days of SMBG data for a subject, to classify this subject in a certain risk category for future significant hypoglycemia. The classification is temporary, e.g. when a subjects' SMBG pattern changes, the classification changes as well;
Algorithm 3—a data tracking/decision-making algorithm that uses a sequence of SMBG data to make a decision whether to raise a flag for upcoming (within 24 hours) significant hypoglycemia. We now describe in detail Algorithms 1&2 and the results of their testing Subjects We have consented 100 subjects with Type 1 Diabetes (T1DM) and 100 subjects with Type 2 Diabetes (T2DM). One hundred seventy-nine subjects, 90 with T1DM and 89 with T2DM, completed significant portions of the SMBG data collection.

Procedure

All subjects signed an IRB—approved consent forms and attended orientation meetings where they were introduced to the ONE TOUCH ULTRA meter and completed screening questionnaires. Immediately after the introductory meeting all subjects visited a UVA laboratory and had blood drawn for baseline $HbA_{1c}$. T1DM subjects were followed for 6 months with laboratory $HbA_{1c}$ assays at months 3 and 6; T2DM subjects were followed for 4 months with laboratory $HbA_{1c}$ assays at months 2 and 4. Self-monitoring (SMBG) data were regularly downloaded from the meters and stored in databases. Parallel recording of significant hypoglycemic and hyperglycemic episodes was done by a custom-designed automated e-mail/telephone tracking system contacting all participants in two-week intervals. Table 19 present summaries of the SMBG and Severe Hypoglycemia Moderate Hypoglycemia [SH/MH] data collection.

TABLE 19

Data collection summary

| Variable | T1DM (N = 90 subjects) | T2DM (N = 89 subjects) |
|---|---|---|
| # SH episodes | 88 | 24 |
| # MH episodes | 1,660 | 190 |
| # SMBG readings | 92,737 | 35,306 |
| # BSH episodes | 1,039 | 39 |
| # BMH episodes | 5,179 | 283 |

No significant changes were made to the formulas of Algorithms 2 and 3. These formulas remain practically identical to the formulas presented in the report from Example No. 1 of March 2002. The only two changes include: (a) a correction of a typo in the list of risk categories for SH/MH (Example No. 1) and (b) change in one line of Algorithm 3 (Example No. 1). The reason for the latter is explained below.

Since Algorithms 1 and 2 remain unchanged, we can consider the entire Example No. 2 data collection as a prospective testing of these algorithms.

Formulas for Algorithm 2

Algorithm 2 proceeds as follows:
1) Based on one month of SMBG data, each subject is classified into one of 15 risk categories (RCAT) depending on his/her Low BG Index (LBGI) as follows:
if (LBGI le 0.25) RCAT=0.
if (LBGI gt 0.25 and LBGI le 0.50) RCAT=1.
if (LBGI gt 0.50 and LBGI le 0.75) RCAT=2.
if (LBGI gt 0.75 and LBGI le 1.00) RCAT=3.
if (LBGI gt 1.00 and LBGI le 1.25) RCAT=4.
if (LBGI gt 1.25 and LBGI le 1.50) RCAT=5.
if (LBGI gt 1.50 and LBGI le 1.75) RCAT=6.
if (LBGI gt 1.75 and LBGI le 2.00) RCAT=7.
if (LBGI gt 2.00 and LBGI le 2.50) RCAT=8.
if (LBGI gt 2.50 and LBGI le 3.00) RCAT=9.
if (LBGI gt 3.00 and LBGI le 3.50) RCAT=10.
if (LBGI gt 3.50 and LBGI le 4.25) RCAT=11.
if (LBGI gt 4.25 and LBGI le 5.00) RCAT=12.
if (LBGI gt 5.00 and LBGI le 6.50) RCAT=13.
if (LBGI gt 6.50) RCAT=14.
2) The theoretical probability for future significant hypoglycemia are computed through a two-parameter Weibull probability distribution, with a distribution function given by the formula: $F(x)=1-\exp(-a.x^b)$ for any x>0 and 0 otherwise. The parameters of this distribution depend on the desired duration of the prediction and are described in the report from Example No. 1. If implemented in a meter, this step would provide a continuous-type estimation of the risk for significant hypoglycemia, e.g. "50% within the next month."
3) Each subject is classified at minimal, low, moderate, or high risk for future significant hypoglycemia: These ranges are defined as follows: Minimal risk (LBGI≦1.25); Low risk (1.25<LBGI≦2.5); Moderate risk (2.5<LBGI≦5), and High risk (LBGI>5). If implemented in a meter, this step would provide a discrete-type estimation of the risk for significant hypoglycemia, e.g. "high risk within the next month."

Formulas for Algorithm 3

First, in order to avoid the computing of baseline risk values presented in the Example No. 1 Report description of Algorithm 3, we have modified one line in the code. Now Algorithm 3 uses the results from Algorithm 2 instead. This change was introduced for the presentation of sample results for two subjects on Oct. 28, 2002. At this time it appeared that it was more convenient to have a simple Excel spreadsheet to demonstrate the action of Algorithm 3, which was possible if the computation of baseline values was avoided. This step did not change the accuracy of Algorithm 3 and therefore was left as a permanent change facilitating the programming of Algorithm 3. No other changes were introduced to Algorithm 3 after Oct. 28, 2002. Here we present the formulas of Algorithm 3 as given in the report from Example No. 1, with the changed line marked.
1) Computing of a Low BG Risk value (RLO) for each BG reading that is done by the following code (here BG is measured in mg/dl, if the units are mmol/l the coefficients are different):

```
scale=(ln(bg))**1.08405 − 5.381
risk=22.765*scale*scale
if (bg__1 le 112.5) then
    RLO=risk
else
    RLO=0
endif
```

2) For each SMBG reading we compute a running value of the LBGI(n), and another statistics, SBGI(n) that is the standard deviation of the low BO risk values. These two parameters were computed with a certain lag (n) backwards from each SMBG reading, e.g. included that reading and (n−1) readings taken prior to that reading.

3) The computation of LBGI(n) and SBGI(n) used a provisional means procedure that is based on the following recursive code:

Initial values at n (or at the max(1,n−k) to be exact in order to account for meter readings with a sequential number less than k):

$LBGI(n)=rlo(n)$ $rlo2(n)=0$

Values for any consecutive iteration j between n and 1, counted backwards:

$LBGI(j)=((j-1)/j)*LBGI(j-1)+(1/j)*RLO(j)$ $rlo2(j)=((j-1)/j)*rlo2(j-1)+(1/j)*(RLO(j)-LBGI(j))**2$ After this cycle is completed we have the value of LBGI(n) and we compute $SBGI(n)=sqrt(rlo2(n))$ From this computation we save two sets of values: for n=150 and for n=50 (e.g. for the last 150 and the last 50 observations).

4) Decision-Making Rule: At each SMBG reading the procedure decides whether to raise a flag warning of upcoming SH. If the flag is raised, the procedure decides whether or not to lower the flag. These decisions depend on three threshold parameters, $\alpha$, $\beta$, $\gamma$ that work as follows:

For subject at low-to-moderate risk (LM group):
FLAG=0.
if (LBGI(150) ge 2.5 and LBGI(50) ge (1.5*LBGI(150) and SBGI(50) ge SBGI(150)) FLAG=1.
if (RLO ge (LBGI(150)+1.5*SBGI(150)) FLAG=1.

In other words, at each SMBG reading the flag could be raised if one of two conditions is met:

1) The subject to be at a moderate of high risk for SH based on Algorithm 2 classification from the last 150 trials and the LBGI and SD of LBGI to increase over the last 50 trials;

2) Or, to have a surge in the Low BG Index as determined by the second inequality.

The heuristic explanation of these statements was presented in the report from Example No. 1. As described above the first "if" statement has been changed from its original form to avoid the use of baseline LBGI and to utilize the output from Algorithm 2.

As described in the report from Example No. 1, once the flag is raised it remains raised for 24 hours. In order to evaluate the accuracy of Algorithm 3 we use the technique proposed before—we compute two measures:

1) The % predicted upcoming SH/MH episodes within 24 hours, and

2) The ratio $R_{ud}$ of duration periods of "flag up" to "flag down" (annoyance index).

While the % predicted episodes of SH needs to be high, the ratio $R_{ud}$ needs to be low. This is because by increasing the percentage of predicted SH episodes, we unavoidably increases the number of "raised flags," which in turn increases the number of potential "false alarms." Since a "false alarm" is not clearly defined (see report from Example No. 1), we will use $R_{ud}$ as an indicator of the utility of Algorithm 3.

Our previous best result presented in the report from Example No. 1 was a prediction of 50% of SH/MH episodes within 24 hours, and $R_{ud}$=1:10, e.g. one day of high-risk alert was alternating with 10 days of no alert. Here we will keep the same flag up/down ratio and will compute the % predicted within 24 hours SH and MH episodes separately for T1DM and T2DM subjects. For this prediction we will not use BSH and BMH episodes since these were recorded by the meter and therefore are a part of the prediction function.

Evaluation of Risk for Significant Hypoglycemia Within 1-3 Months: Accuracy of Algorithm 2

We have evaluated the predictive power of Algorithm 2 as follows:

1) First, we have computed the LBGI from one month of SMBG data and classified each subject at Minimal, Low, Moderate, and High risk for significant hypoglycemia as described above.

2) Then, during the following 1-3 months we counted for each subject the number of prospectively recorded SH, BSH, MH, and BMH episodes.

The FIGS. 16-19 below present the number of SH, BSH, MH, and BMH episodes per subject observed prospectively for 1 month, or 3 months, following a month of SMBG, separately for T1DM and T2DM. Statistical comparisons are included as well.

In addition, a direct linear regression using the LBGI, history of SH as reported in the screening questionnaires in terms of number of episodes in the past year, and baseline $HBA_{1c}$, predicted significantly ($R^2$=0.62, F=48, p<0.0001) the total number of upcoming in the next 3 months significant hypoglycemic episodes (SH+MH+BSH+BMH). The predictive variables, in order of their significance were: 1) LBGI (t=8.2, p<0.0001) accounting alone for 55% of the variance of future significant hypoglycemia (e.g. $R^2$=0.55); 2) History of SH (t=3.6, p=0.0005) accounting for additional 5% variance, and HbA1c (t=2.2, p=0.03) accounting for additional 2% variance. This confirms previous results that the LBGI is a most significant predictor of future hypoglycemia, while the contribution of $HbA_{1c}$ to that prediction is modest.

The theoretical probabilities for future significant hypoglycemia computed by the Weibull model had an excellent agreement with the prospectively observed significant hypoglycemic episodes—for both severe and moderate episodes the coefficients of determination were above 90%.

Prediction of Upcoming (within 24 Hours) Significant Hypoglycemia: Accuracy of Algorithm 3

The tables below present the accuracy of the short-term prediction (within 24 hours) of SH and MH episodes separately for T1DM and T2DM subjects. Each line of Tables 20 and 21 presents the percent predicted episodes, if a certain number of SMBG readings were available id the 24-hour period used for the prediction. For example, the first line in each table presents the % predicted episodes regardless of whether there were any SMBG readings in the 24 hours preceding an episode. It is seen that the accuracy of the prediction increases with the number of readings preceding an episode. Thus, if a person measures 3 or more times a day, the meter could warn about, and potentially help avoid more than half of significant hypoglycemic episodes.

Important Note: For the purposes of accuracy assessment of Algorithm 3 we use only SH and MH episodes recorded by the independent from SMBG e-mail/telephone system, which required each participant to report SH and MH by date and time every two weeks. As our interviews showed, sometimes the participants used for their reports the time and date of the last SMBG reading preceding an episode, instead of the actual time/date of that episode, because looking at the meter was helping their recollection. As a result, there were a number of episodes for which the time elapsed from the closest preceding SMBG reading to the time of the episode, was close to zero. In order to account for such suspicious time recording Column 3 in each table presents the accuracy of Algorithm 3 restricted only to episodes for which the lead warning time was at least 15 minutes. Given that the average lead warning time was 11 hours, we conclude that in most cases, the warning would come early enough to prompt adequate self-treatment.

In Tables 20 and 21 the Annoyance Index is set to $R_{ud}>=10$ to match the report from Example No. 1.

TABLE 20

Accuracy of Algorithm 3 in T1DM.

| $R_{ud}$ = 10.2 | | % Predicted SH + MH Episodes | % Predicted SH Episodes | % Predicted SH + MH Episodes with warning time >15 minutes |
|---|---|---|---|---|
| No restrictions | | 53% | 48% | 49% |
| Minimum | 3 | 55% | 58% | 52% |
| number of | 4 | 59% | 60% | 55% |
| SMBG readings in the 24 hours preceding the episode. | 5 | 63% | 60% | 59% |

TABLE 21

Accuracy of Algorithm 3 in T2DM.

| $R_{ud}$ = 10.0 | | % Predicted SH + MH Episodes | % Predicted SH Episodes | % Predicted SH + MH Episodes with warning time >15 minutes |
|---|---|---|---|---|
| No restrictions | | 52% | 38% | 48% |
| Minimum | 3 | 57% | 60% | 53% |
| number of | 4 | 64% | 64% | 59% |
| SMBG readings in the 24 hours preceding the episode. | 5 | 73% | 73% | 68% |

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced therein.

We claim:

1. A system for evaluating the $HbA_{1c}$ of a patient based on blood glucose (BG) data collected over a first predetermined duration, said system comprising:
   a database component operative to maintain a database identifying said BG data; and
   a processor programmed to:
      pre-process the collected BG data to convert the collected BG data into derived BG data derived from said collected BG data, estimate $HbA_{1c}$ by applying at least one predetermined formula to said derived BG data,
      validate the estimate via sample selection criteria; and
      output the estimate to a user.

2. The system of claim 1, wherein said first predetermined duration is about 60 days.

3. The system of claim 1, wherein said first predetermined duration ranges from about 45 days to about 75 days.

4. The system of claim 1, wherein said first predetermined duration ranges from about 45 days to about 90 days.

5. The system of claim 1, wherein the preprocessing of the data comprises:
   conversion of plasma to whole blood BG mg/dl;
   conversion of BG measured in mg/dl to units of mmol/l; and
   computing Low Blood Glucose Index (RLO1) and High Blood Glucose Index (RHI1).

6. The system of claim 1, wherein the preprocessing of the data comprises:
   conversion of plasma to whole blood BG mg/dl via BG=PLASBG (mg/dl) /1.12;
   conversion of BG measured in mg/dl to units of mmol/l via BGMM=BG/18; and
   computing Low Blood Glucose Index (RLO1) and High Blood Glucose Index (RHI1) using a predetermined mathematical formula defined as:
   Scale=$[\ln(BG)]^{1.0845}-5.381$, wherein BG is measured in units of mg/dl,
   Risk1=$22.765(Scale)^2$, wherein
   RiskLO=Risk1 if (BG is less than about 112.5) and therefore risk of LBGI exists, otherwise RiskLO=0, and
   RiskHI=Risk1 if (BG is greater than about 112.5) and therefore risk of HBGI exists, otherwise RiskHI=0,
   BGMM1=average of BGMM per patient,
   RLO1=average of RiskLO per patient,
   RHI1=average of RiskHI per patient,
   L06=average of RiskLO computed only for readings during the night, otherwise missing if there are no readings at night,
   N06, N12, N24 are percentage of SMBG readings in time intervals,
   NC1=total number of SMBG readings in the first predetermined duration; and
   NDAYS=number of days with SMBG readings in the first predetermined duration.

7. The system of claim 6, wherein the N06, N12, N24 are percentage of SMBG readings in time intervals of about 0-6:59 hour time period; about 7-12:59 hour time period, and about 18-23:59 hour time period, respectively.

8. The system of claim 6, comprising assigning a group depending on the patient's computed High BG Index using a predetermined mathematical formula defined as:
   if (RHI1 is ≦about 5.25 or if RHI1 is ≧about 16) then the assigned group=0,
   if (RHI1 is >about 5.25 and if RHI1 is <about 7.0) then the assigned group=1, if (RHI1 is ≧about 7.0 and if RHI1 is <about 8.5) then the assign group=2, and
if (RHI1 is ≧about 8.5 and if RHI1 is <about 16) then the assigned group=3.

9. The system of claim 8, comprising providing estimates using a predetermined mathematical formula defined as:
E0=0.55555*BGMM1+2.95,
E1=0.50567*BGMM1+0.074*L06+2.69,
E2=0.55555*BGMM1−0.074*L06+2.96,
E3=0.44000*BGMM1+0.035*L06+3.65; and
if (Group=1) then EST2=E1, or if (Group=2) then EST2=E2, or if (Group=3) then EST2=E3, otherwise EST2=E0.

10. The system of claim 9, comprising providing further correction of the estimates using a predetermined mathematical formula defined as:
if (missing(L06)) EST2=E0,
if (RLO1 is ≦about 0.5 and RHI1 is le about 2.0) then EST2=E0−0.25,
if (RLO1 is ≦about 2.5 and RHI1 is >about 26) then EST2=E0−1.5*RLO1, and
if ((RLO1/RHI1) is ≦about 0.25 and L06 is >about 1.3) then EST2=EST2-0.08.

11. The system of claim 10 for estimating the $HbA_{1c}$ of a patient based on BG data collected over the first predetermined duration, wherein said estimating $HbA_{1c}$ comprises:
  a) $HbA_{1c}$=the EST2 defined by claim 8 or as corrected by claim 10 or
  b) $HbA_{1c}$=0.809098*BGMM1+0.064540*RLO1−0.151673*RHI1+1.873325, wherein
    BGMM1 is the average BG (mmol/l) of claim 6,
    RLO1 is the Low BG Index of claim 6,
    RHI1 is the High BG Index of claim 6; or
  c) $HbA_{1c}$=0.682742*HBA0+0.054377*RHI1+1.553277, wherein HBA0 is a previous reference $HbA_{1c}$ reading taken about a second predetermined period prior to the estimate, wherein
    RHI1=is the High BG Index of claim 6; or
  d) $HbA_{1c}$=0.41046*BGMM+4.0775
    wherein BGMM1is the average BG (mmol/l) of claim 6.

12. The system of claim 11, wherein said second predetermined duration is about three months.

13. The system of claim 11, wherein said second predetermined duration ranges from about 2.5 months to about 3.5 months.

14. The system of claim 11, wherein said second predetermined duration ranges from about 2.5 months to six months.

15. The system of claim 11, wherein the validation of the $HbA_{1c}$ estimate using sample selection criteria of $HbA_{1c}$ estimate only if the first predetermined duration sample meets at least one of the following four criteria:
  a) a test frequency criterion wherein if the first predetermined duration sample contains an average of at least about 1.5 to about 2.5 tests per day;
  b) an alternative test frequency criterion only if the predetermined duration sample contains at least a third predetermined sample period with readings with an average frequency of about 1.8 readings/day;
  c) a randomness of data criterion-1 wherein the $HbA_{1c}$ estimate is validated or displayed only if the ratio (RLO1/RHI1>=about 0.005),
    wherein
    RLO1 is the Low BG Index of claim 6,
    RHI1 is the High BG Index of claim 6; or
  d) a randomness of data criterion-2 wherein $HbA_{1c}$ estimate is validated or displayed only if the ratio (NO6>=about 3%),
    wherein
    N06 is the percentage of readings during the night of claim 6.

16. The system of claim 15, wherein said third predetermined duration is at least 35 days.

17. The system of claim 15, wherein said third predetermined duration ranges from about 35 days to about 40 days.

18. The system of claim 15, wherein said third predetermined duration ranges from about 35 days to about as long as the first predetermined duration.

19. The system of claim 11, wherein the validation of the $HbA_{1c}$ estimate using sample selection criteria of $HbA_{1c}$ estimate only if the first predetermined duration sample meets at least one of the following four criteria:
  a) a test frequency criterion wherein if the first predetermined duration sample contains an average of at least about 1.5; and
  b) a randomness of data criterion-1 wherein the $HbA_{1c}$ estimate is validated or displayed only if the ratio (RLO1/RHI1>=about 0.005),
    wherein
    RLO1 is the Low BG Index of claim 6
    RHI1 is the High BG Index of claim 6; or
  c) a randomness of data criterion-2 wherein $HbA_{1c}$ estimate is validated or displayed only if the ratio (NO6>=about 3%),
    wherein
    N06 is the percentage of readings during the night of claim 6.

20. The system of claim 19, wherein said third predetermined duration is at least about 35 days.

21. A system for evaluating the $HbA_{1c}$ of a patient based on blood glucose (BG) data collected over a first predetermined duration, said system comprising:
  a BG acquisition mechanism, said acquisition mechanism configured to acquire BG data from the patient;
  a database component operative to maintain a database identifying said BG data; and
  a processor programmed to:
    pre-process the acquired BG data to convert the acquired BG data into derived BG data derived from said acquired BG data;
    estimate $HbA_{1c}$ by applying at least one predetermined formula to said derived BG data;
    validate the estimate via sample selection criteria; and
    output the estimate to a user.

22. The system of claim 21, wherein said first predetermined duration is about 60 days.

23. The system of claim 21, wherein said first predetermined duration ranges from about 45 days to about 75 days.

24. The system of claim 21, wherein said first predetermined duration ranges from about 45 days to about 90 days.

25. The system of claim 21, wherein the pre-processing of the data comprises:
  conversion of plasma data to whole blood BG mg/dl;
  conversion of BG measured in mg/dl to units of mmol/l; and
  computing Low Blood Glucose Index (RLO1) and High Blood Glucose Index (RHI1).

26. The system of claim 21, wherein the preprocessing of the data comprises:
  conversion of plasma data to whole blood BG mg/dl via BG=PLASBG (mg/dl) /1.12;
  conversion of BG measured in mg/dl to units of mmol/l) via BGMM=BG/18; and computing Low Blood Glucose Index (RLO1) and High Blood Glucose Index (RHI1) using a predetermined mathematical formula defined as:

Scale=$[\ln(BG)]^{1.0845}$−5.381, wherein BG is measured in units of mg/dl,

Risk1=22.765(Scale)$^2$, wherein

RiskLO=Risk1 if (BG is less than about 112.5) and therefore risk of LBGI exists, otherwise RiskLO=0, and RiskHI=Risk1 if (BG is greater than about 112.5) and therefore risk of HBGI exists, otherwise RiskHI=0, BGMM1=average of BGMM per patient, RLO1=average of RiskLO per patient, RHI1=average of RiskHI per patient, L06=average of RiskLO computed only for readings during the night, otherwise missing if there are no readings at night, N06, N12, N24 are percentage of SMBG readings in time intervals, NC1=total number of SMBG readings in the first predetermined duration; and NDAYS=number of days with SMBG readings in the first predetermined duration.

27. The system of claim 26, wherein the N06, N12, N24 are percentage of SMBG readings in time intervals of about 0-6:59 hour time period; about 7-12:59 hour time period, and about 18-23:59 hour time period, respectively.

28. The system of claim 26, comprising assigning a group depending on the patient's computed High BG Index using a predetermined mathematical formula defined as:

if (RHI1 is ≦about 5.25 or if RHI1 is ≧about 16) then the assigned group=0, if (RHI1 is >about 5.25 and if RHI1 is <about 7.0) then the assigned group=1, if (RHI1 is ≧about 7.0 and if RHI1 is <about 8.5) then the assign group=2, and if (RHI1 is ≧about 8.5 and if RHI1 is <about 16) then the assigned group=3.

29. The system of claim 28, comprising providing estimates using a predetermined mathematical formula defined as:

E0=0.55555*BGMM1+2.95,

E1=0.50567*BGMM1+0.074*L06+2.69,

E2=0.55555*BGMM1−0.074*L06+2.96,

E3=0.44000*BGMM1+0.035*L06+3.65; and if (Group=1) then EST2=E1, or if (Group=2) then EST2=E2, or if (Group=3) then EST2=E3, otherwise EST2=E0.

30. The system of claim 29, comprising providing further correction of the estimates using a predetermined mathematical formula defined as:

if (missing(L06)) EST2=E0, if (RLO1 is ≦about 0.5 and RHI1 is le about 2.0) then EST2=E0−0.25, if (RLO1 is ≦about 2.5 and RHI1 is >about 26) then EST2=E0−1.5*RLO1, and if ((RLO1/RHI1) is ≦about 0.25 and L06 is >about 1.3) then EST2=EST2−0.08.

31. The system of claim 30 for estimating the $HbA_{1c}$ of a patient based on BG data collected over the first predetermined duration, said system comprising:

said estimating $HbA_{1c}$ using said at least one of four predetermined mathematical formulas defined as:

a) $HbA_{1c}$=the EST2 defined by claim 28 or as corrected by claim 30 or b) $HbA_{1c}$=0.809098*BGMM1+0.064540*RLO1−0.151673*RHI1+1.873325, wherein BGMM1is the average BG (mmol/l) of claim 26, RLO1 is the Low BG Index of claim 26, RHI1 is the High BG Index of claim 26; or c) $HbA_{1c}$=0.682742*HBA0+0.054377*RHI1+1.553277, wherein HBA0 is a previous reference $HbA_{1c}$ reading taken about a second predetermined period prior to the estimate, wherein RHI1=is the High BG Index of claim 26; or d) $HbA_{1c}$=0.41046*BGMM+4.0775 wherein BGMM1is the average BG (mmol/l) of claim 26.

32. The system of claim 31, wherein said second predetermined duration is about three months.

33. The system of claim 31, wherein said second predetermined duration ranges from about 2.5 months to about 3.5 months.

34. The system of claim 31, wherein said second predetermined duration ranges from about 2.5 months to six months.

35. The system of claim 31, wherein the validation of the $HbA_{1c}$ estimate using sample selection criteria of $HbA_{1c}$ estimate only if the first predetermined duration sample meets at least one of the following four criteria:

a) a test frequency criterion wherein if the first predetermined duration sample contains an average of at least about 1.5 to about 2.5 tests per day;

b) an alternative test frequency criterion only if the predetermined duration sample contains at least a third predetermined sample period with readings with an average frequency of about 1.8 readings/day;

c) a randomness of data criterion-1 wherein the $HbA_{1c}$ estimate is validated or displayed only if the ratio (RLO1/RHI1>=about 0.005), wherein RLO1 is the Low BG Index of claim 26, RHI1 is the High BG Index of claim 26; or d) a randomness of data criterion-2 wherein $HbA_{1c}$ estimate is validated or displayed only if the ratio (NO6>=about 3%), wherein N06 is the percentage of readings during the night of claim 26.

36. The system of claim 35, wherein said third predetermined duration is at least 35 days.

37. The system of claim 35, wherein said third predetermined duration ranges from about 35 days to about 40 days.

38. The system of claim 35, wherein said third predetermined duration ranges from about 35 days to about as long as the first predetermined duration.

39. The system of claim 31, wherein the validation of the $HbA_{1c}$ estimate using sample selection criteria of $HbA_{1c}$ estimate only if the first predetermined duration sample meets at least one of the following four criteria:

a) a test frequency criterion wherein if the first predetermined duration sample contains an average of at least about 1.5; and b) a randomness of data criterion-1 wherein the $HbA_{1c}$ estimate is validated or displayed only if the ratio (RLO1/RHI1>=about 0.005), wherein RLO1 is the Low BG Index of claim 26

RHI1 is the High BG Index of claim 26; or c) a randomness of data criterion-2 wherein $HbA_{1c}$ estimate is validated or displayed only if the ratio (NO6>=about 3%), wherein N06 is the percentage of readings during the night of claim 26.

40. The system of claim 39, wherein said third predetermined duration is at least about 35 days.

41. A computer program product comprising a tangible computer readable medium having computer program logic for enabling at least one processor in a computer system to evaluate the $HbA_{1c}$ of a patient based on blood glucose (BG) data collected over a first predetermined duration, said computer program logic comprising:

pre-processing of the collected BG data to convert the collected BG data into derived BG data derived from said collected BG data, estimating $HbA_{1c}$ by applying at least one predetermined formula to said derived BG data, and validation of the estimate via sample selection criteria; and outputting the estimate to a user.

42. A system for evaluating the $HbA_{1c}$ of a patient based on blood glucose (BG) data collected over a first predetermined duration, said system comprising:

a database component operative to maintain a database identifying said BG data; and a processor programmed to:

pre-process the collected BG data to convert the collected BG data into derived BG data derived from said collected BG data, validate a sample of the collected BG data via sample selection criteria, and estimate $HbA_{1c}$ from said derived BG data if the sample is valid; and output the estimate to a user.

43. The system of claim 42, wherein said first predetermined duration is about 60 days.

44. The system of claim 42, wherein said first predetermined duration ranges from about 45 days to about 75 days.

45. The system of claim 42, wherein said first predetermined duration ranges from about 45 days to about 90 days.

46. The system of claim 42, wherein the preprocessing of the data comprises:

conversion of plasma to whole blood BG mg/dl;

conversion of BG measured in mg/dl to units of mmol/l; and computing Low Blood Glucose Index (RLO1) and High Blood Glucose Index (RHI1).

47. The system of claim 42, wherein the preprocessing of the data comprises:

conversion of plasma to whole blood BG mg/dl via BG=PLASBG (mg/dl) /1.12;

conversion of BG measured in mg/dl to units of mmol/l via BGMM=BG/18; and computing Low Blood Glucose Index (RLO1) and High Blood Glucose Index (RHI1) using a predetermined mathematical formula defined as:

Scale=$[\ln(BG)]^{1.0845}-5.381$, wherein BG is measured in units of mg/dl,

Risk1=$22.765(Scale)^2$, wherein

RiskLO=Risk1 if (BG is less than about 112.5) and therefore risk of LBGI exists, otherwise RiskLO=0, and RiskHI=Risk1 if (BG is greater than about 112.5) and therefore risk of HBGI exists, otherwise RiskHI=0, BGMM1=average of BGMM per patient, RLO1=average of RiskLO per patient, RHI1=average of RiskHI per patient, L06=average of RiskLO computed only for readings during the night, otherwise missing if there are no readings at night, N06, N12, N24 are percentage of SMBG readings in time intervals, NC1=total number of SMBG readings in the first predetermined duration; and NDAYS=number of days with SMBG readings in the first predetermined duration.

48. The system of claim 47, wherein the N06, N12, N24 are percentage of SMBG readings in time intervals of about 0-6:59 hour time period;

about 7-12:59 hour time period, and about 18-23:59 hour time period, respectively.

49. The system of claim 47, comprising assigning a group depending on the patient's computed High BG Index using a predetermined mathematical formula defined as:

if (RHI1 is $\leq$about 5.25 or if RHI1 is $\geq$about 16) then the assigned group=0, if (RHI1 is >about 5.25 and if RHI1 is <about 7.0) then the assigned group=1, if (RHI1 is $\geq$about 7.0 and if RHI1 is <about 8.5) then the assign group=2, and if (RHI1 is $\geq$about 8.5 and if RHI1 is <about 16) then the assigned group=3.

50. The system of claim 49, comprising providing estimates using a predetermined mathematical formula defined as:

E0=0.55555*BGMM1+2.95,

E1=0.50567*BGMM1+0.074*L06+2.69,

E2=0.55555*BGMM1−0.074*L06+2.96,

E3=0.44000*BGMM1+0.035*L06+3.65; and if (Group=1) then EST2=E1, or if (Group=2) then EST2=E2, or if (Group=3) then EST2=E3, otherwise EST2=E0.

51. The system of claim 50, comprising providing further correction of the estimates using a predetermined mathematical formula defined as:

if (missing(L06)) EST2=E0, if (RLO1 is $\leq$about 0.5 and RHI1 is le about 2.0) then EST2=E0−0.25, if (RLO1 is $\leq$about 2.5 and RHI1 is >about 26) then EST2=E0−1.5*RLO1, and if ((RLO1/RHI1) is $\leq$about 0.25 and L06 is >about 1.3) then EST2=EST2-0.08.

52. The system of claim 51 for estimating the $HbA_{1c}$ of a patient based on BG data collected over the first predetermined duration, said system comprising:

estimating $HbA_{1c}$ using at least one of four predetermined mathematical formulas defined as:

a) $HbA_{1c}$=the EST2 defined by claim 49 or as corrected by claim 51 or b) $HbA_{1c}$=0.809098*BGMM1+0.064540*RLO1−0.151673*RHI1+1.873325, wherein BGMM1 is the average BG (mmol/l) of claim 47, RLO1 is the Low BG Index of claim 47, RHI1 is the High BG Index of claim 47; or c) $HbA_{1c}$=0.682742*HBA0+0.054377*RHI1+1.553277, wherein HBA0 is a previous reference $HbA_{1c}$ reading taken about a second predetermined period prior to the estimate, wherein RHI1=is the High BG Index of claim 47; or d) $HbA_{1c}$=0.41046*BGMM+4.0775 wherein BGMM1 is the average BG (mmol/l) of claim 47.

53. The system of claim 52, wherein said second predetermined duration is about three months.

54. The system of claim 52, wherein said second predetermined duration ranges from about 2.5 months to about 3.5 months.

55. The system of claim 52, wherein said second predetermined duration ranges from about 2.5 months to six months.

56. The system of claim 52, wherein the validation of the sample using sample selection criteria of $HbA_{1c}$ estimate only if the first predetermined duration sample meets at least one of the following four criteria:
  a) a test frequency criterion wherein if the first predetermined duration sample contains an average of at least about 1.5 to about 2.5 tests per day;
  b) an alternative test frequency criterion only if the predetermined duration sample contains at least a third predetermined sample period with readings with an average frequency of about 1.8 readings/day;
  c) a randomness of data criterion-1 wherein the $HbA_{1c}$ estimate is validated or displayed only if the ratio (RLO1/RHI1>=about 0.005),
  wherein
  RLO1 is the Low BG Index of claim 47,
  RHI1 is the High BG Index of claim 47; or
  d) a randomness of data criterion-2 wherein $HbA_{1c}$ estimate is validated or displayed only if the ratio (NO6>=about 3%),
  wherein
  N06 is the percentage of readings during the night of claim 47.

57. The system of claim 56, wherein said third predetermined duration is at least 35 days.

58. The system of claim 56, wherein said third predetermined duration ranges from about 35 days to about 40 days.

59. The system of claim 56, wherein said third predetermined duration ranges from about 35 days to about as long as the first predetermined duration.

60. The system of claim 52, wherein the validation of the sample using sample selection criteria of $HbA_{1c}$ estimate only if the first predetermined duration sample meets at least one of the following four criteria:
  a) a test frequency criterion wherein if the first predetermined duration sample contains an average of at least about 1.5; and
  b) a randomness of data criterion-1 wherein the $HbA_{1c}$ estimate is validated or displayed only if the ratio (RLO1/RHI1>=about 0.005),
  wherein
  RLO1 is the Low BG Index of claim 47
  RHI1 is the High BG Index of claim 47; or
  c) a randomness of data criterion-2 wherein $HbA_{1c}$ estimate is validated or displayed only if the ratio (NO6>=about 3%),
  wherein
  N06 is the percentage of readings during the night of claim 47.

61. The system of claim 60, wherein said third predetermined duration is at least about 35 days.

62. A system for evaluating the $HbA_{1c}$ of a patient based on blood glucose (BG) data collected over a first predetermined duration, said system comprising:
  a BG acquisition mechanism, said acquisition mechanism configured to acquire BG data from the patient;
  a database component operative to maintain a database identifying said BG data; and
  a processor programmed to:
    pre-process the acquired BG data to convert the acquired BG data into derived BG data derived from said acquired BG data;
    validate a sample of the acquired BG data via sample selection criteria;
    estimate $HbA_{1c}$ from said derived BG data if the sample is valid; and
    output the $HbA_{1c}$ estimate to a user.

63. The system of claim 62, wherein said first predetermined duration is about 60 days.

64. The system of claim 62, wherein said first predetermined duration ranges from about 45 days to about 75 days.

65. The system of claim 62, wherein said first predetermined duration ranges from about 45 days to about 90 days.

66. The system of claim 62, wherein the preprocessing of the data comprises:
  conversion of plasma to whole blood BG mg/dl;
  conversion of BG measured in mg/dl to units of mmol/l; and
  computing Low Blood Glucose Index (RLO1) and High Blood Glucose Index (RHI1).

67. The system of claim 62, wherein the pre-processing of the data comprises:
  conversion of plasma to whole blood BG mg/dl via BG=PLASBG (mg/dl) /1.12;
  conversion of BG measured in mg/dl to units of mmol/l via BGMM=BG/18; and
  computing Low Blood Glucose Index (RLO1) and High Blood Glucose Index (RHI1) using a predetermined mathematical formula defined as:
  Scale=$[\ln(BG)]^{1.0845}-5.381$, wherein BG is measured in units of mg/dl,
  Risk1=22.765(Scale)$^2$, wherein
  RiskLO=Risk1 if (BG is less than about 112.5) and therefore risk of LBGI exists, otherwise RiskLO=0, and
  RiskHI=Risk1 if (BG is greater than about 112.5) and therefore risk of HBGI exists, otherwise RiskHI=0,
  BGMM1=average of BGMM per patient,
  RLO1=average of RiskLO per patient,
  RHI1=average of RiskHI per patient,
  L06=average of RiskLO computed only for readings during the night, otherwise missing if there are no readings at night,
  N06, N12, N24 are percentage of SMBG readings in time intervals,
  NC1=total number of SMBG readings in the first predetermined duration; and
  NDAYS=number of days with SMBG readings in the first predetermined duration.

68. The system of claim 67, wherein the N06, N12, N24 are percentage of SMBG readings in time intervals of about 0-6:59 hour time period;
  about 7-12:59 hour time period, and about 18-23:59 hour time period, respectively.

69. The system of claim 67, comprising assigning a group depending on the patient's computed High BG Index using a predetermined mathematical formula defined as:
  if (RHI1 is ≦about 5.25 or if RHI1 is ≧about 16) then the assigned group=0,
  if (RHI1 is >about 5.25 and if RHI1 is <about 7.0) then the assigned group=1,
  if (RHI1 is ≦about 7.0 and if RHI1 is <about 8.5) then the assign group=2, and
  if (RHI1 is ≦about 8.5 and if RHI1 is <about 16) then the assigned group=3.

70. The system of claim 69, comprising providing estimates using a predetermined mathematical formula defined as:
  E0=0.55555*BGMM1+2.95,
  E1=0.50567*BGMM1+0.074*L06+2.69,

E2=0.55555*BGMM1−0.074*L06+2.96,

E3=0.44000*BGMM1+0.035*L06+3.65; and if (Group=1) then EST2=E1, or if (Group=2) then EST2=E2, or if (Group=3) then EST2=E3, otherwise EST2=E0.

71. The system of claim 70, comprising providing further correction of the estimates using a predetermined mathematical formula defined as:

if (missing(L06)) EST2=E0, if (RLO1 is ≦about 0.5 and RHI1 is le about 2.0) then EST2=E0−0.25, if (RLO1 is ≦about 2.5 and RHI1 is >about 26) then EST2=E0−1.5*RLO1, and if ((RLO1/RHI1) is ≦about 0.25 and L06 is >about 1.3) then EST2=EST2−0.08.

72. The system of claim 71 for estimating the $HbA_{1c}$ of a patient based on BG data collected over the first predetermined duration, said system comprising:

estimating $HbA_{1c}$ using at least one of four predetermined mathematical formulas defined as:

a) $HbA_{1c}$=the EST2 defined by claim 69 or as corrected by claim 71 or b) $HbA_{1c}$=0.809098*BGMM1+0.064540*RLO1−0.151673*RHI1+1.873325, wherein BGMM1 is the average BG (mmol/l) of claim 67, RLO1 is the Low BG Index of claim 67, RHI1 is the High BG Index of claim 67; or c) $HbA_{1c}$=0.682742*HBA0+0.054377*RHI1+1.553277, wherein HBA0 is a previous reference $HbA_{1c}$ reading taken about a second predetermined period prior to the estimate, wherein RHI1=is the High BG Index of claim 67; or d) $HbA_{1c}$=0.41046*BGMM+4.0775 wherein BGMM1 is the average BG (mmol/l) of claim 67.

73. The system of claim 72, wherein said second predetermined duration is about three months.

74. The system of claim 72, wherein said second predetermined duration ranges from about 2.5 months to about 3.5 months.

75. The system of claim 72, wherein said second predetermined duration ranges from about 2.5 months to six months.

76. The system of claim 72, wherein the validation of the sample using sample selection criteria of $HbA_{1c}$ estimate only if the first predetermined duration sample meets at least one of the following four criteria:

a) a test frequency criterion wherein if the first predetermined duration sample contains an average of at least about 1.5 to about 2.5 tests per day;

b) an alternative test frequency criterion only if the predetermined duration sample contains at least a third predetermined sample period with readings with an average frequency of about 1.8 readings/day;

c) a randomness of data criterion-1 wherein the $HbA_{1c}$ estimate is validated or displayed only if the ratio (RLO1/RHI1>=about 0.005), wherein RLO1 is the Low BG Index of claim 67, RHI1 is the High BG Index of claim 67; or d) a randomness of data criterion-2 wherein $HbA_{1c}$ estimate is validated or displayed only if the ratio (NO6>=about 3%), wherein N06 is the percentage of readings during the night of claim 67.

77. The system of claim 76, wherein said third predetermined duration is at least about 35 days.

78. The system of claim 76, wherein said third predetermined duration ranges from about 35 days to about 40 days.

79. The system of claim 76, wherein said third predetermined duration ranges from about 35 days to about as long as the first predetermined duration.

80. The system of claim 72, wherein the validation of the sample using sample selection criteria of $HbA_{1c}$ estimate only if the first predetermined duration sample meets at least one of the following four criteria:

a) a test frequency criterion wherein if the first predetermined duration sample contains an average of at least about 1.5; and b) a randomness of data criterion-1 wherein the $HbA_{1c}$ estimate is validated or displayed only if the ratio (RLO1/RHI1>=about 0.005), wherein RLO1 is the Low BG Index of claim 67

RHI1 is the High BG Index of claim 67; or c) a randomness of data criterion-2 wherein $HbA_{1c}$ estimate is validated or displayed only if the ratio (NO6>=about 3%), wherein N06 is the percentage of readings during the night of claim 67.

81. The system of claim 80, wherein said third predetermined duration is at least about 35 days.

82. A system for evaluating the $HbA_{1c}$ of a patient without the need for prior $HbA_{1c}$ information based on blood glucose (BG) data collected over a first predetermined duration, said system comprising:

a database component operative to maintain a database identifying said BG data; and a processor programmed to:

pre-process the collected BG data to convert the collected BG data into derived BG data derived from said collected BG data, validate a sample of the collected BG data via sample selection criteria, and estimate $HbA_{1c}$ from said derived BG data if the sample is valid; and output the estimate to a user.

83. The system of claim 82, wherein said first predetermined duration is about 60 days.

84. The system of claim 82, wherein said first predetermined duration ranges from about 45 days to about 75 days.

85. The system of claim 82, wherein said first predetermined duration ranges from about 45 days to about 90 days.

86. The system of claim 82, wherein the preprocessing of the data comprises:

conversion of plasma data to whole blood BG mg/dl;

conversion of BG measured in mg/dl to units of mmol/l; and computing Low Blood Glucose Index (RLO1) and High Blood Glucose Index (RHI1).

87. The system of claim 82, wherein the preprocessing of the data comprises:

conversion of plasma to whole blood BG mg/dl via BG=PLASBG (mg/dl) /1.12;

conversion of BG measured in mg/dl to units of mmol/l via BGMM=BG/18; and computing Low Blood Glucose Index (RLO1) and High Blood Glucose Index (RHI1) using a predetermined mathematical formula defined as:

Scale=$[\ln(BG)]^{1.0845}$−5.381, wherein BG is measured in units of mg/dl,

Risk1=22.765(Scale)$^2$, wherein

RiskLO=Risk1 if (BG is less than about 112.5) and therefore risk of LBGI exists, otherwise RiskLO=0, and RiskHI=Risk1 if (BG is greater than about 112.5) and therefore risk of HBGI exists, otherwise RiskHI=0, BGMM1=average of BGMM per patient, RLO1=average of RiskLO per patient, RHI1=average of RiskHI per patient, L06=average of RiskLO computed only for readings during the night, otherwise missing if there are no readings at night, N06, N12, N24 are percentage of SMBG readings in time intervals, NC1=total number of SMBG readings in the first predetermined duration; and NDAYS=number of days with SMBG readings in the first predetermined duration.

88. A system for evaluating the $HbA_{1c}$ of a patient without the need for prior $HbA_{1c}$ information based on blood glucose (BG) data collected over a first predetermined duration, said system comprising:

a BG acquisition mechanism, said acquisition mechanism configured to acquire BG data from the patient;

a database component operative to maintain a database identifying said BG data; and a processor programmed to:
pre-process the collected BG data to convert the collected BG data into derived BG data derived from said collected BG data;
validate a sample of the collected BG data via sample selection criteria;
estimate $HbA_{1c}$ from said derived BG data if the sample is valid; and
output the $HbA_{1c}$ estimate to a user.

89. The system of claim 88, wherein said first predetermined duration is about 60 days.

90. The system of claim 88, wherein said first predetermined duration ranges from about 45 days to about 75 days.

91. The system of claim 88, wherein said first predetermined duration ranges from about 45 days to about 90 days.

92. The system of claim 88, wherein the preprocessing of the data comprises:

conversion of plasma data to whole blood BG mg/dl;

conversion of BG measured in mg/dl to units of mmol/l; and computing Low Blood Glucose Index (RLO1) and High Blood Glucose Index (RHI1).

93. The system of claim 88, wherein the preprocessing of the data is defined as:

conversion of plasma to whole blood BG mg/dl via BG=PLASBG (mg/dl) /1.12;

conversion of BG measured in mg/dl to units of mmol/l via BGMM=BG/18; and computing Low Blood Glucose Index (RLO1) and High Blood Glucose Index (RHI1) using a predetermined mathematical formula defined as:

Scale=$[\ln(BG)]^{1.0845}-5.381$, wherein BG is measured in units of mg/dl,

Risk1=$22.765(\text{Scale})^2$, wherein

RiskLO=Risk1 if (BG is less than about 112.5) and therefore risk of LBGI exists, otherwise RiskLO=0, and RiskHI=Risk1 if (BG is greater than about 112.5) and therefore risk of HBGI exists, otherwise RiskHI=0, BGMM1=average of BGMM per patient, RLO1=average of RiskLO per patient, RHI1=average of RiskHI per patient, L06=average of RiskLO computed only for readings during the night, otherwise missing if there are no readings at night, N06, N12, N24 are percentage of SMBG readings in time intervals, NC1=total number of SMBG readings in the first predetermined duration; and NDAYS=number of days with SMBG readings in the first predetermined duration.

* * * * *